US011078270B2

(12) United States Patent
Marfia et al.

(10) Patent No.: US 11,078,270 B2
(45) Date of Patent: Aug. 3, 2021

(54) USE OF NEGATIVE FUNCTIONAL MODULATORS OF ERYTHROPOIETIN FOR THERAPY

(71) Applicant: ANDREMACON S.R.L., Milan (IT)

(72) Inventors: Giovanni Marfia, Milan (IT); Stefania Elena Navone, Milan (IT); Giuseppe Scalvini, Milan (IT); Laura Riboni, Milan (IT); Rolando Campanella, Milan (IT)

(73) Assignee: ANDREMACON S.R.L., Milan (IT)

( * ) Notice: Subject to any disclaimer, the term of this patent is extended or adjusted under 35 U.S.C. 154(b) by 0 days.

(21) Appl. No.: 15/318,007

(22) PCT Filed: Jun. 12, 2015

(86) PCT No.: PCT/IB2015/054455
§ 371 (c)(1),
(2) Date: Dec. 12, 2016

(87) PCT Pub. No.: WO2015/189813
PCT Pub. Date: Dec. 17, 2015

(65) Prior Publication Data
US 2017/0114132 A1    Apr. 27, 2017

(30) Foreign Application Priority Data

Jun. 12, 2014  (IT) .......................... MI2014A001067

(51) Int. Cl.
*A61K 39/00*  (2006.01)
*C07K 16/26*  (2006.01)
*C07K 16/28*  (2006.01)
*C07K 16/22*  (2006.01)
*A61K 31/137*  (2006.01)
*A61K 31/7105*  (2006.01)
*A61K 39/395*  (2006.01)
*A61K 45/06*  (2006.01)
*C07K 14/72*  (2006.01)
*C12N 15/113*  (2010.01)
*G01N 33/50*  (2006.01)

(52) U.S. Cl.
CPC ............ *C07K 16/26* (2013.01); *A61K 31/137* (2013.01); *A61K 31/7105* (2013.01); *A61K 39/3955* (2013.01); *A61K 39/39541* (2013.01); *A61K 45/06* (2013.01); *C07K 14/72* (2013.01); *C07K 16/22* (2013.01); *C07K 16/2863* (2013.01); *C07K 16/2869* (2013.01); *C12N 15/1136* (2013.01); *G01N 33/5023* (2013.01); *A61K 2039/505* (2013.01); *C07K 2317/34* (2013.01); *C12N 2310/14* (2013.01); *G01N 2500/04* (2013.01); *G01N 2500/10* (2013.01)

(58) Field of Classification Search
None
See application file for complete search history.

(56) References Cited

U.S. PATENT DOCUMENTS

2004/0096447 A1* 5/2004 Yasuda .................. C07K 16/22
424/145.1
2014/0120079 A1* 5/2014 Zhang .................. C12Q 1/6883
424/130.1

FOREIGN PATENT DOCUMENTS

| EP | 1459762 A1 | 9/2004 |
| JP | H10101574 A | 4/1998 |
| JP | 2012162500 A | 8/2012 |
| WO | 2005099773 A1 | 10/2005 |
| WO | 2009074969 A2 | 6/2009 |
| WO | 2010000875 A1 | 1/2010 |

OTHER PUBLICATIONS

Lloyd et al. Functional prediction of mitochondrial DNA mutations in glioblastoma multiforme. Neuro-Oncology, vol. 16, Supp. SUPPL. 2, pp. ii97. Abstract No. P17.51; (Sep. 2014). (Year: 2014).*
Dermer. Another anniversary for the war on cancer; Bio/Technology, vol. 12, No. 3 p. 320 (Mar. 1994). (Year: 1994).*
Wakabayashi et al. Prevention of metastasis by a polyamine synthesis inhibitor in an animal bone metastasis model. Oncology, 59: 75-80 (2000). (Year: 2000).*
O'Donnell et al. Bone pain associated with cancer metastasis. Bone and Cancer, Topics in Bone Biology, vol. 5:167-178 (2009). (Year: 2009).*
Nico et al. Epo is involved in angiogenesis in human glioma. J Neurooncol vol. 102:51-58, 2011. (Year: 2011).*
Estrada-Bernal et al. Induction of brain tumor stem cell apoptosis by FTY720: a potential therapeutic agent for glioblastoma. ABSTRACT. Neuro-oncology, vol. 14, No. 4, pp. 405-415. Electronic Publication Date: Feb. 20, 2012; Apr. 2012. (Year: 2012).*
Estrada-Bernal et al. Fty720 as a potential therapeutic agent for glioblastoma. Neuro-Oncology, ABSTRACT No. SC-10. vol. 12, SUPPL 4, pp. iv121 (Year: 2010).*

(Continued)

*Primary Examiner* — Elizabeth C. Kemmerer
*Assistant Examiner* — Regina M DeBerry
(74) *Attorney, Agent, or Firm* — Silvia Salvadori, P.C.; Silvia Salvadori

(57) ABSTRACT

The invention relates to negative functional modulators of erythropoietin (EPO) for use in the treatment of cancers, in the therapy of autoimmune -based and non-autoimmune based chronic inflammatory diseases, and in the treatment of patients under-going organ or tissue transplant, or for the treatment of hemophilic arthropathy, hemophilia A and B, von Willebrand disease, angiodysplasia, proliferative disorders and neurological diseases characterized in their pathogenesis by primary neuroinflammation and/or neuroinflammation secondary to other causes. Such modulators are anti-EPO antibodies and their derivatives: anti-EPO receptor antibodies (EPOR), antisense oligonucleotides, decoy DNA, decoy RNA, ribozyme, antagomir, shRNA, LNA and/or siRNAs that inhibit the expression of the gene encoding EPO or EPOR.

6 Claims, 42 Drawing Sheets
Specification includes a Sequence Listing.

(56) References Cited

OTHER PUBLICATIONS

Tokuriki et al., Stability effects of mutations and protein evolvability; Current Opinion in Structural Biology, 19:596-604 (2009). (Year: 2009).*

Bhattacharya et al. (Impact of genetic variation on three dimensional structure and function of proteins; PLOS One 12(3): e0171355, pp. 1-22 ( Mar. 2017). (Year: 2017).*

Santa Cruz Biotechnology, Inc. EPO (XX9): sc-73963. Datasheet [online]. Santa Cruz Biotechnology, Inc. Copyright 2007-2020 [retrived on Jun. 16, 2020]. Retrived from the Internet: <http://datasheets.scbt.com/sc-73963.pdf> (Year: 2007).*

Bonder, C. et al., "Sphingosine kinase regulates the rate of endothelial progenitor cell differentiation", Blood, vol. 113, No. 9, Feb. 2009, pp. 2108-2117.

Hardee, M. et al., "Erythropoietin biology in cancer", Clinical Cancer Research, The American Association for Cancer Research, US, vol. 12, No. 2, Jan. 15, 2006, pp. 332-339.

International Search Report and Written Opinion of PCT/IB2015/054455 dated Oct. 14, 2015.

Udupa, K-B, "Functional significance of erythropoietin receptor on tumor cells," World Journal of Gastroenterology, WJG Press, CN, vol. 12, No. 46, Dec. 14, 2006, pp. 7460-7462.

Yasuda, Y et al., "Inhibition of erythropoietin signalling destroys xenografts of ovarian and uterine cancers in nude mice", British Journal of Cancer, vol. 84, No. 6, Mar. 23, 2001, pp. 836-843.

JP2012162500 (Univ Tsukuba) Aug. 30, 2012 (abstract). [online] [retrieved on Oct. 14, 2015]. Retrieved from WPI Database Agent useful for treating cancer, preferably cervical cancer comprising substance inhibiting expression of gene encoding EPO receptor or substance function of EPO receptor.

JPH10101574 (Snow Brand Milk Prod Co LTD) Apr. 21, 1998 (abstract). [online] [retrieved on Oct. 14, 2015]. Retrieved from WPI Database. Treatment and improving agent for proliferative organ diseases—contains erythropoietin antagonist.

* cited by examiner

Fig. 1

SEQ.2

28 app rlicdsrvle rylleakeae nittgcaehc
61 slnenitvpd tkvnfyawkr mevgqqavev wqglallsea vlrgqallvn ssqpweplql
121 hvdkavsglr slttllralg aqeaisppda asaaplrtit adtfrklfrv ysnflrgklk
181 lytgeacrtgdr Fig. 11
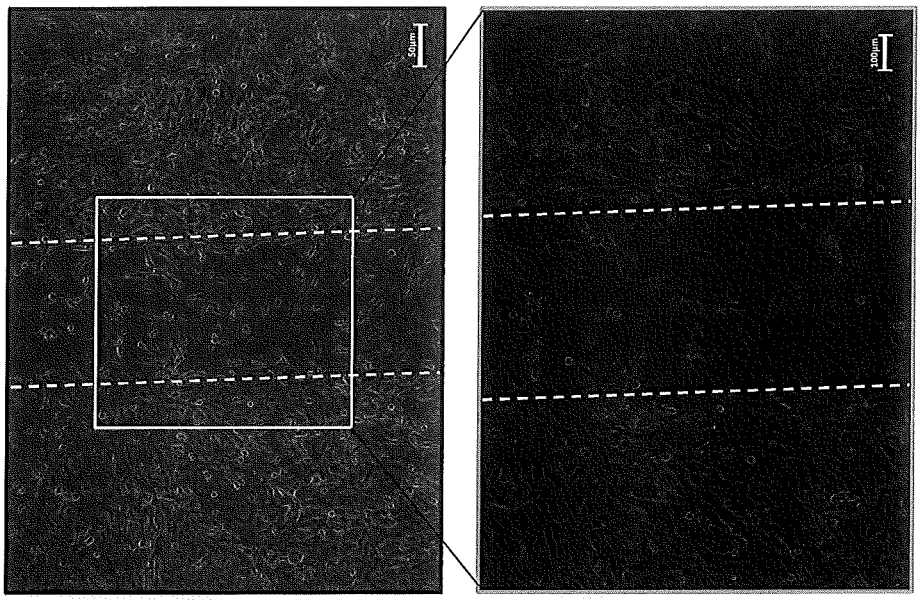
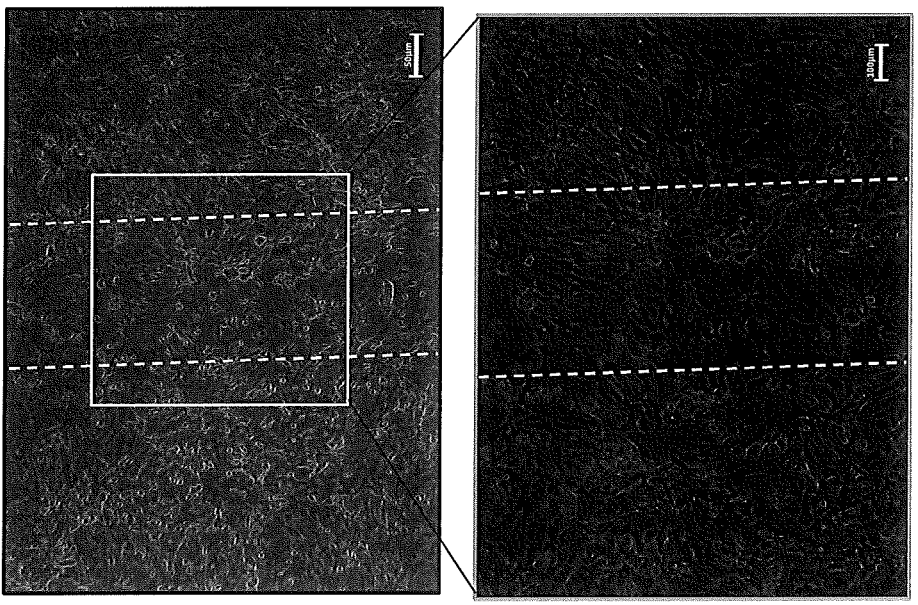

SEQUENCE LISTING

<160> NUMBER OF SEQ ID NOS: 2

<210> SEQ ID NO 1
<211> LENGTH: 2901
<212> TYPE: DNA
<213> ORGANISM: Artificial Sequence
<220> FEATURE:
<223> OTHER INFORMATION: Human EPO gene

<400> SEQUENCE: 1

| | | | | | |
|---|---|---|---|---|---|
| cccggagccg | gaccggggcc | accgcgcccg | ctctgctccg | acaccgcgcc | ccctggacag   60 |
| ccgccctctc | ctccaggccc | gtggggctgg | ccctgcaccg | ccgagcttcc | cgggatgagg  120 |
| gcccccggtg | tggtcacccg | cgcgccccca | ggtcgctgag | gaccccggcc | caggcgcgga  180 |
| gatggggtg  | cacggtgagt | actcgcgggc | tgggcgctcc | cgcccgcccg | ggtccctgtt  240 |
| tgagcgggga | tttagcgccc | cggctattgg | ccaggaggtg | gctgggttca | aggaccggcg  300 |
| acttgtcaag | gaccccggaa | gggggagggg | ggtgggggcag | cctccacgtg | ccagcgggga  360 |
| cttgggggag | tccttgggga | tggcaaaaac | ctgacctgtg | aaggggacac | agtttggggg  420 |
| ttgagggaa  | gaaggtttgg | gggttctgct | gtgccagtgg | agaggaagct | gataagctga  480 |
| taacctgggc | gctggagcca | ccacttatct | gccagagggg | aagcctctgt | cacaccagga  540 |
| ttgaagtttg | gccggagaag | tggatgctgg | tagctggggg | tggggtgtgc | acacggcagc  600 |
| aggattgaat | gaaggccagg | gaggcagcac | ctgagtgctt | gcatggttgg | ggacaggaag  660 |
| gacgagctgg | ggcagagacg | tggggatgaa | ggaagctgtc | cttccacagc | cacccttctc  720 |
| cctccccgcc | tgactctcag | cctggctatc | tgttctagaa | tgtcctgcct | ggctgtggct  780 |
| tctcctgtcc | ctgctgtcgc | tccctctggg | cctcccagtc | ctgggcgccc | caccacgcct  840 |
| catctgtgac | agccgagtcc | tggagaggta | cctcttggag | gccaaggagg | ccgagaatat  900 |
| cacggtgaga | ccccttcccc | agcacattcc | acagaactca | cgctcagggc | ttcagggaac  960 |
| tcctcccaga | tccaggaacc | tggcacttgg | tttggggtgg | agttgggaag | ctagacactg 1020 |
| cccccctaca | taagaataag | tctggtggcc | ccaaaccata | cctggaaact | aggcaaggag 1080 |
| caaagccagc | agatcctacg | gcctgtgggc | cagggccaga | gccttcaggg | acccttgact 1140 |
| cccccgggctg | tgtgcatttc | agacgggctg | tgctgaacac | tgcagcttga | atgagaatat 1200 |
| cactgtccca | gacaccaaag | ttaatttcta | tgcctggaag | aggatggagg | tgagttcctt 1260 |
| tttttttttt | tttcctttct | tttggagaat | ctcatttgcg | agcctgattt | tggatgaaag 1320 |
| ggagaatgat | cgagggaaag | gtaaaatgga | gcagcagaga | tgaggctgcc | tgggcgcaga 1380 |
| ggctcacgtc | tataatccca | ggctgagatg | gccgagatgg | gagaattgct | tgagccctgg 1440 |
| agtttcagac | caacctaggc | agcatagtga | gatcccccat | ctctacaaac | atttaaaaaa 1500 |
| attagtcagg | tgaggtggtg | catggtggta | gtcccagata | tttggaaggc | tgaggcggga 1560 |
| ggatcgcttg | agcccaggaa | tttgaggctg | cagtgagctg | tgatcacacc | actgcactcc 1620 |
| agcctcagtg | acagagtgag | gccctgtctc | aaaaaagaaa | agaaaaaga  | aaataatga  1680 |
| gggctgtatg | gaatacattc | attattcatt | cactcactca | ctcactcact | cattcattca 1740 |
| ttcattcatt | caacaagtct | tattgcatac | cttctgtttg | ctcagcttgg | tgcttggggc 1800 |
| tgctgagggg | caggagggag | agggtgacat | gggtcagctg | actcccagag | tccactccct 1860 |
| gtaggtcggg | cagcaggccg | tagaagtctg | gcagggcctg | gccctgctgt | cggaagctgt 1920 |
| cctgcggggc | caggccctgt | tggtcaactc | ttcccagccg | tgggagcccc | tgcagctgca 1980 |
| tgtggataaa | gccgtcagtg | gccttcgcag | cctcaccact | ctgcttcggg | ctctgggagc 2040 |

-continued

```
ccaggtgagt aggagcggac acttctgctt gcccttctg taagaagggg agaagggtct    2100
tgctaaggag tacaggaact gtccgtattc cttcccttc tgtggcactg cagcgacctc    2160
ctgttttctc cttggcagaa ggaagccatc tcccctccag atgcggcctc agctgctcca    2220
ctccgaacaa tcactgctga cactttccgc aaactcttcc gagtctactc caatttcctc    2280
cggggaaagc tgaagctgta cacaggggag gcctgcagga caggggacag atgaccaggt    2340
gtgtccacct gggcatatcc accacctccc tcaccaacat tgcttgtgcc acaccctccc    2400
ccgccactcc tgaaccccgt cgaggggctc tcagctcagc gccagcctgt cccatggaca    2460
ctccagtgcc agcaatgaca tctcaggggc cagaggaact gtccagagag caactctgag    2520
atctaaggat gtcacagggc aacttgagg gcccagagca ggaagcattc agagagcagc     2580
tttaaactca gggacagagc catgctggga agacgcctga gctcactcgg caccctgcaa    2640
aatttgatgc caggacacgc tttggaggcg atttacctgt tttcgcacct accatcaggg    2700
acaggatgac ctggataact taggtggcaa gctgtgactt ctccaggtct cacgggcatg    2760
ggcactccct tggtggcaag agcccccttg acaccggggt ggtgggaacc atgaagacag    2820
gatgggggct ggcctctggc tctcatgggg tccaagtttt gtgtattctt caacctcatt    2880
gacaagaact gaaaccacca a                                               2901
```

<210> SEQ ID NO 2
<211> LENGTH: 162
<212> TYPE: PRT
<213> ORGANISM: Artificial Sequence
<220> FEATURE:
<223> OTHER INFORMATION: Human EPO (aa 28-189)

<400> SEQUENCE: 2

```
Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Glu Ala Ile Ser Pro Pro Asp Ala Ala Ser Ala Ala Pro
        115                 120                 125

Leu Arg Thr Ile Thr Ala Asp Thr Phe Arg Lys Leu Phe Arg Val Tyr
    130                 135                 140

Ser Asn Phe Leu Arg Gly Lys Leu Lys Leu Tyr Thr Gly Glu Ala Cys
145                 150                 155                 160

Arg Thr
```

USE OF NEGATIVE FUNCTIONAL MODULATORS OF ERYTHROPOIETIN FOR THERAPY

This application is a U.S. national stage of PCT/IB2015/054455 filed on 12 Jun. 2015 which claims priority to and the benefit of Italian Application No. MI2014A001067 filed on 12 Jun. 2014, the content of which are incorporated herein by reference in their entireties.

FIELD OF THE INVENTION

The present invention relates to negative functional modulators of erythropoietin (EPO). The compounds of the invention, alone or in combination, are effective in the treatment of proliferative disorders such as cancers, where they cause the induction of apoptosis in cancer stem cells, in the therapy of autoimmune and non-autoimmune based chronic inflammatory diseases, in the treatment of patients undergoing organ or tissue transplant, in the treatment of haemophilic arthropathy, and in neurological diseases in which neuro inflammation plays a role in pathogenesis, for example: multiple sclerosis, Parkinson's disease, Alzheimer's disease, frontotemporal dementia, dementia with Lewy bodies, autoimmune disease with neurologic involvement, Amyotrophic Lateral Sclerosis, and Neuromuscular Diseases.

BACKGROUND

Monoclonal or polyclonal antibodies, represent the segment of the market which is developing most rapidly in the pharmaceutical industry. Despite a number of disadvantages, they are particularly valued among the biotherapies for their unique characteristics, such as high target specificity, favorable pharmacokinetics (high half-life), as well as a fast development and a high frequency of success when compared to small molecules. Moreover, due to advances in new technologies, the ability to engineer and humanize specifically purified monoclonal immunoglobulins, represents one of the most profitable areas of new biotechnology, opening up new avenues for their use in different areas of medicine. Cancers are a group of diseases characterized by uncontrolled growth and invasiveness and spread of abnormal cells. Their cause is due to external factors such as tobacco, chemical products, radiation and internal factors, such as inherited mutations, hormones and paracrine factors, imbalances in the immune system and DNA damage.

These factors may act together or in sequence to initiate and/or promote carcinogenesis. In the US, cancer is currently the leading cause of death in people under the age of 85 years. It is expected that about half of the male population and just over a third of women in the US will develop cancer during their lifetime. Today, millions of people are living with cancer or have had cancer. It is common practice to distinguish cancers into two families: solid cancers and non-solid cancers, that is blood cancers.

The majority of solid tumors, due to their scarce and abnormal vascular development, present median levels of oxygen partial pressures which are lower than those of the original tissue. The hypoxic microenvironment present in solid tumors gives them a greater aggressiveness and higher metastatic potential. In the hypoxic environment there is, through the stabilization of the transcription factor HIF1 $\alpha$ (Hypoxia-Inducible Factor 1$\alpha$), an increase in the expression of angiogenesis-related proteins, such as VEGF (Vascular Endothelial Growth Factor) and its receptor VEGFR, to prevail the anaerobic energy metabolism and adaptation to oxidative stress (Maxwell et al., 1997). Experimental evidence has shown that the tumor mass is composed of a large number of cells capable of limited proliferation and of a rare population of cells, called cancer stem cells (CSCs), characterized by an unlimited proliferative activity and capable of maintaining the tumor. Cancer stem cells possess two distinctive features: they are able to self-renew and also to undergo processes of differentiation into more mature cells. These characteristics give the cancer stem cells a key role in the processes responsible for the initiation and maintenance of the cancer and also in the resistance of the cancer to therapeutic treatments and, consequently to their recurrences. As such, they constitute an important therapeutic target, but the mechanisms underlying their pathobiology are still poorly understood; making it difficult to identify molecules able to target them. Hypoxia, induced by HIF and sphingolipids, plays a key role in the control of tumor growth and angiogenesis and constitutes one of the most effective coping mechanisms of the tumor. The genes involved in the biosynthetic pathway of neurogenesis and hypoxia are overexpressed by CSCs in the vascular niche/perinecrotic hypoxia, but not from the transitional tissue at the resection margin, if it has been defined as "disease-free" in anatomical pathological terms. Hypoxia plays a key role in the regulation of CSCs through HIF induction and through its target genes (VEGF, GLUT-1, NOS, EPO). CSCs show specific activation of HIF1 $\alpha$ and MAP kinases and, as recently demonstrated, they synthesize and effectively release sphingosine-1-phosphate (S1P) in relation to the hypoxic stimulus (Riccitelli et al., 2013). Riccitelli et al., 2013, using glioblastoma stem cells, showed that CSCs, and in particular glioblastoma stem cells (GSCs) synthesize S1P and export it into the extracellular environment where it promotes resistance to chemotherapy.

S1P exerts its action by stimulating proliferation, survival and drug resistance of cancer cells and cancer stem cells, as well as promoting angiogenesis by acting on stem cells and endothelial cells. Although S1P can act as a second intracellular messenger, most of its effects are exerted by extracellular mediators, through binding to specific receptors coupled to G proteins, originally known as EDG and now called S1P receptors (S1PRs). Due to its important role in the control of proliferation and cell viability, the interaction of S1P and its receptors, previously studied for its impact in autoimmune diseases, is the subject of intense study, with the objective of identifying new and more effective anticancer drugs. To date, an analogue of sphingosine, FTY720, has been identified, which, after phosphorylation, acts as a functional antagonist of S1PRs. FTY720 has been found effective in post-organ transplant therapy, multiple sclerosis, and, in vitro, in decreasing tumor growth in different types of tumors.

Inflammation is an innate nonspecific defense mechanism, which constitutes a protective response of the organism resulting in the harmful action of physical, chemical and biological agents, and whose ultimate goal is the elimination of the initial cause of cell or tissue damage or an autoimmune reaction. The immune system is the system responsible for the inflammatory response, and is made up of different cell types, tissues and immune organs. The normal inflammatory response is an acute process that is resolved after removal of the stimulus that caused it. In contrast, when the inflammatory response progresses, either due to repeated exposure to a stimulus, or when the causative agent is not suitably removed, the process becomes chronic. Depending on the tissue and on the phase of inflammation in which it is found, there is activation of different cell types. Inflammation can be triggered by autoimmune phenomena of recognition by the immune system by "self" antigens.

Neuroinflammation in particular is an inflammatory "cytokine-mediated" process that can be caused by systemic tissue damage or, more often, by direct damage to the central nervous system (CNS). Neuroinflammation differs from inflammation by the reduced presence of lymphatic vessels within the brain parenchyma; the lack of endogenous cells capable of presenting the antigen and the presence of the blood-brain barrier, which reduces the exchange of immune cells and inflammation mediators within the bloodstream. The persistence of the inflammatory processes in the CNS can cause serious damage to the neural complex and compromise its functional integrity.

Neuroinflammation may have different origins such as biological origin, for example ischemia, bacterial infections, the deposit of biological material (Alzheimer's and Parkinson's), intracellular and extracellular storage diseases that trigger neuroinflammation, and traumatic origin, such as brain trauma, and an autoimmune origin. All these conditions are able to activate the innate immune response in the CNS. Microglial cells represent 5-10% of the total cell population in the brain. It is a population of hematopoietic derivation: during embryogenesis, in fact, a subpopulation of monocytes migrates in the nervous system and differentiates into resident macrophages.

The microglial cells are comprised of a small cell body and by long processes tapered with lamellipodia that give them a branched morphology. They spread evenly in the brain parenchyma and can adhere to the neurons, but also to blood vessels and spread freely in the grey matter. These cells are inside the blood-brain barrier and therefore are ready to receive and respond to any damage to the same barrier. The microglia is normally dormant in the CNS, the cell soma remains almost motionless while the branches move constantly to monitor their surroundings. The occurrence of physiological changes in the environment, such as increased serum proteins, glutamate toxicity, deposits of amyloid, Tau and phospho-Tau protein and amorphous substances, increase of purines (ATP, ADP) or the presence of lipopolysaccharide (the molecule present the membrane of Gram-negative bacteria) are all stimuli that are able to activate microglia by different receptors and signaling pathways. The microglial cells present in the perivascular areas also exert the function of antigen-presenting cells (APC) on myelin-specific T cells, which have infiltrated the CNS and that may begin the inflammatory processes. (Ransohoff and Perry 2009). When the microglia is activated, it passes from a branched morphology to an amoeboid morphology. The lamellipodia retract and the cell assumes its phagocytic capacity, in order to eliminate the residue of any dead cells or engulf bacteria and viruses. The main role of activated microglia is to promote and support the inflammation state through the production of cytokines, reactive oxygen intermediates, proteinase, complement factors and chemokines.

Such inflammatory mediators promote the infiltration of immune cells from the bloodstream, the recruitment of other microglial cells from the surrounding areas and the activation of astrocytes. When the inflammatory stimulus that triggered the activation fails, the microglia participate in the suppression processes of the inflammatory state with the production of immunomodulatory cytokines, such as IL-15, and anti-inflammatory, such as IL-10; subsequently returning to a state of inactivation, or undergoing apoptosis (Lee, Nagai et al. 2002; Garden and Moller 2006). The microglial activation and neuroinflammatory events that follow are directed to neuroprotection and the elimination of the cause of homeostasis failure. In reality, both in neurodegenerative diseases of a chronic nature and in traumatic events, such as ischemia, uncontrolled and persistent microglial activation may have neurotoxic effects and contribute to exacerbate neuronal damage. The balance between neuroprotective and neurotoxic action of microglia is determined by several factors, including the nature of the stimulus and the interactions that develop between microglia, the other cells of the immune system and the neural network, so it is too simplistic to categorize the role of microglia in an absolute way and further study is certainly needed to shed light on the mechanisms that regulate this dual role (Harry and Kraft 2008). Much evidence has demonstrated that the modulation of microglia activation, and the inflammatory state in the brain in general, is able to improve the symptoms of many pathological conditions and to decrease the phenomenon of neurodegeneration (Morganti-Kossmann, Rancan et al. 2002; McGeer and McGeer 2007; Gonsette 2008; Shie, Nivison et al. 2009). Based on these observations, microglial activation represents a potential pharmacological target for the treatment of neurodegenerative and inflammatory diseases.

Hemophilic arthropathy is considered to be an inflammatory-like illness. In the context of chronic inflammation, hemophilic arthropathy (linked to a deficit of factor VIII/IX) represents a specific framework characterized by synovial hyperplasia supported by increased angiogenesis tumor-like aberrant features. This framework involves an increased frequency of bleeding intra-articular until complete destruction of tissues resulting in ankylosis and complete loss of motor function. The replacement therapy currently available based on the use of concentrates of factor VIII/IX is not able to prevent the development of joint damage (Manco-Johonson M. et al. New England Journal of Medicine 2007). Instead, therapies that interfere with angiogenesis, synovial proliferation and the intrinsic inflammation process that follows, can interrupt the vicious circle of synovitis-bleeding-inflammation.

The human erythropoietin (EPO) is a glycoprotein of 30.4 kDa produced and secreted primarily by the kidneys. EPO is normally present in the bloodstream where it is the main erythropoietin hormone. EPO is responsible for regulating the production of red blood cells, by stimulating the proliferation and differentiation of erythroid progenitors, as well as the retention of the same erythroid. EPO interacts with a specific receptor located on progenitors in the bone marrow, while all the targets in the nervous and non-nervous system that mediate the "non-erythropoietic" functions are not yet clearly defined. The use of EPO and its derivatives is well known in the treatment of anemia from renal failure, reduced erythropoiesis and in combination with myelosuppressive chemotherapy regimens in the treatment of malignancies.

EP1067955 describes the use of EPO in the inhibition of tumor growth, where EPO stimulates the natural immune response against cancer cells.

WO2005099773 describes the use of EPO or its analogue in inhibiting angiogenesis in tumors, an effect that is believed to be mediated by the ability of EPO to reduce the levels of HIF-1 alpha in tumor cells. This document does not describe the use of an anti-EPO antibody for the treatment of malignancies.

WO 2010/000875 A1 refers to a molecule able to bind to the EPO receptor with an antibody whose Complementary Determining Regions (CDRs) are included in a list of amino acid sequences defined by the authors with the acronyms CDR1, CDR2, CDR3. Therefore, this document describes the use of particular well-defined molecules directed only towards the EPO receptor, and that binding EPOR, have the property of inhibiting/compromising the rate of tumor cell invasion.

Yasuda et al., British Journal of Cancer, vol. 84, no. 6, 2001, refers to the in vivo treatment of murine animal models with monoclonal antibody anti-EPOR2 and a soluble form of the EPOR. The antibody in question, R2, was obtained and characterized in Goto et al. 1989. However, there is no description of the epitope against which the antibody R2 is directed.

EP 1459762 describes peptides that bind EPO and which are receptor antagonists of EPO. However, this document does not describe an anti-EPO antibody and its pharmaceutical use.

JP2012162500 does not describe an anti-EPO antibody that recognize and binds to the AA 28-189 Human EPO.

WO2009/074969 does not describe the use of an anti-EPO antibody and/or the combined use with anti-EPO and an antagonist of sphingosine-1-phosphate in the treatment of malignancies, in haemophilic arthropathy and much less in pathologies linked to neuroinflammation, identifying an anti-EPO antibody able to block the synthesis and release of sphingosine-1-phosphate.

Hardee et al., Clinical Cancer Research, The American Association for Cancer Research, Vol. 12, no. 2, p. 332-339, 2006, is a review that describes the role of EPO in tumors. In particular, the authors describe the expression of EPOR on cancer cells and the relationship EPO-EPOR, suggesting that an exogenous treatment with rEPO, recombinant EPO, could have direct effects on tumor cells, acting on the proliferation, apoptosis, and modulation of the sensitivity of these cells to chemotherapeutic agents. The authors conclude that further research to study the autocrine-paracrine system of EPO-EPOR is necessary, without demonstrating any biological mechanism on cancer cells and above all, arguing that there is opposed evidence that suggests how beneficial the administration of EPO in some tumors is. The review does not describe molecules able to function through the inhibition of the synthesis and/or release of sphingosine-1-phosphate.

According to the clinical picture described above, and to the information available in the field, there is a strong need for new therapeutic approaches for the treatment of tumors, effective even at the level of cancer stem cells and even in particularly aggressive tumors, such as the glioblastoma for example, which is the most common and aggressive malignant tumor of the central nervous system.

In particular, there is a very strong need for more effective compounds able to act on the synthesis of S1P and/or on the S1P/S1PRs interaction, such as new and powerful anticancer and valid therapies in the treatment of autoimmune and non-autoimmune based chronic inflammatory diseases, neuroinflammation in particular, in the treatment of patients undergoing organ or tissue transplants, in the treatment of hemophilic arthropathy and neurological diseases in which abnormal or excessive activation of the autoimmune system has a pathogenic role.

It is therefore an object of the present invention to provide a new therapeutic approach effective also in tumor models characterized by considerable aggressiveness, as well as in diseases with autoimmune features, in the treatment of patients undergoing organ or tissue transplant and in the treatment of hemophilic arthropathy.

BRIEF DESCRIPTION OF THE FIGURES

FIG. 1: SEQ 2
FIG. 11: photomicrographs of the control culture and treated with anti-EPOR at 144 h from the treatment.

SUMMARY OF THE INVENTION

Figure 2:
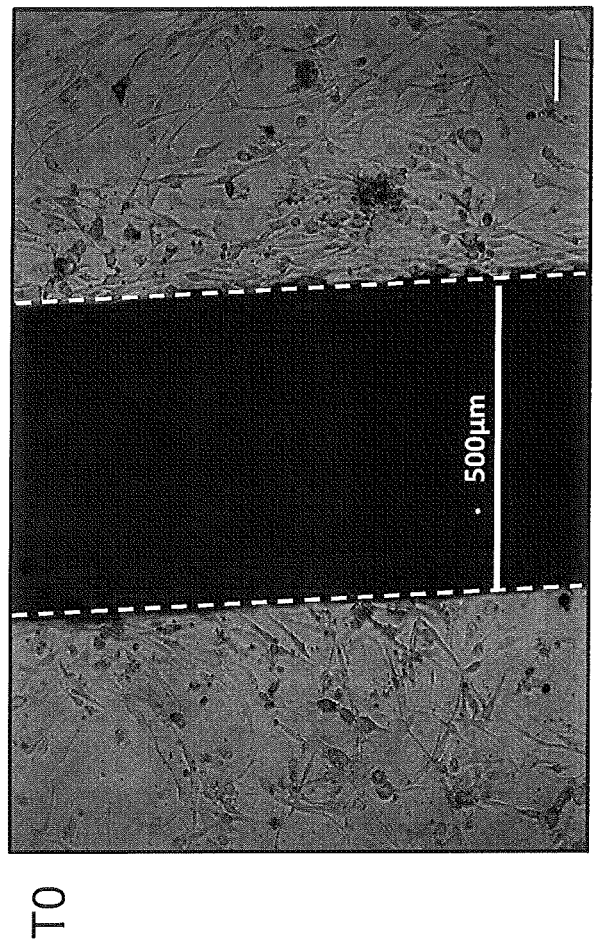
FIG. 2: photomicrograph of the culture at time 0.
Figure 3:
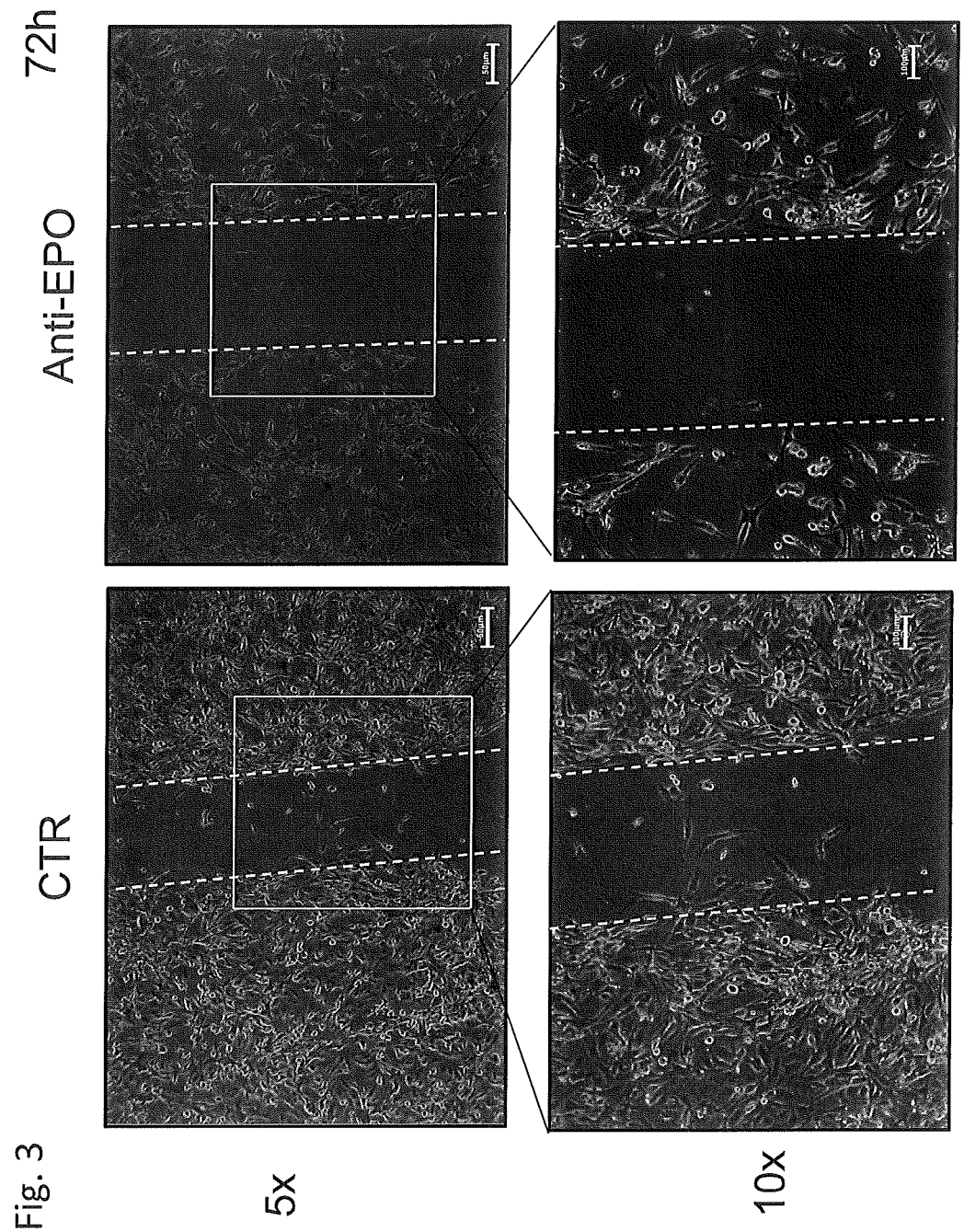
FIG. 3: photomicrographs of the control culture and treated with anti-EPO at 72 h from the treatment.
Figure 4:
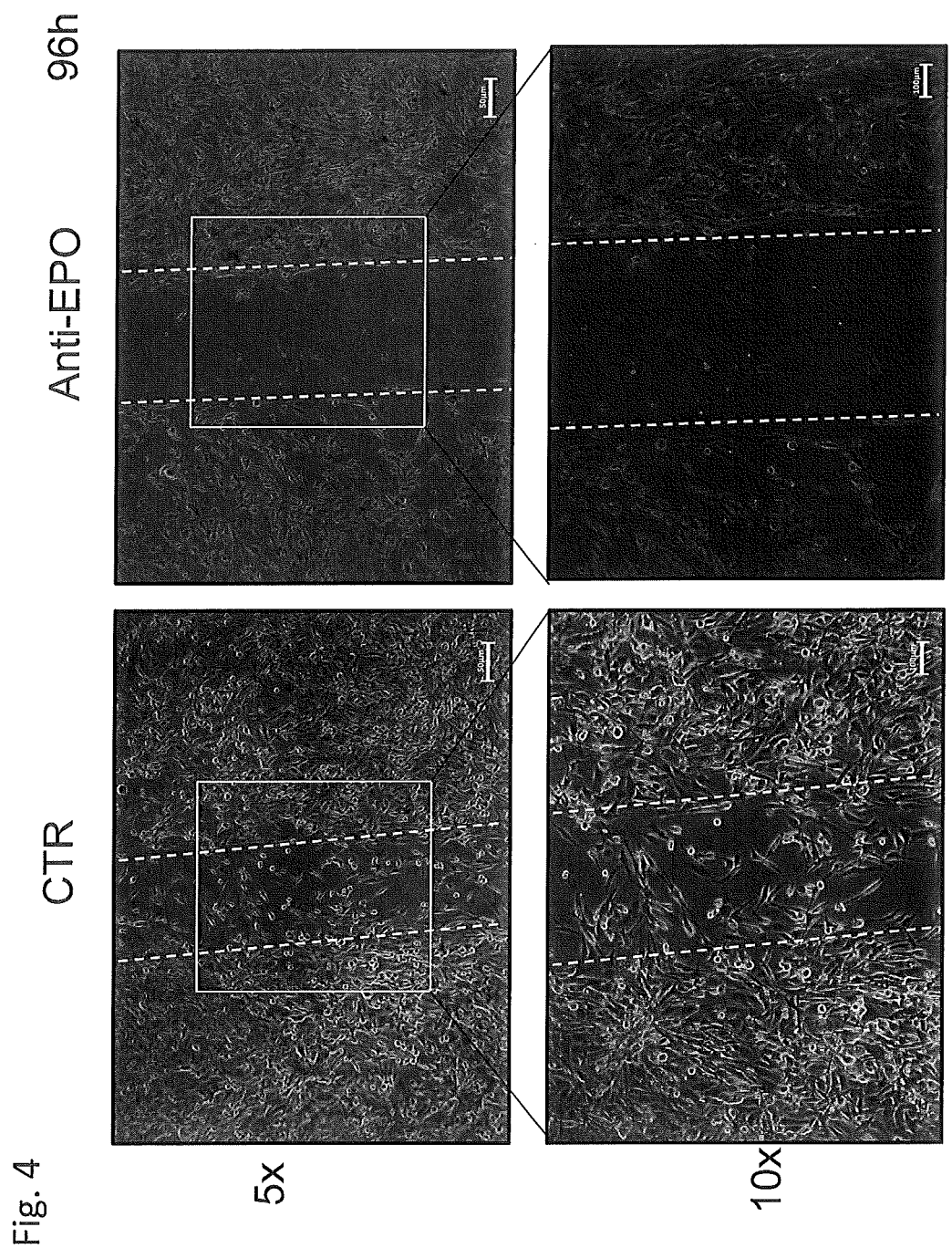
FIG. 4: photomicrographs of the control culture and treated with anti-EPO at 96 h from the treatment.
Figure 5:
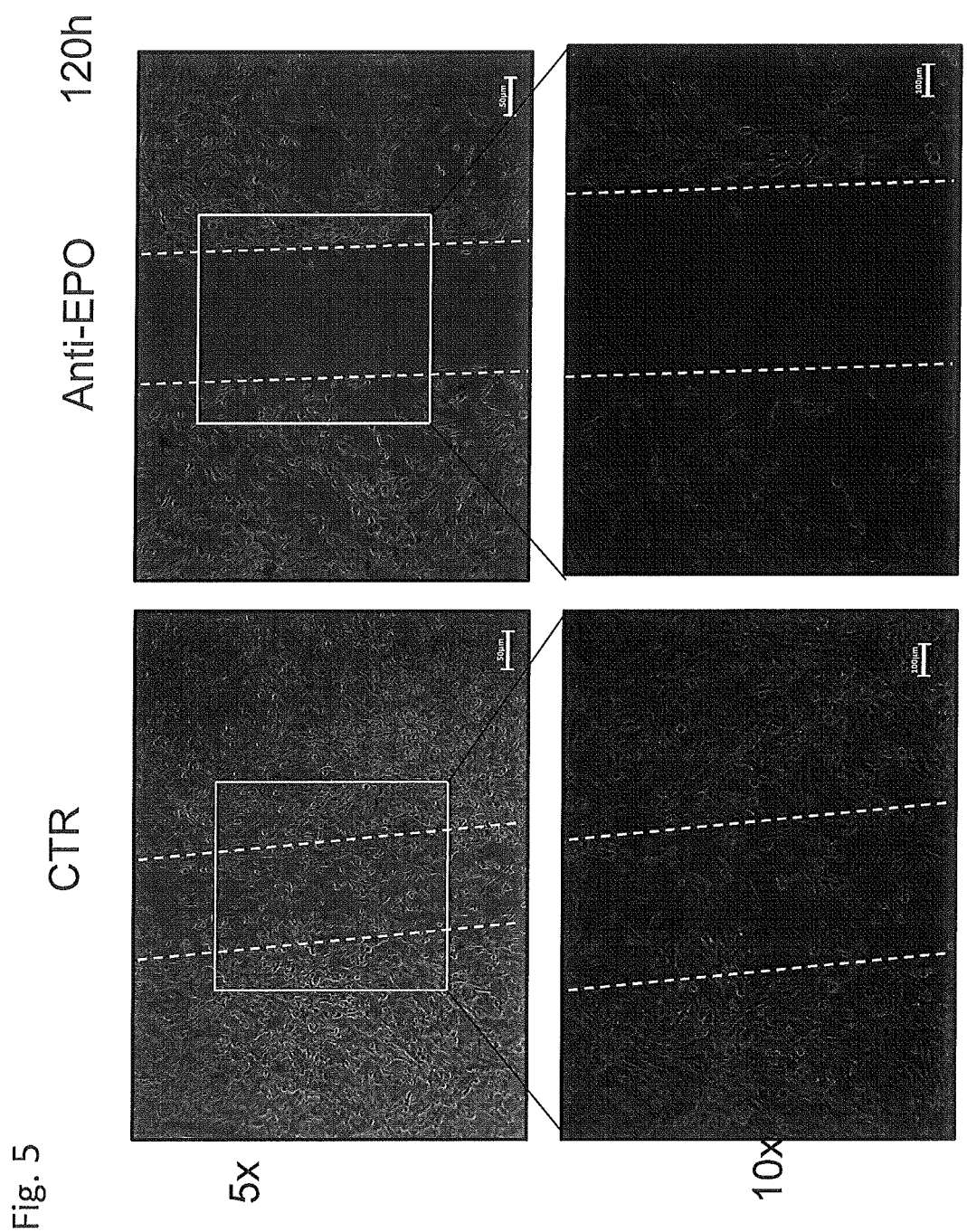
FIG. 5: photomicrographs of the control culture and treated with anti- EPO at 120 h from the treatment.
Figure 6:
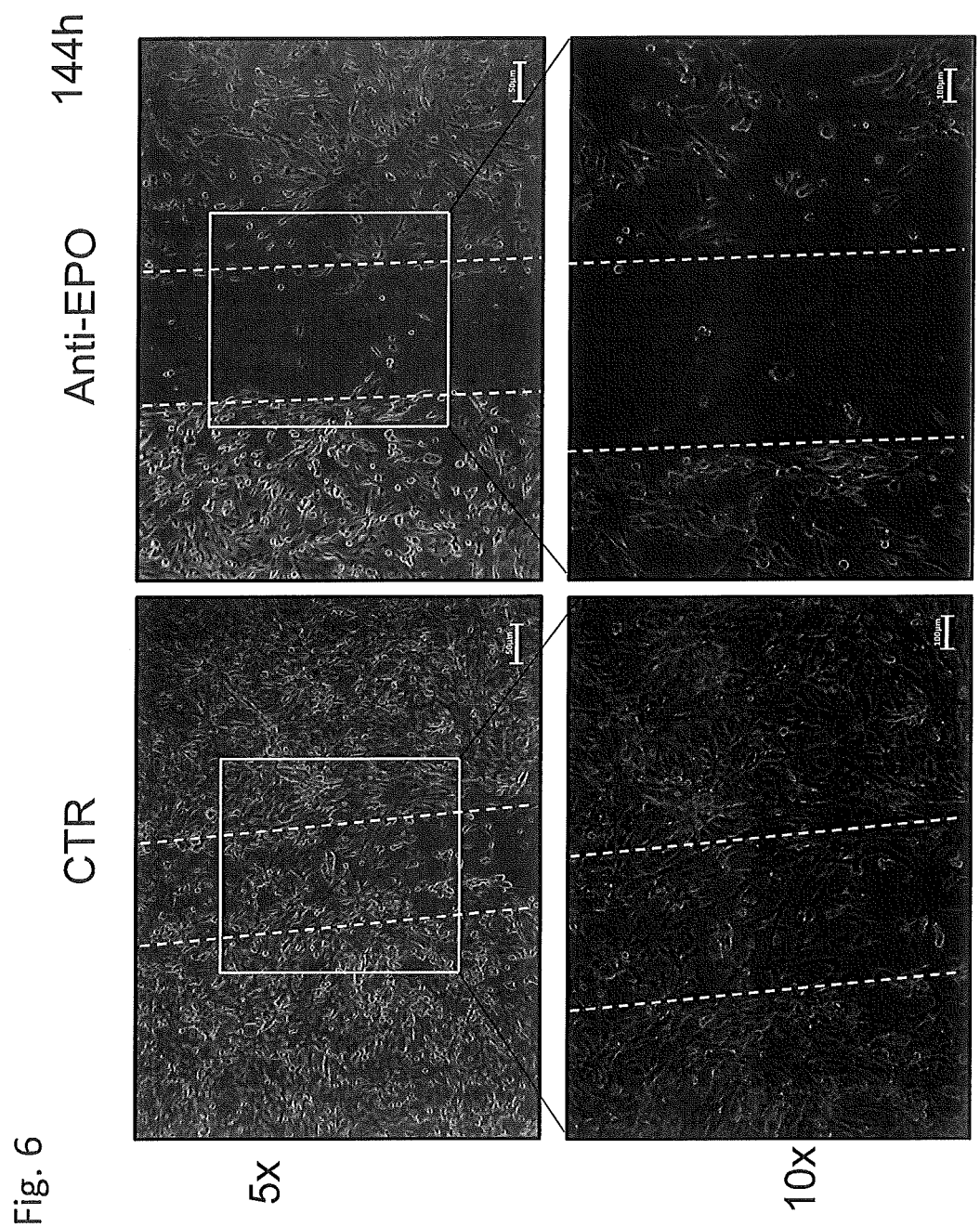
FIG. 6: photomicrographs of the control culture and treated with anti- EPO at 144 h from the treatment.
Figure 7:
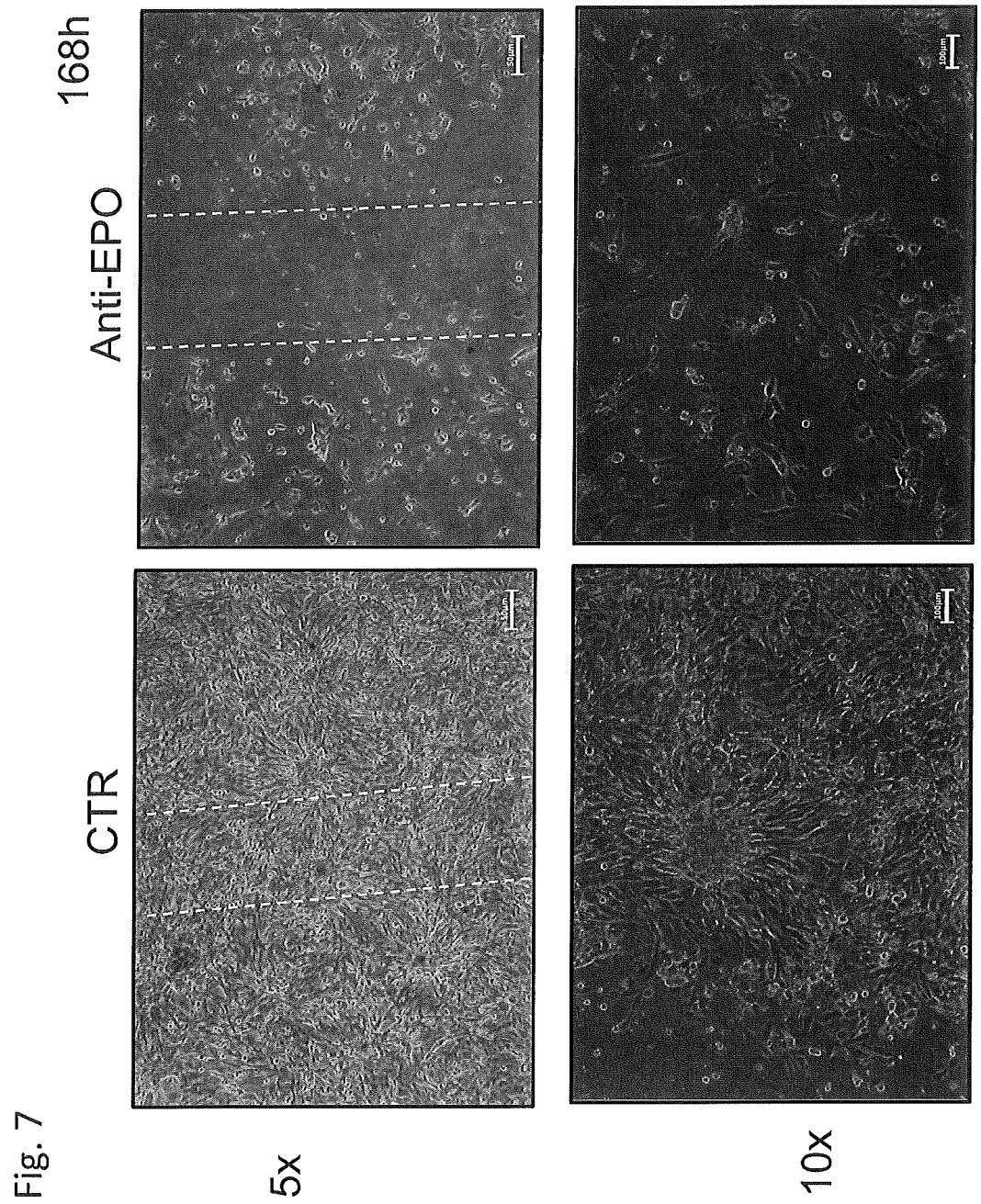
FIG. 7: photomicrographs of the control culture and treated with anti- EPO at 168 h from the treatment.
Figure 8:
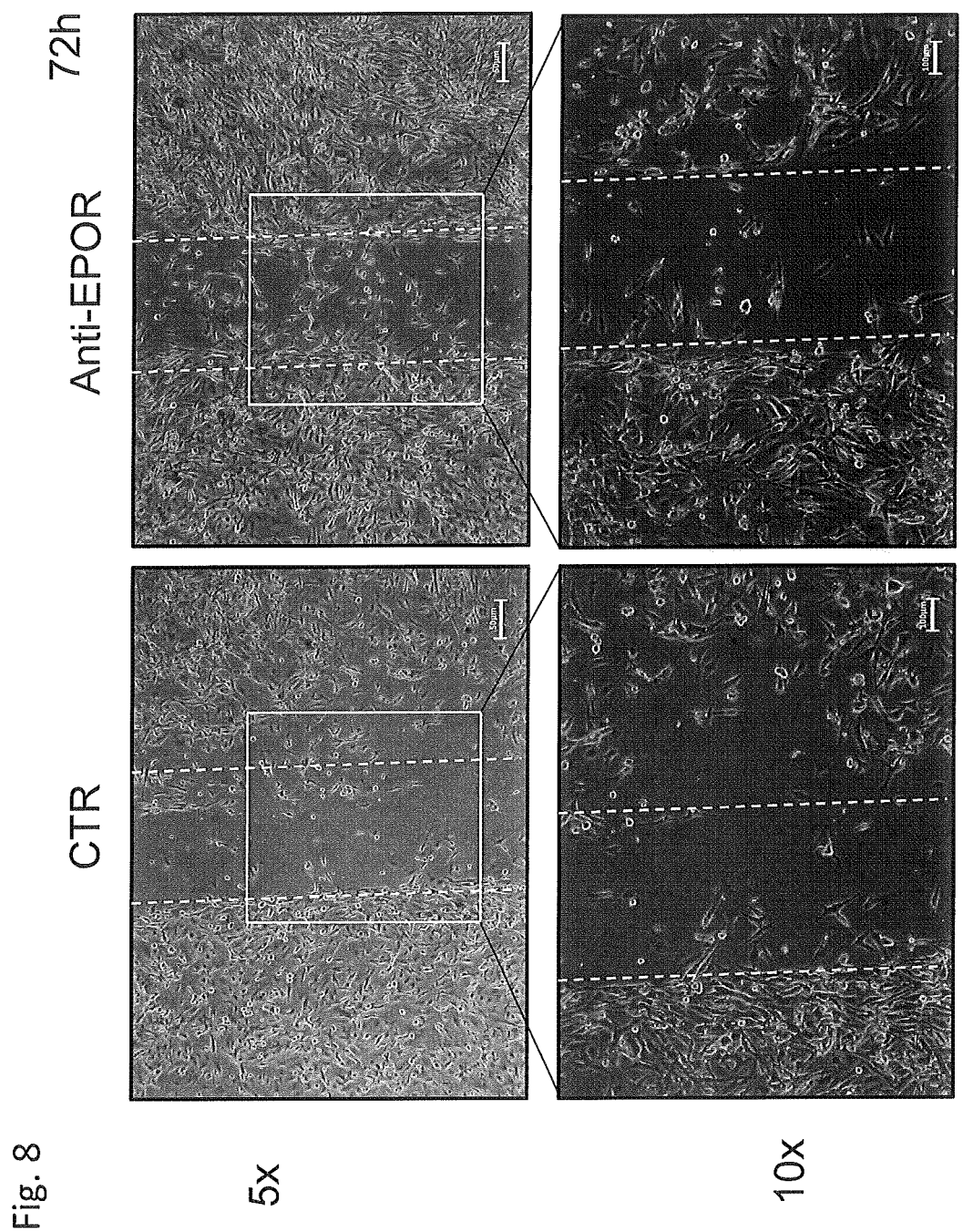
FIG. 8: photomicrographs of the control culture and treated with anti- EPOR at 72 h from the treatment.
Figure 9:
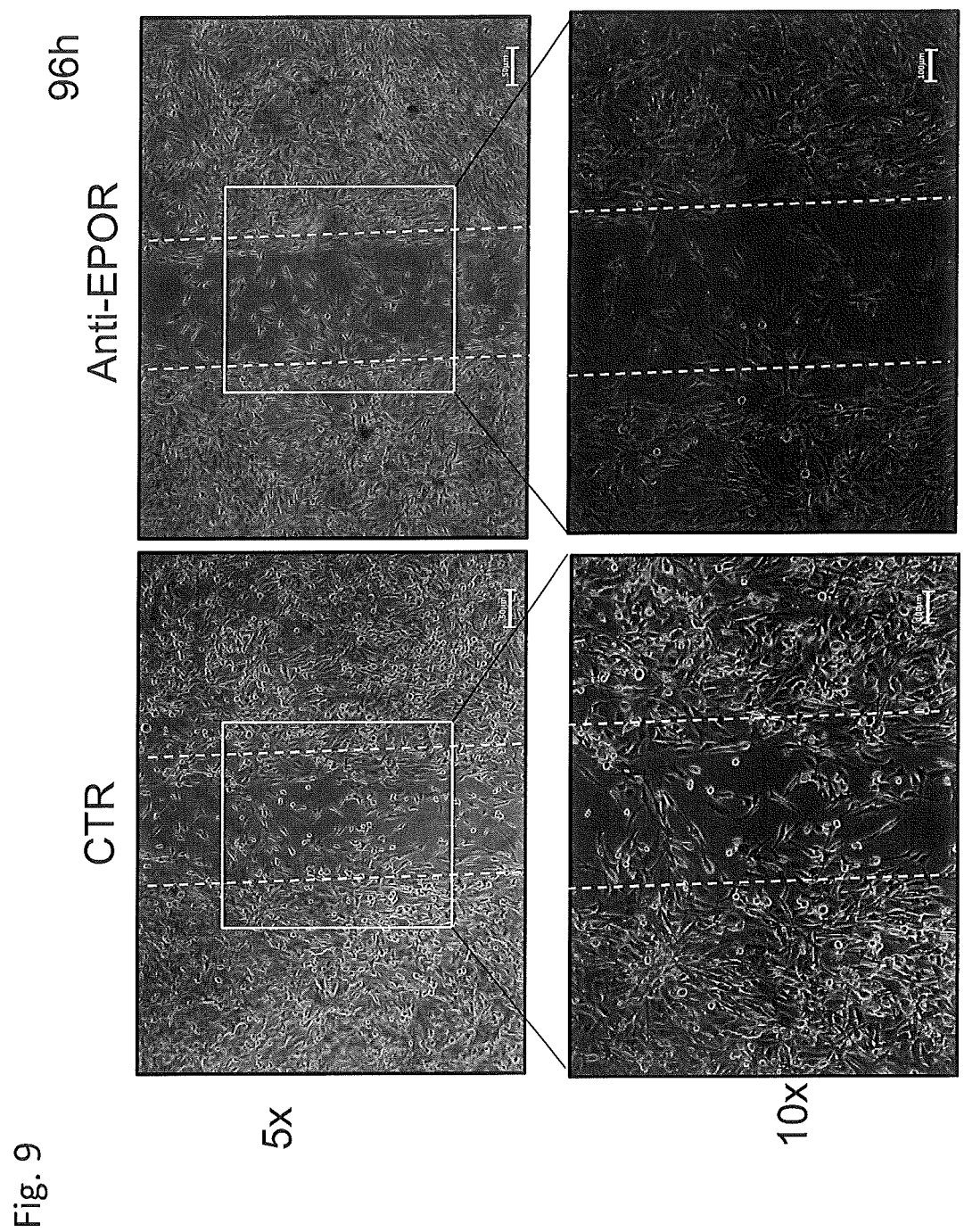
FIG. 9: photomicrographs of the control culture and treated with anti- EPOR at 96 h from the treatment.
Figure 10:
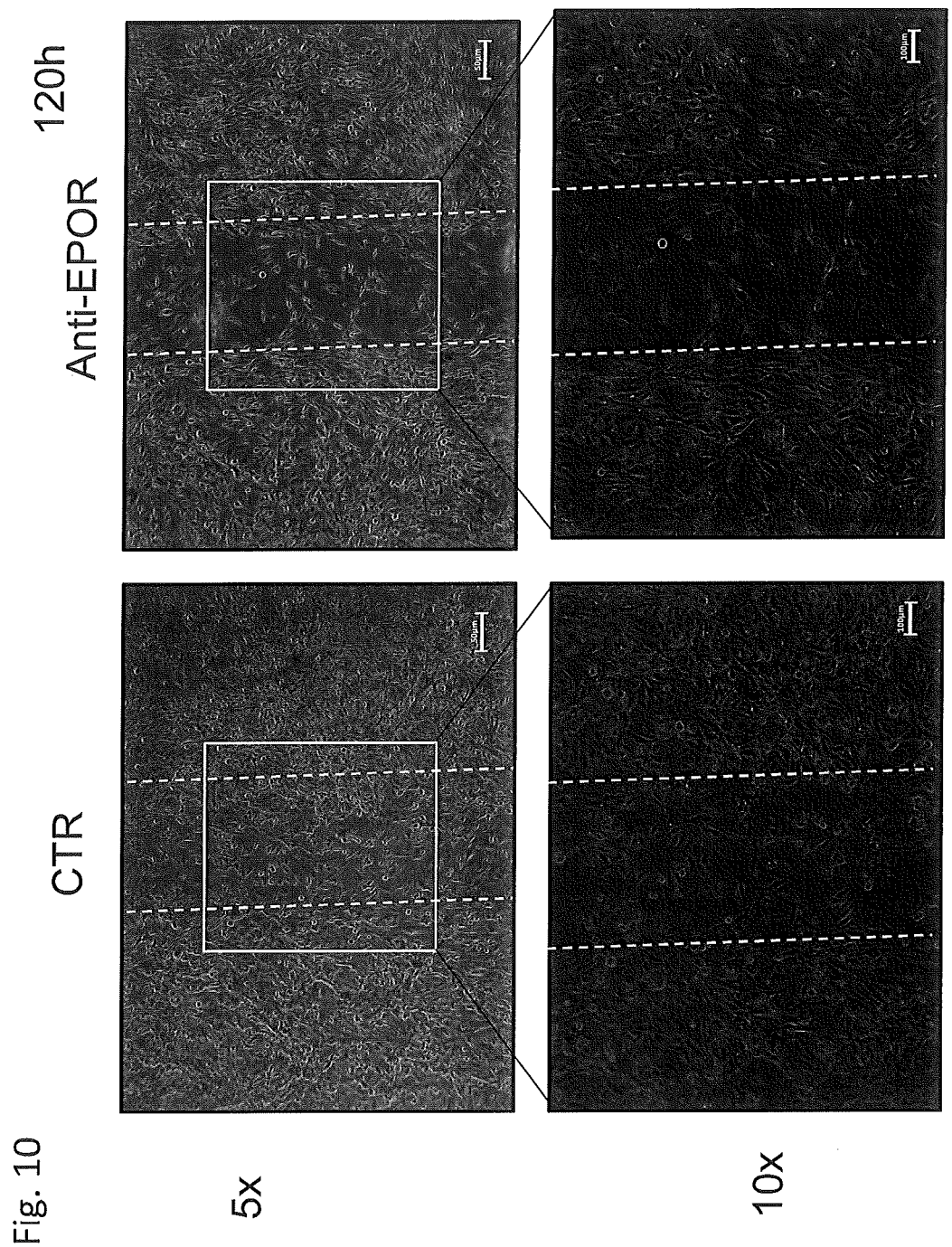
FIG. 10: photomicrographs of the control culture and treated with anti-EPOR at 120 h from the treatment.
Figure 12:
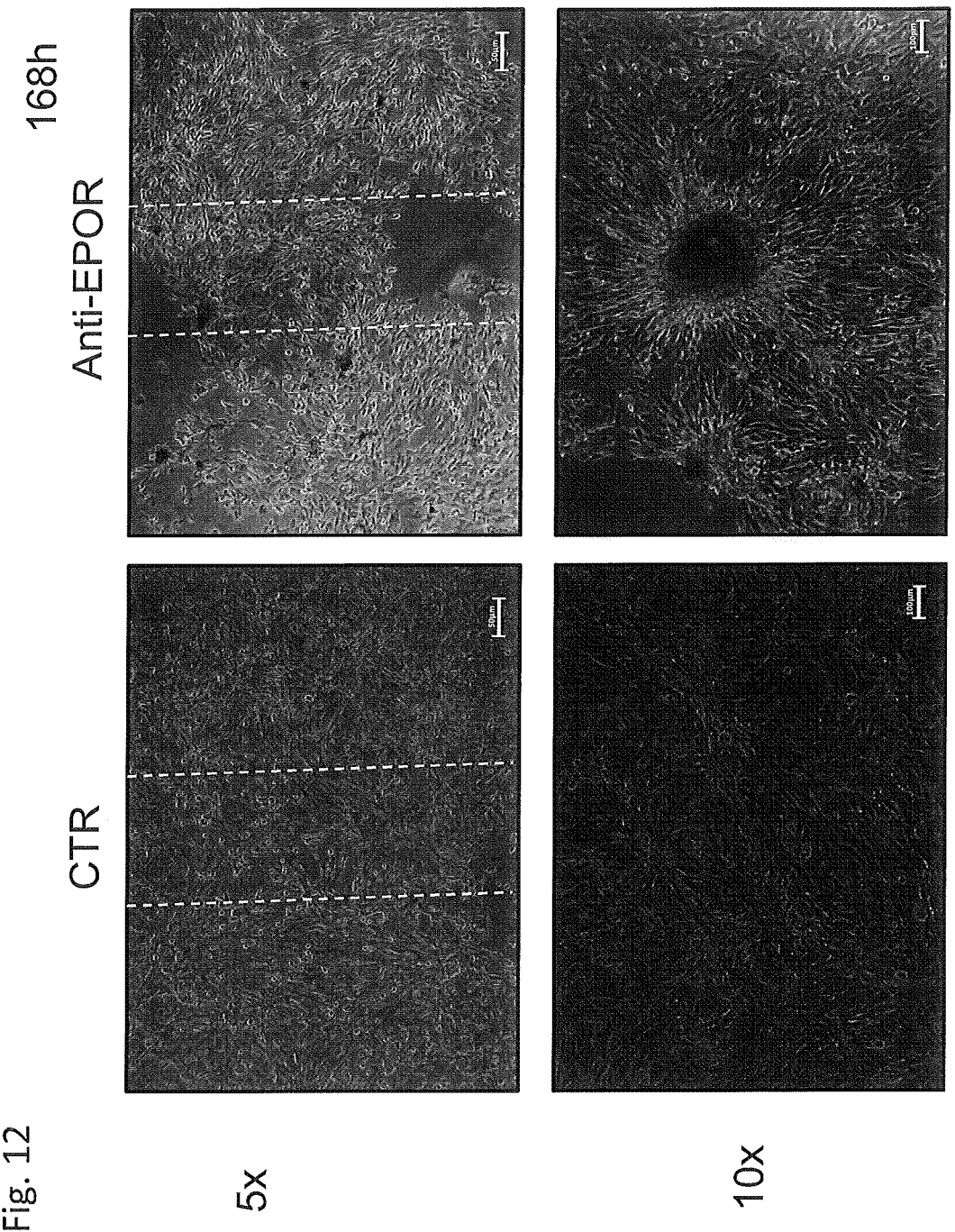
FIG. 12: photomicrographs of the control culture and treated with anti-EPOR at 168 h from the treatment.

The present invention concerns negative functional modulators of erythropoietin (EPO) for use in the treatment of cancers (where they induce the induction of apoptosis in cancer stem cells), in autoimmune diseases, in the treatment of patients undergoing an organ or tissue transplant, in the treatment of hemophilic arthropathy and neurological diseases in which abnormal or excessive activation of the autoimmune system has a pathogenic role. In the present invention, the phrase 'negative functional modulator of EPO' means a molecule, natural or synthetic, capable of direct or indirect interaction with EPO and/or direct or indirect interaction with the receptor of EPO, and/or direct or indirect interaction with one of the mediators of the signal transduction cascade that involves EPO, and/or direct or indirect interaction with the biosynthetic pathway of EPO and/or the anti-EPO receptor (EPOR), wherein said interactions have resulted in a decrease in the levels of EPO, rather than a decrease in the stimulation of the signal transduction cascade in which EPO is involved. In a further embodiment, said negative functional modulators of EPO act on EPO which has undergone post-translational modifications.

In a preferred embodiment, said negative functional modulators are selected from the group comprising molecules able to recognize and bind an amino acid sequence comprising erythropoietin, seizing EPO and preventing its functionality, preferably said molecules are anti-EPO antibodies and their functional analogues. In a further embodiment, said negative functional modulators are anti-EPOR antibodies, preferably anti-EPOR antibodies that recognize a C-terminal cytoplasmic portion of the receptor for EPO blocking its functionality. Alternatively, said modulators are selected from the group comprising siRNA, shRNA, aptamers, RNA and DNA decoy that inhibit the expression of the gene encoding EPO or EPOR.

In a preferred embodiment, said negative functional modulator is a monoclonal or polyclonal anti-EPO antibody. Preferably, said anti-EPO is a polyclonal antibody against AA 28-189 human EPO (SEQ.2), or a monoclonal antibody generated against an epitope contained in the sequence AA 28-189 of human EPO (SEQ.2), where EPO is encoded by the human gene sequence SEQ.1:

```
SEQ. 1:
   1 cccggagccg gaccggggcc accgcgcccg ctctgctccg acaccgcgcc ccctggacag
  61 ccgccctctc ctccaggccc gtggggctgg ccctgcaccg ccgagcttcc cgggatgagg
 121 gcccccggtg tggtcacccg gcgcgcccca ggtcgctgag ggacccccggc caggcgcgga
 181 gatggggggtg cacggtgagt actcgcgggc tgggcgctcc cgcccgcccg ggtccctgtt
 241 tgagcgggga tttagcgccc cggctattgg ccaggaggtg gctgggttca aggaccggcg
 301 acttgtcaag gaccccggaa gggggagggg ggtggggcag cctccacgtg ccagcgggga
 361 cttggggggag tccttgggga tggcaaaaac ctgacctgtg aaggggacac agtttggggg
 421 ttgagggggaa gaaggtttgg gggttctgct gtgccagtgg agaggaagct gataagctga
 481 taacctgggc gctggagcca ccacttatct gccagagggg aagcctctgt cacaccagga
 541 ttgaagtttg gccggagaag tggatgctgg tagctggggg tggggtgtgc acacggcagc
 601 aggattgaat gaaggccagg gaggcagcac ctgagtgctt gcatggttgg ggacaggaag
 661 gacgagctgg ggcagagacg tggggatgaa ggaagctgtc cttccacagc cacccactc
 721 cctccccgcc tgactctcag cctggctatc tgttctagaa tgtcctgcct ggctgtggct
 781 tctcctgtcc ctgctgtcgc tccctctggg cctcccagtc ctgggcgccc caccacgcct
 841 catctgtgac agccgagtcc tggagaggta cctcttggag gccaaggagg ccgagaatat
 901 cacggtgaga ccccttcccc agcacattcc acagaactca cgctcagggc ttcagggaac
 961 tcctcccaga tccaggaacc tggcacttgg tttggggtgg agttgggaag ctagacactg
1021 ccccccctaca taagaataag tctggtggcc ccaaaccata cctggaaact aggcaaggag
1081 caaagccagc agatcctacg gcctgtgggc cagggccaga gccttcaggg acccttgact
1141 ccccgggctg tgtgcatttc agacgggctg tgctgaacac tgcagcttga atgagaatat
1201 cactgtccca gacaccaaag ttaatttcta tgcctggaag aggatggagg tgagttcctt
1261 ttttttttt tttcctttct tttggagaat ctcatttgcg agcctgattt tggatgaaag
```

-continued

```
1321 ggagaatgat cgagggaaag gtaaaatgga gcagcagaga tgaggctgcc tgggcgcaga 1381 ggctcacgtc tataatccca ggctgagatg gccgagatgg gagaattgct tgagccctgg 1441 agtttcagac caacctaggc agcatagtga gatcccccat ctctacaaac atttaaaaaa 1501 attagtcagg tgaggtggtg catggtggta gtcccagata tttggaaggc tgaggcggga 1561 ggatcgcttg agcccaggaa tttgaggctg cagtgagctg tgatcacacc actgcactcc 1621 agcctcagtg acagagtgag gccctgtctc aaaaaagaaa agaaaaaaga aaaataatga 1681 gggctgtatg gaatacattc attattcatt cactcactca ctcactcact cattcattca 1741 ttcattcatt caacaagtct tattgcatac cttctgtttg ctcagcttgg tgcttgggggc 1801 tgctgagggg caggagggag agggtgacat gggtcagctg actcccagag tccactccct 1861 gtaggtcggg cagcaggccg tagaagtctg gcagggcctg gccctgctgt cggaagctgt 1921 cctgcggggc caggccctgt tggtcaactc ttcccagccg tgggagcccc tgcagctgca 1981 tgtggataaa gccgtcagtg gccttcgcag cctcaccact ctgcttcggg ctctgggagc 2041 ccaggtgagt aggagcggac acttctgctt gcccttctg taagaagggg agaagggtct 2101 tgctaaggag tacaggaact gtccgtattc cttcccttc tgtggcactg cagcgacctc 2161 ctgtttctc cttggcagaa ggaagccatc tcccctccag atgcggcctc agctgctcca 2221 ctccgaacaa tcactgctga cactttccgc aaactcttcc gagtctactc caatttcctc 2281 cggggaaagc tgaagctgta cacaggggag gcctgcagga caggggacag atgaccaggt 2341 gtgtccacct gggcatatcc accacctccc tcaccaacat tgcttgtgcc acaccctccc 2401 ccgccactcc tgaaccccgt cgaggggctc tcagctcagc gccagcctgt cccatggaca 2461 ctccagtgcc agcaatgaca tctcaggggc cagaggaact gtccagagag caactctgag 2521 atctaaggat gtcacagggc caacttgagg gcccagagca ggaagcattc agagagcagc 2581 tttaaactca gggacagagc catgctggga agacgcctga gctcactcgg caccctgcaa 2641 aatttgatgc caggacacgc tttggaggcg atttacctgt tttcgcacct accatcaggg 2701 acaggatgac ctggataact taggtggcaa gctgtgactt ctccaggtct cacgggcatg 2761 ggcactccct tggtggcaag agccccttg acaccggggt ggtgggaacc atgaagacag 2821 gatgggggct ggcctctggc tctcatgggg tccaagtttt gtgtattctt caacctcatt 2881 gacaagaact gaaaccacca a
```

Said amino acid portion is the following:
SEQ. 2:

```
  28 app rlicdsrvle rylleakeae nittgcaehc 61 slnenitvpd tkvnfyawkr mevgqqavev wqglallsea vlrgqallvn ssqpweplql 121 hvdkavsglr slttllralg aqeaisppda asaaplrtit adtfrklfrv ysnflrgklk 181 lytgeacrtg dr
```

The therapeutic effect of the modulators of the invention can also be exerted through the independent action of the negative modulation of EPO or by binding to its receptor, through action on different target cells.

In a further embodiment, the object of the present invention is a peptide or a peptidomimetic.

Forming a further aspect of the present invention are compounds, preferably selected from the group which includes negative functional modulators of EPO, which inhibit the synthesis and/or extracellular release of sphingosine-1-phosphate (S1P) mediated by EPO.

Alternatively, said one or more negative functional modulators of EPO are used in combination with one or more molecules selected from the group including natural or synthetic molecules that act on the receptors of S1P, and/or on the metabolism of S1P directly or indirectly via the inhibition of the synthesis of S1P in favor of increased intracellular ceramide or of the release of S1P itself, or cytotoxic antiblastic molecules known in the industry.

In a further embodiment, said negative functional modulators of EPO, alone or in combination, are formulated in a suitable pharmaceutical formulation. Since the molecule of the present invention shows low toxicity, it can be safely administered alone or as a pharmaceutical formulation as tablets, powder, granules, capsules (including soft capsules), liquid agents, injections, suppositories, or slow-release agents generally used for the production of pharmaceutical preparation, orally or parenterally (topical, rectal, intravenous, subcutaneous, intramuscular, intranasal, intravaginal, through the oral mucosa, pulmonary mucosa or via transocular administration, etc.) or by incorporation into liposomes or through the functional delivery towards targets or specific compartments, for example intracranial, intratumoral, by binding to molecular carriers or in combination with molecules that allow the temporary opening of the blood-brain barrier, (eg mannitol) or other anti-inflammatory, monoclonal antibodies and drugs acting as immunosuppressors.

Whereas the therapeutic target are glioblastoma cells, said combination is formulated in such a way as to facilitate the crossing of the blood-brain barrier. By way of example, known factors such as carriers, such as IL13/1L13R-ApoE are used in said formulation. Alternatively, said compounds are administered in the form of nano-particles or liposomes, or with local or intrathecal treatment, or biodegradable biopolymer wafers loaded with the treatment of interest are implanted directly into the surgical cavity after resection of both primary tumors and tumors that relapse. Alternately, they are administered intranasally, for example in the form of a nasal spray, where the therapeutic targets are autoimmune and non-autoimmune based inflammatory diseases, pathologies derived from organ or tissue transplant, hemophilic arthropathy, storage diseases that cause inflammation and neurological disorders characterized in their pathogenesis by primary and/or secondary inflammation from other causes (Alzheimer's, Parkinson etc.).

Said cancer is selected from the group consisting of: brain astrocytoma, cerebellar astrocytoma, astrocytoma of the pineal gland, oligodendroglioma, pituitary adenoma, craniopharyngioma, sarcoma, glioblastoma multiforme, pituitary adenoma, ependymoma, medulloblastoma, neuroectodermal tumor, neuroblastoma, hypothalamic glioma, breast cancer, lung cancer, colon cancer, cervical cancer, endometrial cancer, uterine cancer, ovarian cancer, esophageal cancer, basal cell cancer, cholangiocarcinoma, cancer of the spleen, osteosarcoma, intraocular melanoma, retinoblastoma, stomach cancer, heart cancer, liver cancer, hypopharyngeal cancer, laryngeal cancer, cancer of the oral cavity, nasal and paranasal cancer, salivary gland cancer, nasopharyngeal cancer, throat cancer, thyroid cancer, pancreatic cancer, kidney cancer, prostate cancer, rectal cancer, testicular cancer, melanoma, mesothelioma, pheochromocytoma, hematological cancers, endometriosis, Crohn's disease.

Preferably, said cancer is a glioblastoma multiforme, II and III grade gliomas (grade II gemistocytic glioma, gliomatosis cerebri, anaplastic glioma) (WHO classification 2007).

Preferably, said cancer is adenocarcinoma of the colon, or lung cancer.

Said autoimmune or non-autoimmune based chronic inflammatory diseases, are preferably selected from the group consisting of ulcerative colitis, multiple sclerosis, osteoarthritis, rheumatoid arthritis, Crohn's disease and neuroinflammation.

The negative functional modulators of EPO are also useful in the treatment of neurological disorders characterized in their pathogenesis by primary neuroinflammation and/or neuroinflammation secondary to other causes, such as: Alzheimer's disease and Parkinson's disease, dementia with Lewy bodies, autoimmune diseases with neurologic involvement, amyotrophic lateral sclerosis, neuromuscular diseases, such as myasthenia gravis.

The negative functional modulators of EPO are also useful in treating hemophilic arthropathy (inflammatory-like disease).

As shown later in the text, the use of anti-EPOR and siRNA EPO, give the partially positive effects of the diseases treated, with respect to polyclonal anti-EPO directed against the amino acid sequence AA. 28-189 of EPO. It can be assumed, therefore, that the target of the invention, is not only to seize and reduce levels of EPO preventing binding to the receptor, but inside the antibody mixture are contained molecules with independent action on the negative modulation to the levels of EPO on other cellular targets, or that EPO modules function as shown in the experiments, not only by binding to the receptor, but acting for example on other pathways, such as the adjustment of the stem cell of the tumor cells, the resistance to apoptosis, hypoxia and the modulation of the synthesis and release of sphingosine-1-phosphate.

A further aspect of the present invention is the provision of a method for screening compounds potentially effective as inhibitors to the release of S1P.

Said method comprises: a) provision of in vitro cells expressing S1P, where said cells consist of a primary culture or are a cell line, preferably said cells are cancer cells, more preferably they are CSCs; b) optionally, exposure of these cells to EPO; c) exposure of the culture to compounds to be tested, alone or in combination; d) evaluation by techniques known to the expert in the field of the levels of SK1 and/or SK2 and total S1P and/or intracellular S1P and/or extracellular S1P and, optionally, by cell viability in said culture at appropriate times after said exposure; e) selection of compounds that decrease the levels of SK1 and/or leave unchanged or increase the levels of SK2 and decrease the levels of S1P and/or intracellular S1P and/or extracellular S1P and, optionally, decrease cell viability. Said method, where it provides the addition of EPO, offers the advantage of identifying compounds that direct their activity on S1P acting on EPO. As demonstrated in the present invention, this offers particular advantages and is of interest from a therapeutic point of view, since it has been demonstrated that the effect of S1P-mediated EPO predominantly strikes the tumor stem cells and is able to induce apoptosis in the same.

In one embodiment, where the culture is exposed to a negative functional modulator of EPO and to a chemotherapeutic, said method shows the effect of sensitization towards the chemotherapeutics exerted by said modulator, as apoptotic cell death is observed following exposure of said culture to a combination of one or more negative functional modulators of EPO and one or more chemotherapeutics, while there is apoptosis following exposure of the same culture to one or more chemotherapeutic agents. Alternatively, said method finds application in predicting the responsiveness of a given subject to a negative functional modulator of EPO. In this embodiment, said cells are cells from a sample of tumor tissue obtained by biopsy from a subject and said compounds are selected from the group comprising at least one negative functional modulator of EPO in accordance with claim 1, where said selection is an indication of the efficacy of said compound in said subject. In this embodiment, said method is adapted as follows: a) a sample of tumor tissue, obtained by biopsy from a subject, is placed in D-PBS 1× (Euroclone, Milan, Italy) supplemented with 1% penicillin/streptomycin (Sigma-Aldrich); b) said tissue is mechanically dissociated and subjected to enzymatic digestion; c) after resuspension in a culture medium, the cells are maintained in humidified incubator, 5% $CO_2$ and 0.1-5% $O_2$ at 37° C.; d) said cells are exposed to treatment with at least one negative functional modulator of EPO in accordance with the present invention; f) at appropriate times, measure, by techniques known to the expert in the field, of the levels of SK1 and/or SK2 and S1P total and/or intracellular S1P and/or extracellular S1P and, optionally, the cell viability in said culture; e) whenever said at least one modulator is predicted to be effective in the subject when the levels of SK1 is decreased and/or the levels of SK2 are unaltered or increased and the levels of S1P and/or intracellular and extracellular S1P are decreased. Preferably, after said mechanical dissociation, the suspension is centrifuged, preferably at 300 g for about 10 minutes. Such enzymatic digestion is carried out preferably with 0.25% Liberase Blendzyme2 (Roche Diagnostics, Indianapolis, USA) in D-PBS for 2 h.

DETAILED DESCRIPTION OF THE INVENTION

The negative functional modulators of EPO, described and claimed in the present invention, have surprisingly been shown to be able to induce apoptosis in cancer stem cells, to inhibit their growth and to lead to a possible induction of their differentiation. In one embodiment, said negative functional modulator is an anti-EPO antibody, EPO is preferably the polyclonal antibody (H-162) (Santa Cruz Biotechnology, Inc.) developed against the EPO amino acid sequence 28-189 of human origin (SEQ. 1). In a further embodiment, said negative functional modulator is a purified specific monoclonal immunoglobulin, contained in the above mixture of anti-EPO polyclonal antibody (H-162) (Santa Cruz Biotechnology, Inc), or is a peptide purified from said mixture of anti-EPO polyclonal antibody (H-162) (Santa Cruz Biotechnology, Inc) by proteolytic cleavage of one or more of the immunoglobulins of the same mixture or a monoclonal antibody generated against an epitope contained in the amino acid sequence 28-189 accordingly. In a further preferred embodiment, said negative functional modulator is the polyclonal antibody EPOR (M-20) (Santa Cruz Biotechnology, Inc.), or a purified specific immunoglobulin, contained in the above mixture of polyclonal antibody anti-EPOR. Alternatively, said negative functional modulator is given by the combination of the anti-EPO antibody and the anti-EPOR antibody.

Surprisingly, negative functional modulators of EPO, such as anti-EPO antibodies and anti-EPOR antibodies, were able to induce apoptosis in human glioblastoma stem cells in vitro. It is well known that glioblastoma is a particularly aggressive tumor and that cells derived from glioblastoma are particularly resistant to toxic stimuli. In particular, the biology and the aggressiveness of glioblastoma, permits the modeling of this condition as an example of cancer in which the stem cells have a hierarchical role in modulating the growth of non-stem cancer cells, (which make up the tumor mass), for example through the release of S1P having paracrine/autocrine action (see Marfia G, et al. autocrine/paracrine sphingosine-1-phosphate fuels and proliferative sternness qualities of glioblastoma stem cells. Glia. 2014 December; 62 (12): 1968-81) and which by their nature are resistant to common chemo-radio therapy treatments, increasing the aggressiveness of the tumor and triggering their own relapse. For the purpose of the present invention, a specific glioblastoma cell line, named SC02 has been selected. SC02 cells have mutations in the p53 gene. Mutations in the p53 gene are known to confer resistance towards apoptotic stimuli, therefore it is particularly difficult to induce apoptosis in SC02 cells. The results obtained with the negative functional modulators of EPO, claimed herein and reported in the examples that follow, show the surprising effectiveness of said modulators particularly because they were obtained in an in vitro model characterized by a strong resistance to apoptotic stimuli. Surprisingly, exposure to an anti-EPO antibody reduces the levels of Sphingosine Kinase 1 (SK1) in stem cells of glioblastoma, SK1 being an enzyme with a predominantly antiapoptotic action involved in the phosphorylation of Sphingosine in position 1 and the subsequent conversion to the active form sphingosine-1-phosphate (S1P). This results in a decreased production and decreased extracellular release of S1P, the levels of which have been surprisingly reduced by approximately 50% following treatment with anti-EPO. The same treatment with anti-EPO has instead left unchanged, or in some cellular models, has led to an increase in the levels of sphingosine kinase 2 (SK2), an enzyme with a predominantly pro-apoptotic role. Treatment with anti-EPO has also increased the levels of ceramide, whose pro-apoptotic and differentation role for stem cells is well established in the state of the art. These studies have been published in: Marfia G, et al. Autocrine/paracrine sphingosine-1-phosphate fuels and proliferative sternness qualities of glioblastoma stem cells. Glia. 2014 December; 62 (12): 1968-81.

The combined treatment carried out on cancer stem cells with the anti-EPO antibody and FTY720 and/or temozolomide showed a superior effect in terms of induction of apoptosis and of blocking tumor growth, compared to the effect measured by anti-EPO, FTY720 and temozolomide tested individually. FTY720, functional agonist for the S1P receptor, is activated following phosphorylation mediated by sphingosine kinase, especially by SK2 and is used in post-transplant immunosuppressive therapy, in multiple sclerosis and also in the treatment of malignancies. Since anti-EPO maintains the levels of sphingosine kinase 2 (SK2) unaltered, or increases the levels of sphingosine kinase 2 (SK2), and reduces instead those of sphingosine kinase 1 (SK1), the combination with anti-EPO and FTY720 is further favored, the latter being administered in the form of a prodrug and activated at the cellular level by SK2. Or the combination with anti-EPO and one or more molecules selected from antagonists of S1P which include FTY720-P, SW-2871, VPC24191, AUY954, SEW2871 (5-[4-phenyl-5-(trifluoromethyl)-2-thienyl]-3-[trifluoromethyl)phenyl]-1,2, 4-oxadiazole), VPC23153, DS-GS-44, VPC01091.

Within the scope of the effects on chronic inflammatory conditions and not on the autoimmune basis, studies have shown that activating microglia with lipopolysaccharide, a potent inflammatory stimulus, there is proliferation and migration of the same, as well as damage to the target cells and synthesis and release of S1P. Treatment with negative modulators of EPO according to the invention, in association with or without FTY720 and its analogues, as shown in the examples that follow, inhibits the proliferation, migration and survival of activated microglia, as well as reducing the levels of S1P products by microglia. These effects are enhanced by the association of two principles. The cells principally involved in the maintenance and amplification of the neuroinflammatory state, through the production of pro-inflammatory molecules such as cytokines and chemokines, are those of microglia. However, prolonged and uncontrolled microglial activation is harmful for neurons and thus the inhibition of the prolonged neuroinflammatory state constitutes today a target of strategies to limit neuronal damage. To test this hypothesis, an in vitro model in which cells N9, (a cell line of immortalized murine microglia), cultured in the presence of lipopolysaccharide, was used as a potent inflammatory stimulus and subjected to treatment with polyclonal anti-EPO; EPOsiRNA; anti-EPO+FTY720 to study the effects on the survival, migration and proliferation of activated microglia.

In the context of the effects on inflammatory-like diseases such as haemophillic arthropathy, the isolation studies of endothelial cells from the synovium of patients with haemophilia, for the first time surprisingly demonstrated an increased angiogenesis with reduced stabilization and vessel maturation (tumor-like) at the synovial level, associated with an increased release of VEGF in the culture medium especially when compared to their respective healthy controls. Furthermore, the study of the sphingolipid metabolism of these cells showed a significant increase in intracellular levels of sphingosine-1-phosphate as the main mediator of the neo-angiogenesis and the inflammatory mechanism (Strub G M et al, Adv. Exp. Med. Biol. 2010). The abnormal proliferation and altered maturation of vessels associated with an inflammatory state also manifests itself in other coagulation disorders comprising hemophilia A and B, von Willebrand's disease and angiodysplasia associated therewith. Chronic inflammation is common to this phenotype, to that of cancer stem cells/tumor tissues and other inflammatory diseases such as rheumatoid arthritis. In this sense, the data obtained (inserted in the examples below) show that treatment with "anti-EPO" is able to block pathological synovial endothelial proliferation and reduce the synthesis of the intracellular levels of sphingosine-1-phosphate, increasing instead ceramide levels, having pro-apoptotic and differentiative, and also abolishing the initial inflammatory stimulus. The negative modulators of EPO according to the present invention can therefore be used for direct intra-articular treatment in the form of a gel or suspension, in association or not with "coagulation factors and their derivatives" and FTY720 if necessary and/or negative modulators of the sphingosine-1-phosphate pathway and/or inhibitors of VEGF and receptors. Alternatively, it is possible to use the negative modulators of EPO for topical or systemic application, as well as in the form of microparticles, liposomes etc.

Alternatively, the administration may be achieved through the use of all those technologies currently related to gene therapy, or the use of vectors for the introduction of nucleic acids into cells of the patient. Such administration can be effected at a systemic level, then by infusion, or at a local level, with the administration of vectors directly into the site of the lesion, tumor, synovial, cerebral etc.

A further object of the present invention is a pharmaceutical composition for use in the treatment of malignancies, in the therapy of autoimmune and non-autoimmune based chronic inflammatory diseases, in the treatment of patients undergoing an organ or tissue transplant, in the treatment of hemophilic arthropathy and in the treatment of neurological disorders in which neuroinflammation has a role in the pathogenesis, that comprises a negative functional modulator of EPO according to the present invention in therapeutically effective concentrations and pharmaceutically acceptable excipients. Preferably, said composition further comprises a therapeutically effective amount of one or more natural or synthetic molecules that act on the receptors of S1P, and/or on the metabolism of S1P directly or indirectly, and/or anticancer cytotoxic molecules and/or antiviral and/or anti-angiogenic. Even more preferably, said molecule which acts on the receptors of S1P, and/or on the metabolism of S1P directly or indirectly, is FTY720 or its analogues. Preferably, said anticancer cytotoxic molecule and/or antiviral and/or anti-angiogenic is selected in the group comprising: paclitaxel, taxol, cycloheximide, carboplatin, chlorambucil, cisplatin, colchicine, cyclophosphamide, daunorubicin, dactinomycin, diethylstilbestrol, doxorubicin, etoposide, 5-fluorouracil, floxuridine, melphalan, methotrexate, mitomycin, 6-mercaptopurine, teniposide, 6-thioguanine, vincristine and/or vinblastine, fotemustine, carmustine, irinotecan systemically or by carmustine adsorbed biopolymer wafers for locoregional therapy, temozolomide, tamoxifen, valganciclovir, ganciclovir, acyclovir, anti-VEGF, anti-VEGFR, anti-HER2/neu, anti-EGFR, gefitinib, bevacizumab, ranibizumab, vatalanib, Cediranib, Sorafenib, Sunitinib, Motesanib, Axitinib.

Migration, Invasiveness Test In Vitro

SC02 cells are plated in a double chamber well (Boyden Chamber) separated by a silicone septum. Once the cell confluence is reached, the septum is removed, and the time it takes for the cells to invade the empty space left after the removal of the septum is measured. Cells occupying this space are counted for the necessary analysis.

The Cells were Exposed to the Following Treatments:
Anti-EPO antibody (H-162) (the culture medium is replaced at time 0 with fresh culture medium containing anti-EPO antibody).
Anti Erythropoietin Receptor antibody (EPOR; the culture medium is replaced at time 0 with fresh culture medium containing anti-EPOR antibody).
Control (replacement of the culture medium at time 0 with fresh culture medium).

It is noted that the anti-EPO antibody (H-162) is able to reset the number of infiltrating cells. The anti-EPOR antibody is also capable, albeit less effectively, to reduce the migration. The analysis of cell viability shows that, at 72 hours after treatment with anti-EPO, only about 2% of the cells initially plated are still alive. Evaluating the expression level of the factors involved in the apoptotic cascade, in addition to analysis by flow cytometry after staining with Annexin V and Propidium Iodide, it was demonstrated that treatment with anti-EPO antibody was able to induce cell death by activation of the apoptotic pathway.

The induction of apoptosis in cells SC02 described herein, cells particularly resistant to apoptosis for the reasons described above, shows that anti-EPO is surprisingly effective in activating the apoptotic pathway. Anti-EPO, a peptide that binds EPO and/or a negative functional modulator of the expression levels of EPO have proved to be effective molecules for use in the treatment of malignancies, in particular in the treatment of glioblastoma.

Levels of Expression and Release of Sphingosine-1-Phosphate.

The treatment of different cell types, tumors and non-tumors with negative functional modulators of EPO led to decreased levels of SK1 expression. The levels of SK2 on the other hand, remain unchanged and, in some cases, are increased following the same treatment. The levels of intracellular and extracellular S1P were constantly decreased following treatment with functional negative modulators of EPO.

EXAMPLES

Example 1

Test of Migration, Invasiveness In Vitro

SC02 cells are plated in a Boyden Chamber separated by a insert silicone in a growth medium called SCM (Stem Cell Medium) selective for the growth of cancer stem cells. The formulation of the above-mentioned medium is as follows: DMEM/F-12 at a concentration of 1×, solution of antibiotics/antimycotics in the concentration ratio of 1/100, apotransferrin at a concentration of 48.82 µg/mL, Insulin at a concentration of 11.5 µg/mL, selenium at a concentration of 2.37 ng/mL, Progesterone at a concentration of 2.88 ng/mL, Putrescine at a concentration of 48.25 µg/mL, Glucose (33 mM), epidermal growth factor (EGF) at a concentration of 10 ng/mL, basic fibroblast growth factor (bFGF) at a concentration of 5 ng/mL, L-glutamine at a concentration of 292 µg/mL, sodium bicarbonate (7.5% weight/vol) (60 µg/ml), Hepes (4-2-hydroxyethyl-1-piperazinyl-ethanesulfonic acid) at a concentration of 1M, heparin at a concentration of 2 µg/mL, bovine serum albumin (BSA) at a concentration of 1.95 µg/mL and 10 incubated to 37° C., 5% $CO_2$, 0.1-5% $O_2$. Once the cell confluence has been reached, the septum is removed, and the time it takes for the cells to invade the empty space left after the removal of the septum is measured. Cells occupying this space are counted for the necessary analysis. The cells are exposed to the following treatments:—anti-EPO antibody (H-162) (at time 0, replacing the culture medium with culture medium containing 3 µg/ml of anti-EPO polyclonal antibody (H-162) against AA 28-189 of the human EPO).

Anti-EPOR (M-20) (at time 0, replacing the culture medium with culture medium containing 3 µg/ml of anti-EPOR, polyclonal antibody against a C-terminal cytoplasmic domain of human EPOR)

Control (at time 0, replacement of the culture medium).

In FIG. 2 a photomicrograph of the culture at time 0 is shown. FIGS. 3 to 7 show photomicrographs at successive times, from 72 to 168 h, in the control sample and in the sample treated with anti-EPO. The photographs show the expected migration in the control cells, while the culture treated with anti-EPO not only does migration not occur, but the cell culture appears to spoil. FIGS. 8 to 12 show photomicrographs at the same times, from 72 to 168 h, in the control sample and in the sample treated with anti-EPOR. Treatment with anti-EPOR is not able to block the migration, the blockage is only partial and cell viability appears good in any case.

Figure 13:
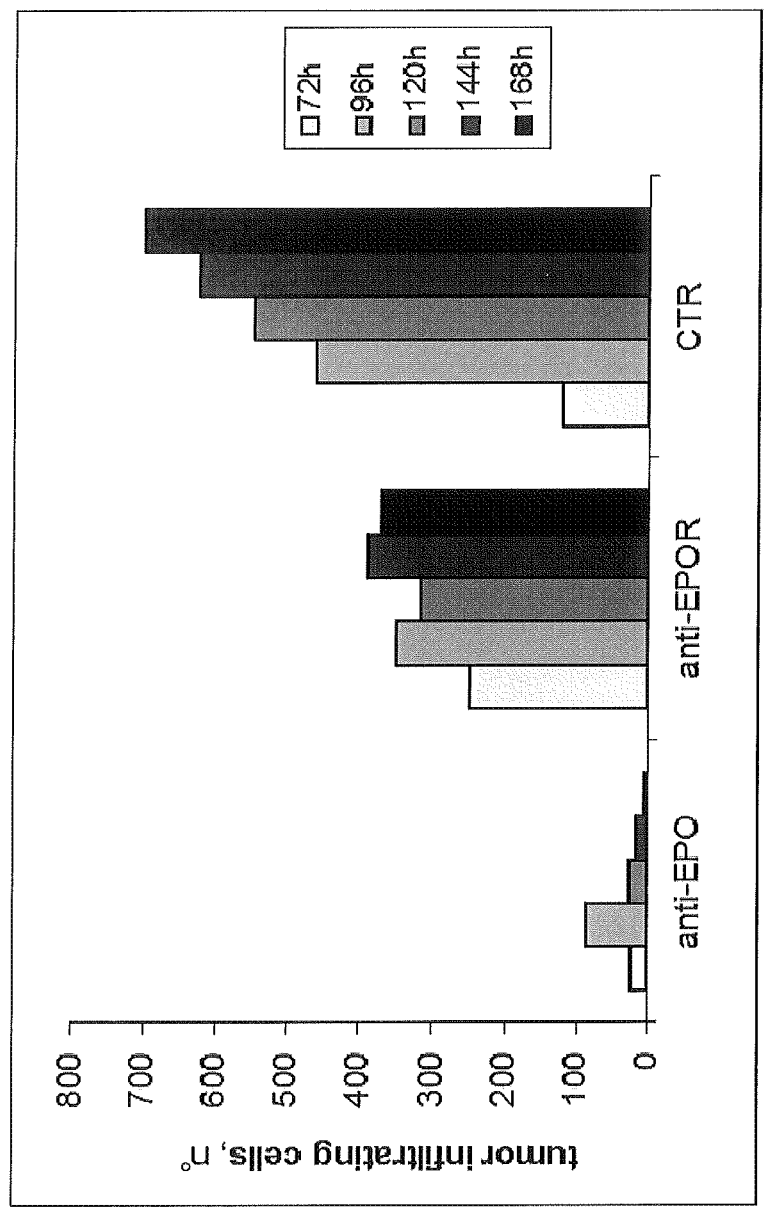
FIG. 13: count of the number of infiltrating cells.

The observation was quantified by counting the number of infiltrating cells at different times. The results, shown in the graph in FIG. 13, confirm that the non-treated culture after a time has a cell migration such as to reach confluence, while treatment with anti-EPO completely blocks cell migration. Exposing the same culture to anti- EPOR, the blockage is only partial.

Example 2

Cell Viability

Figure 14:
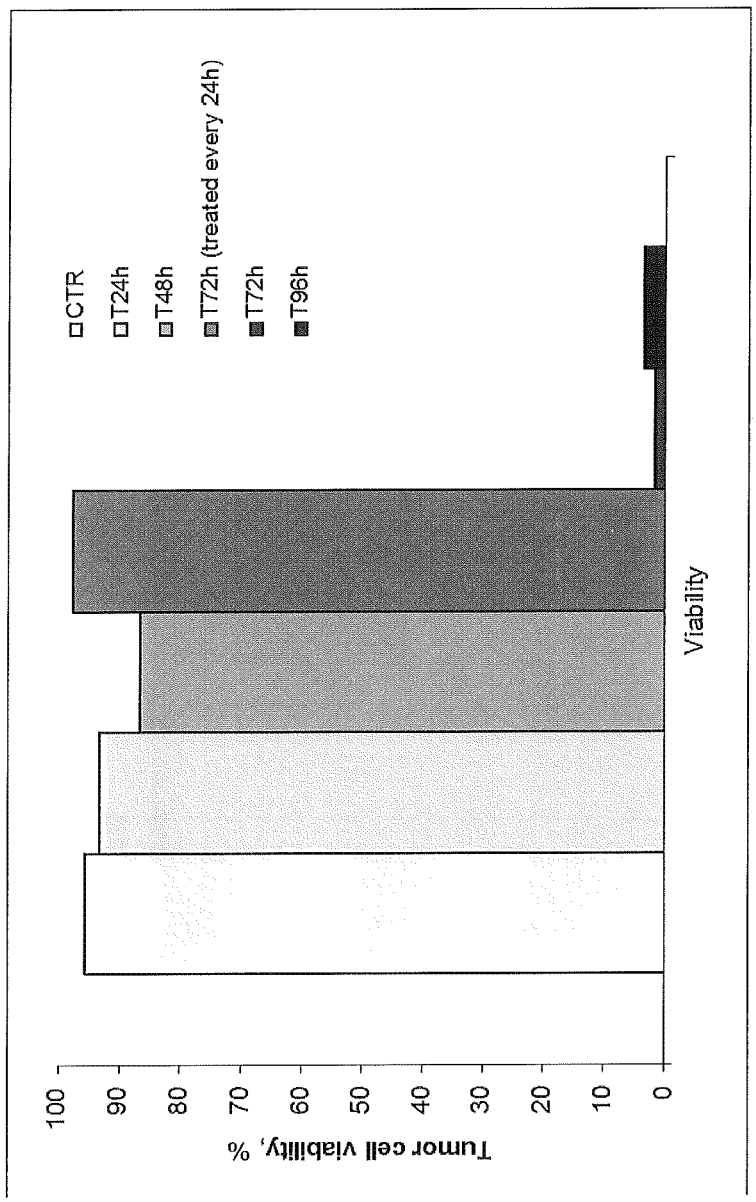
FIG. 14: cell viability count.

SC02 cells were plated in the SCM medium as previously reported and exposed to the following treatments:
Anti-EPO (H-162) (at time 0, replacing the culture medium with culture medium containing 3 µg/ml of anti-EPO, polyclonal antibody against AA 28-189 of human EPO).
Anti-EPOR (M-20) (at time 0, replacing the culture medium with culture medium containing 10 µg/ml of anti- EPOR, polyclonal antibody against a C-terminal cytoplasmic domain of human EPOR).
Control (at time 0, replacement of the culture medium).
The cells were counted with trypan blue to check cell viability every 24 hours after exposure to anti-EPO. The results are reported in the graph in FIG. 14. From 72 hours after the treatment, the cell viability is practically zero.

Example 3

Analysis of the Cell Cycle

Figure 15:
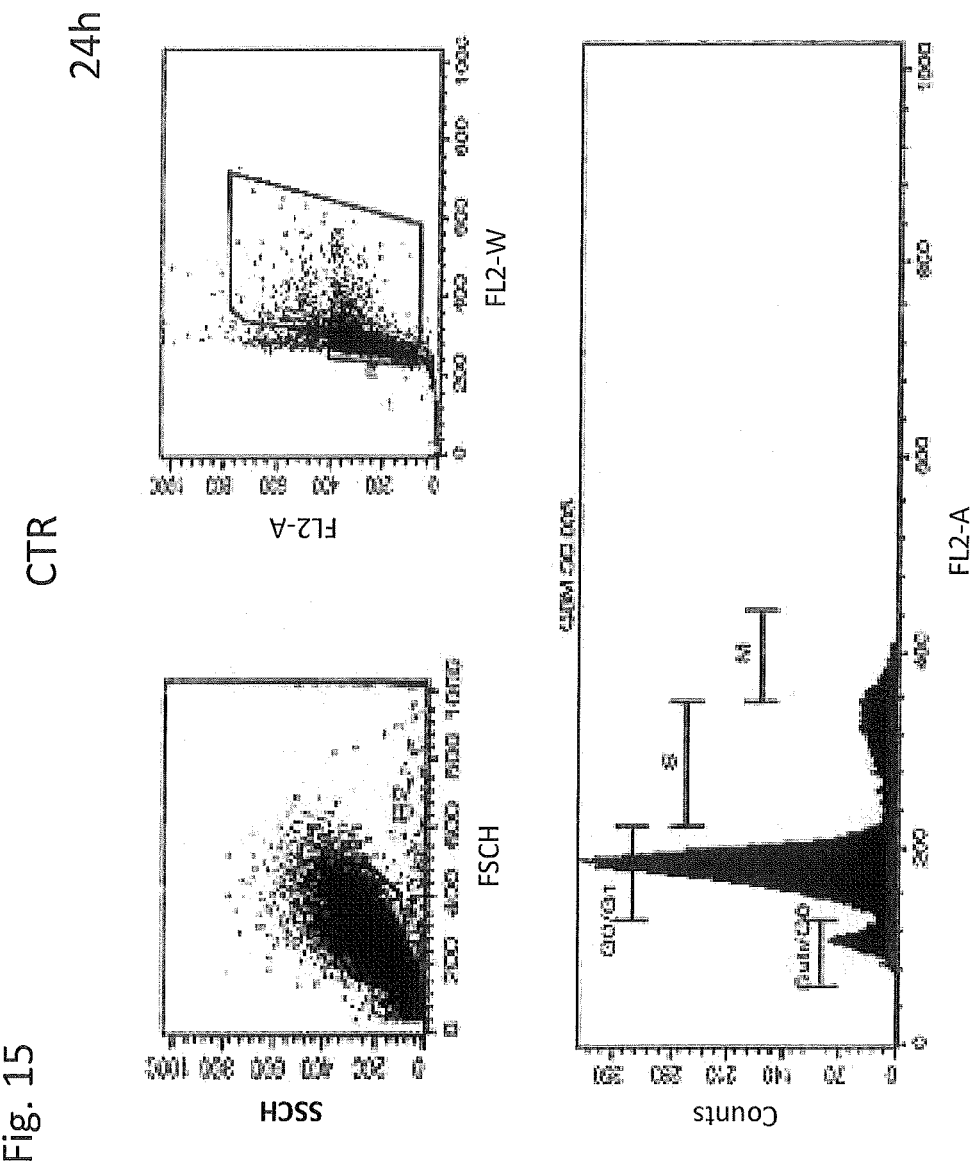
FIG. 15: flow cytometry analysis of cell cycle performed on control cells.
Figure 16:
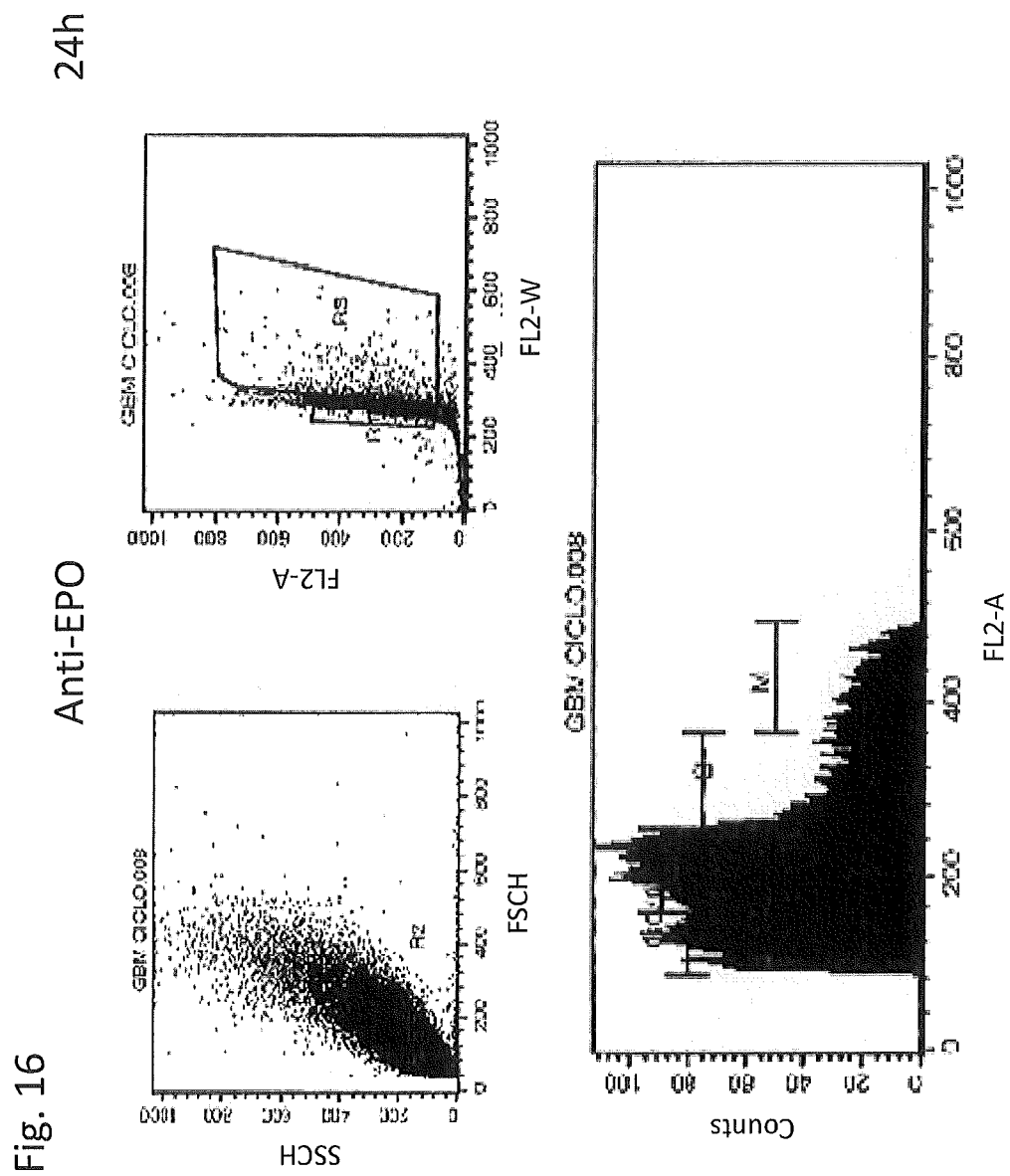
FIG. 16: flow cytometry analysis of cell cycle performed on cells exposed for 24 hours to anti EPO.

The effect on the cell cycle of cell culture treated with anti-EPO antibody (H-162) was estimated by flow cytometry. SC02 cells, 24 hours after plating in SCM medium show the expected profile (FIG. 15). Exposure for 24 hours to anti-EPO leads to the desynchronization of all phases of the cell cycle, resulting in a drastic and early reduction of cell proliferation in the following hours, causing an arrest of cell growth. (FIG. 16).

Example 4

Analysis of the Expression Levels of Factors Involved in Apoptosis

In order to assess the type of cell death induced by treatment with anti-EPO antibody, the expression levels of key factors of the apoptotic cascade were evaluated by Western blot. The expression levels of: Caspase 9, Caspase 3, the final effector of apoptosis, Bax, pro-apoptotic molecule and Bc12, and the anti-apoptotic molecule were measured in SC02 cells treated or untreated with anti-EPO (H-162).

Figure 17:
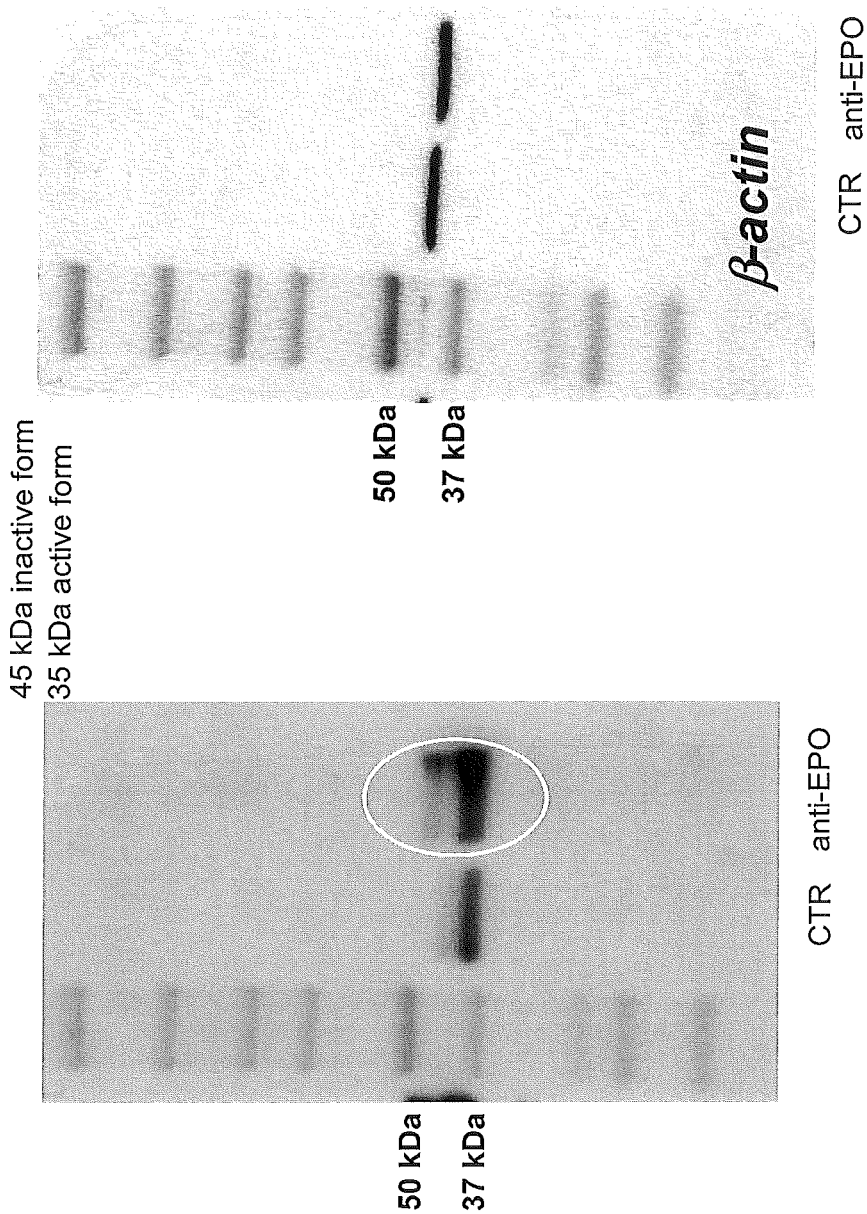
FIG. 17: Western Blot with anti-Caspase-9 antibody and loading control using Beta actin.
Figure 18:
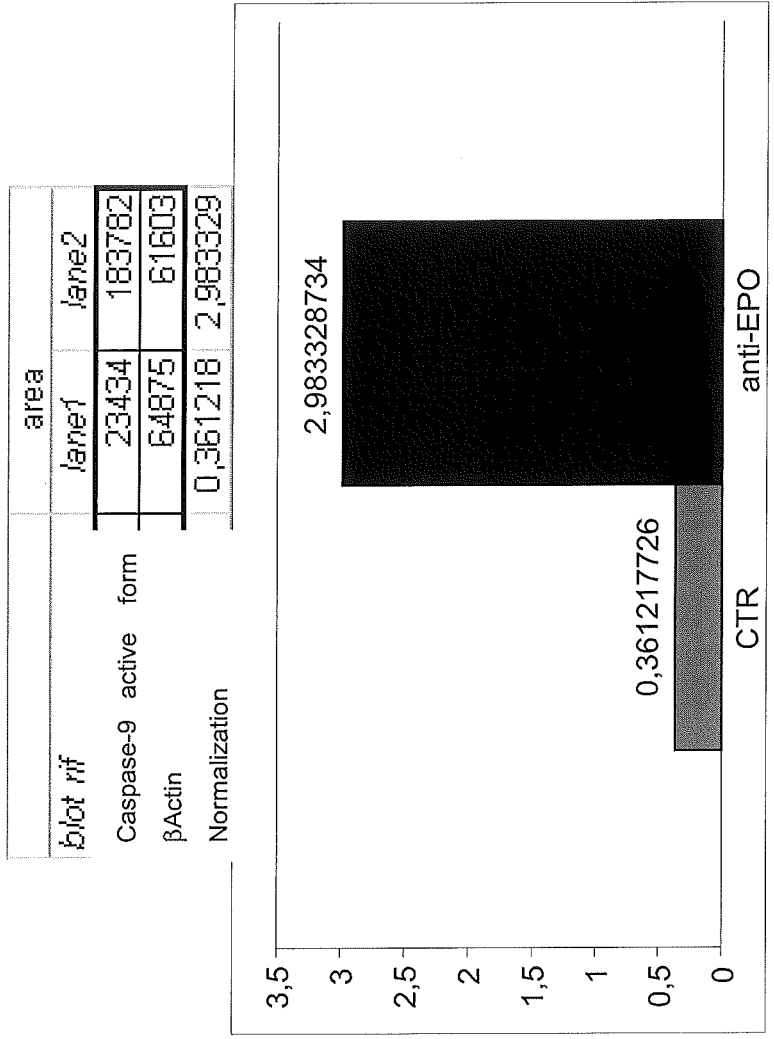
FIG. 18: quantization of the expression levels of Caspase-9.

The levels of beta-actin were used as a normalization factor of the amount of protein loaded. FIG. 17 shows how, in the presence of the treatment with anti-EPO, the expression levels of the active and inactive forms of Caspase 9, have increased. The quantization of the bands and their normalization shows, in FIG. 18, an accumulation of about 8 times the levels of active Caspase 9 in the samples exposed to treatment with anti-EPO compared to the untreated control.

Figure 19:
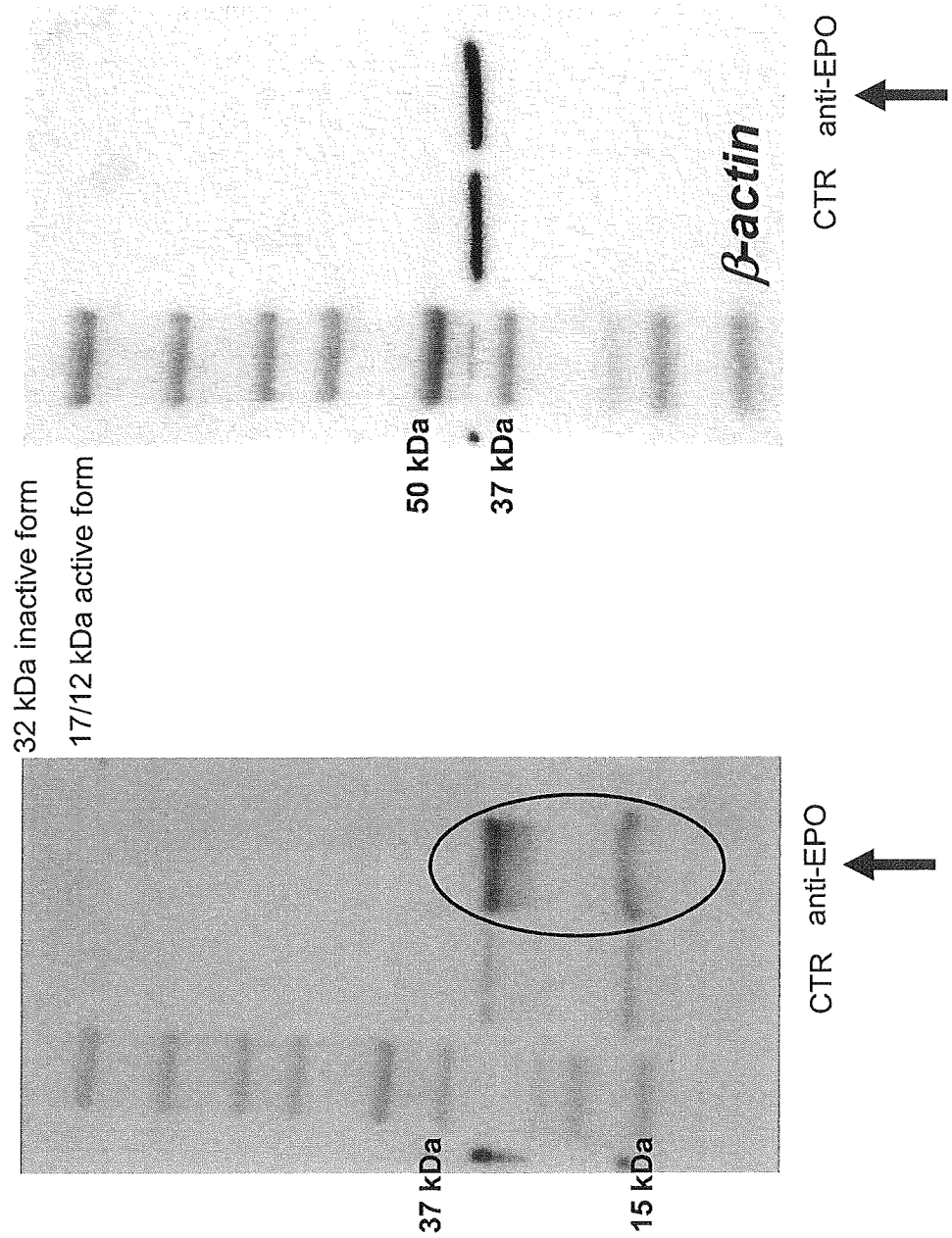
FIG. 19: Western Blot with anti-Caspase 3 antibody and loading control using Beta actin.
Figure 20:
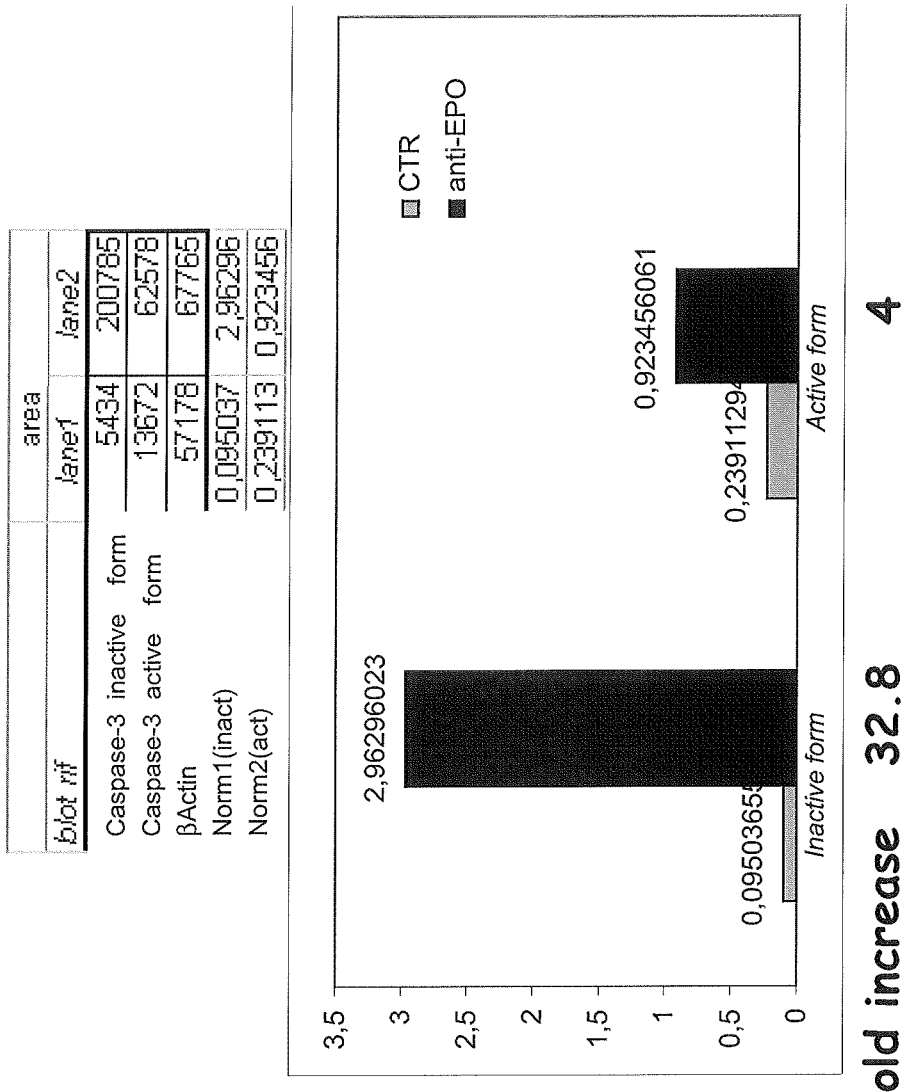
FIG. 20: quantization of the expression levels of Caspase-3.

FIG. 19 shows how, in the presence of the treatment with anti-EPO, the expression levels of the active and the inactive forms of Caspase 3 have increased. The quantization of the bands and their normalization, shown in FIG. 20, show an accumulation of about 33 times the levels of inactive Caspase 3 and about 4 times the levels of active Caspase 3 in the samples exposed to treatment with anti-EPO compared to the untreated control.

Figure 21:
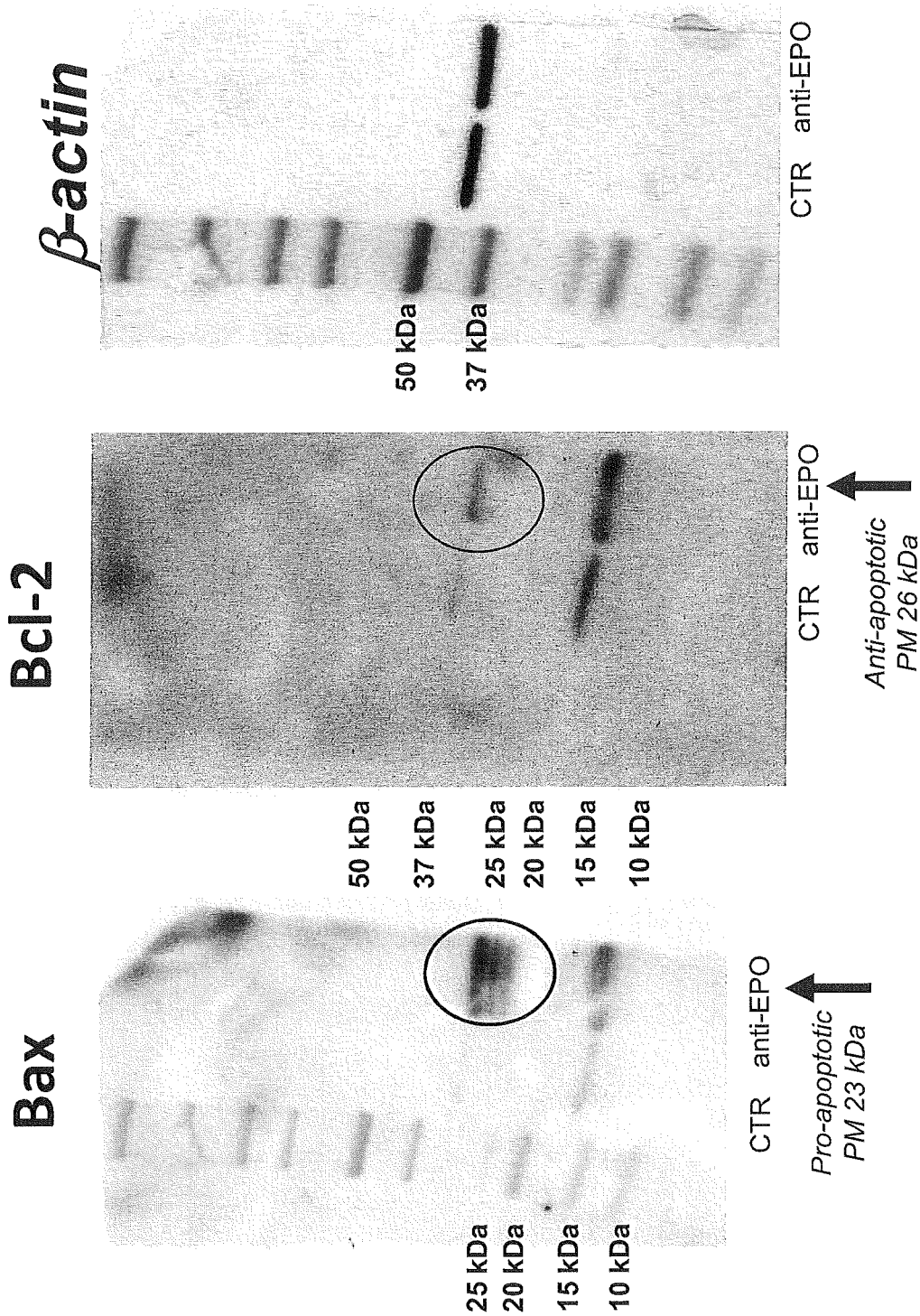
FIG. 21: Western Blot with anti-Bax and anti-Bc12 antibodies and loading control using Beta actin.
Figure 22:
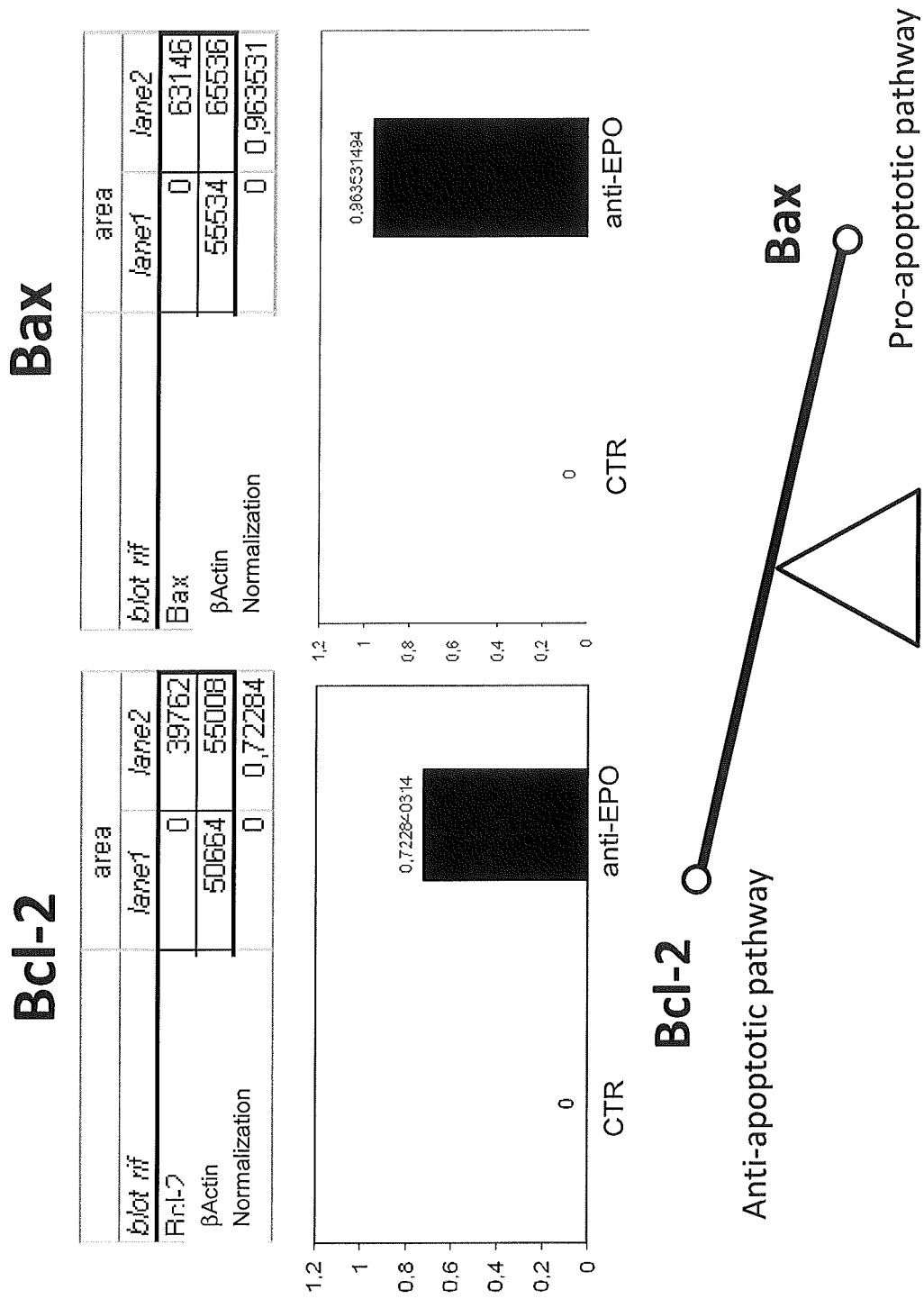
FIG. 22: quantization of the expression levels of Bc12 and Bax.

By assessing the expression levels of Bax and Bc12, there is, in the presence of the treatment with anti-EPO, a shift of the ratio Bc12/Bax in favor of Bax, that is in favor of the pro-apoptotic molecule (FIGS. 21, 22). The data reported herein demonstrate that treatment with anti-EPO is able to induce cell death by apoptosis.

Example 5

Analysis of Annexin V/propidium Iodide by Flow Cytometry

Figure 23:
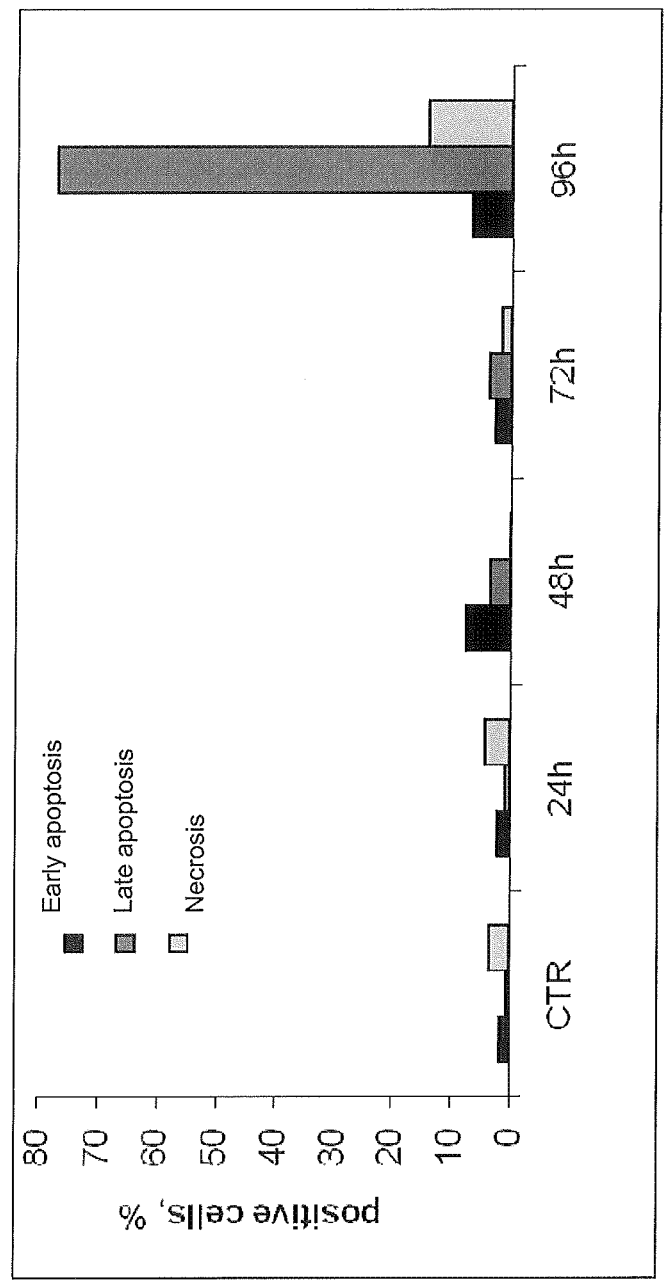
FIG. 23: flow cytometry with staining with Annexin V and propidium iodide in the control sample, treated for 24, 48, 72, 96 hours with anti-EPO.

To confirm the fact that exposure to anti-EPO is able to induce an apoptotic-type of cell death, cells were assessed by flow cytometry with staining with Annexin V and Propidium Iodide. Negative V-FITC annexin cells and negative PI cells are non-apoptotic cells, positive V-FITC annexin cells and negative PI cells are cells at an early stage of apoptosis positive V-FITC annexin cells and positive PI cells are cells in a late stage of apoptosis, negative V-FITC annexin cells and positive PI cells are cells in necrosis. At 48 hours after initiation of treatment, FIG. 23, a number of cells in the initial phase of apoptosis are found, whereas at 96 hours from the treatment, the majority of cells (about 75%) are in late stage apoptosis. The proportion of cells in necrosis is always limited. This confirms that anti-EPO induces apoptotic cell death.

Example 6

Analysis of the Expression of PCNA (Proliferating Cell Nuclear Antigen)

Figure 24:
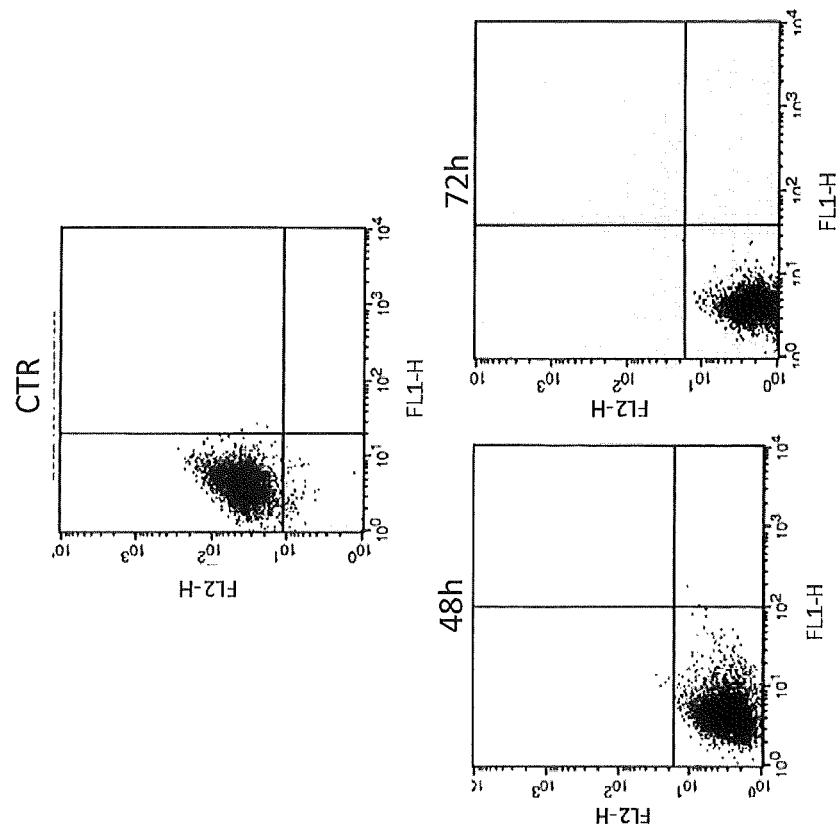
FIG. 24: analysis of the expression of PCNA in control and treated sample for 48 and 72 hours with anti-EPO.

The cells were analyzed for expression of PCNA protein, cellular proliferation index, as shown in FIG. 24. Flow cytometric analysis of the expression of the PCNA protein indicates that untreated glioblastoma cells (CTR) have a high expression of the protein, identifiable by dot plot of the cell population control. After 48 hours of treatment with anti-EPO a decreased positivity of the cells expressing PCNA was measured, detectable by a decrease in fluorescence intensity expressed by the dot plot. This trend is clearly greater at 72 hours of treatment.

Example 7

Analysis of the Expression Levels of Sphingosine Kinase 1 (SK1) and Sphingosine Kinase 2 (SK2)

In the SC02 cells treated or untreated with anti-EPO (H-162), the expression levels of SK1 and SK2 were measured. The levels of beta-actin were used as a normalization factor of the amount of protein loaded. The analysis was conducted on protein lysate obtained after 48 hours from the treatment. For the detection, antibodies developed in rabbit anti SK1 and anti SK2 by Abcam (Cambridge, UK) were used.

Figure 25:
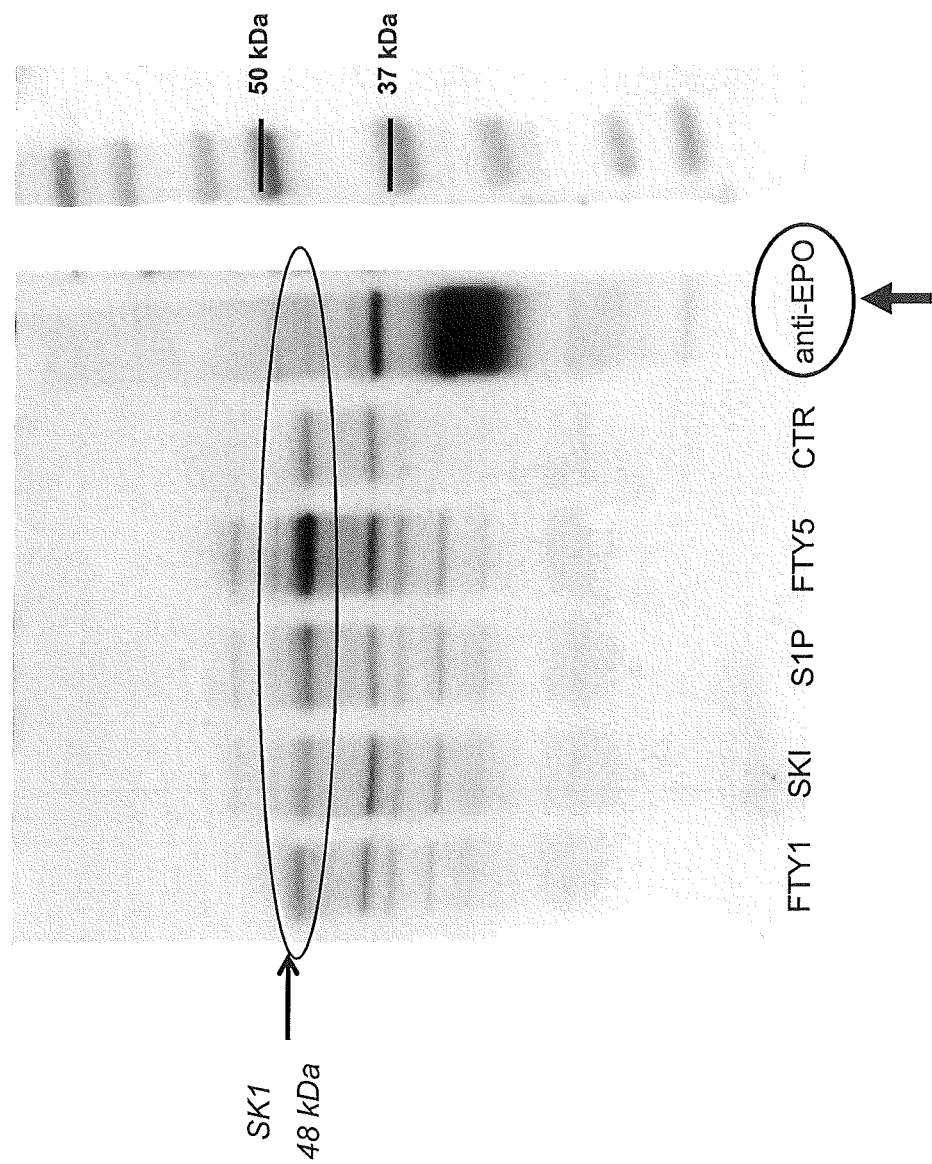
FIG. 25: analysis of the expression levels of SK1 by Western Blot.

FIG. 25 Shows the Expression Levels of SK1 in Glioblastoma Cells Treated as Follows:
FTY=FTY720, 1 µM
SKI=Sphingosine kinase inhibitor, 2 µM
S1P=sphingosine-1-phosphate, 200 nM
FTY5=FTY720, 5 µM
CTR=GSCs cells cultured for 48 hours without any treatment
anti-EPO=GSCs cells treated with anti-EPO antibody All treatments were performed for 48 hours in culture prior to obtaining the lysate protein. The data reported show that, in the presence of the treatment with anti-EPO, the expression levels of SK1 decreased significantly.

Figure 26:
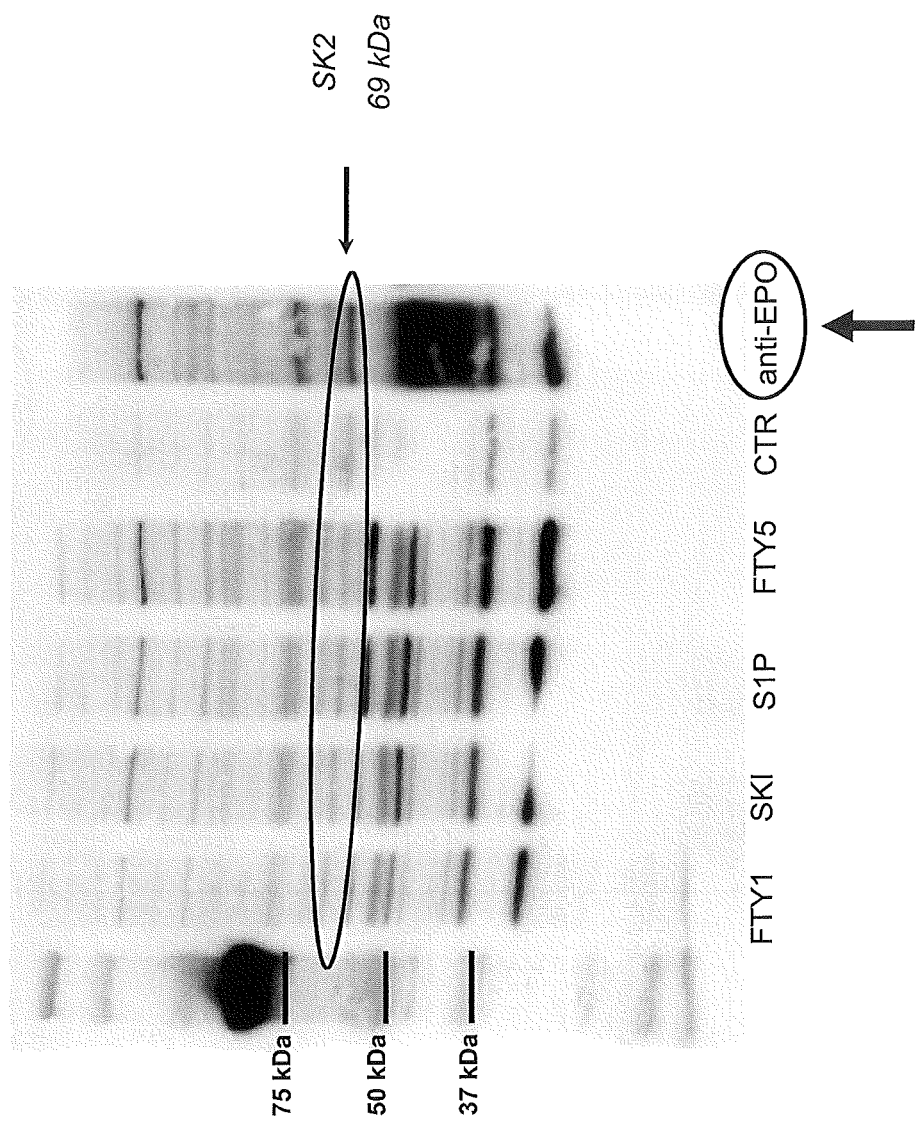
FIG. 26: analysis of the expression levels of SK2 by Western Blot.

FIG. 26 shows how, in the presence of the treatment with anti-EPO, the expression levels of SK2 instead remain unchanged.

The cells were treated as follows:
FTY1=FTY720, 1 µM
SKI=inhibitor of sphingosine kinase, 2 µM
S1P=sphingosine-1-phosphate, 200 nM
FTY5=FTY720, 5 µM
CTR=GSCs cells cultured for 48 hours without any treatment
anti-EPO=GSCs cells treated with anti-EPO antibody All treatments were performed for 48 hours in culture prior to obtaining the lysate protein. The observed inhibition of the conversion of sphingosine to sphingosine-1-phosphate, shifts the equilibrium toward the conversion of sphingosine to ceramide through N-acylation instead of phosphorylation.

Example 8

Analysis of Intracellular and Extracellular Levels of Sphingosine-1-Phosphate (S1P)

Figure 27:
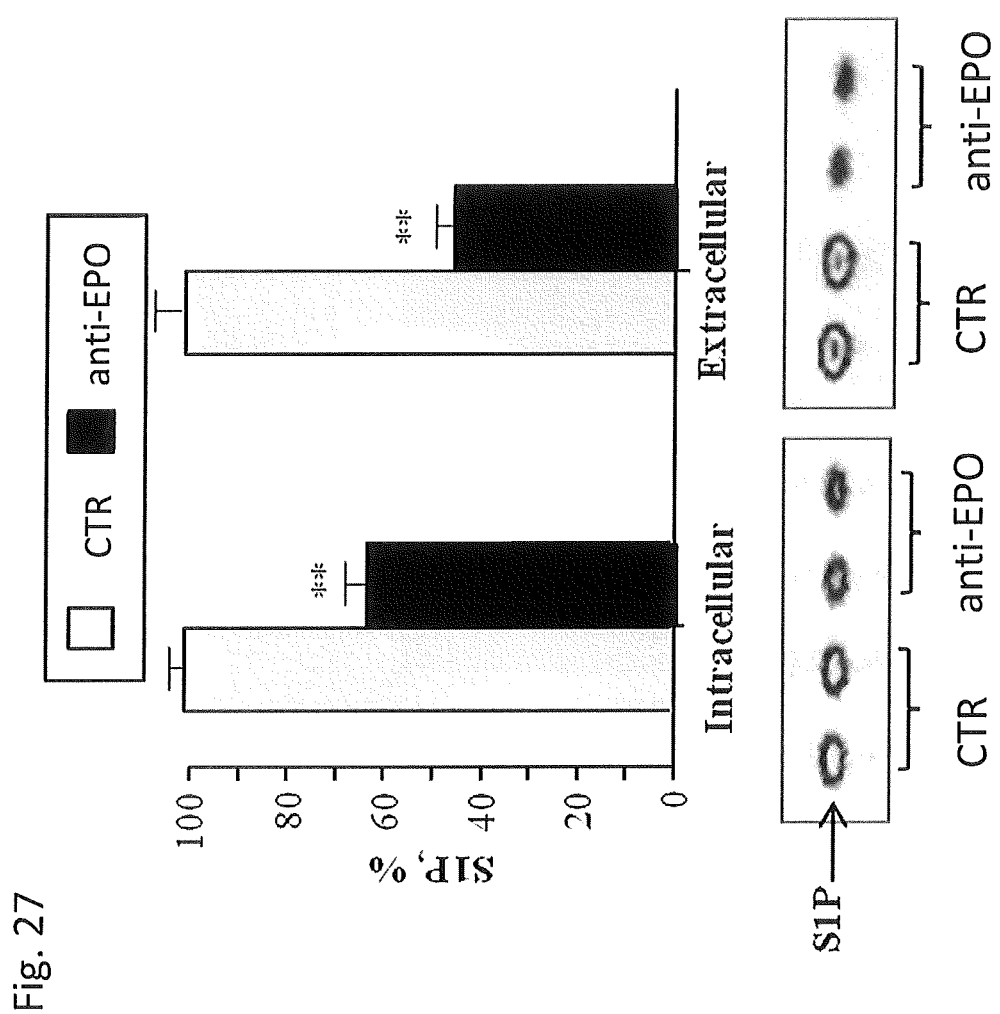
FIG. 27: analysis of the expression levels of intracellular and extracellular S1P by HPTLC after pulse with tritiated sphingosine and relative quantification.

Tritiated sphingosine-1-phosphate was added at a concentration of 200 nM for 48 hours and treated every 24 hours with stem cells of glioblastoma under two conditions: 1) with anti-EPO treatment 2) without further treatment (CTR). Levels of intracellular sphingosine-1-phosphate after 48 hours are reduced by 38% when the cells were treated with anti-EPO (FIG. 27, Intracellular, black column) Extracellular sphingosine-1-phosphate after 48 hours was reduced by 55% following treatment with anti-EPO compared to the control (FIG. 27, Extracellular, black column). This data indicates that the glioblastoma cells are able to release sphingosine-1-phosphate in the extracellular environment and said extracellular release is halved in the presence of treatment with anti-EPO.

Example 9

Figure 28:
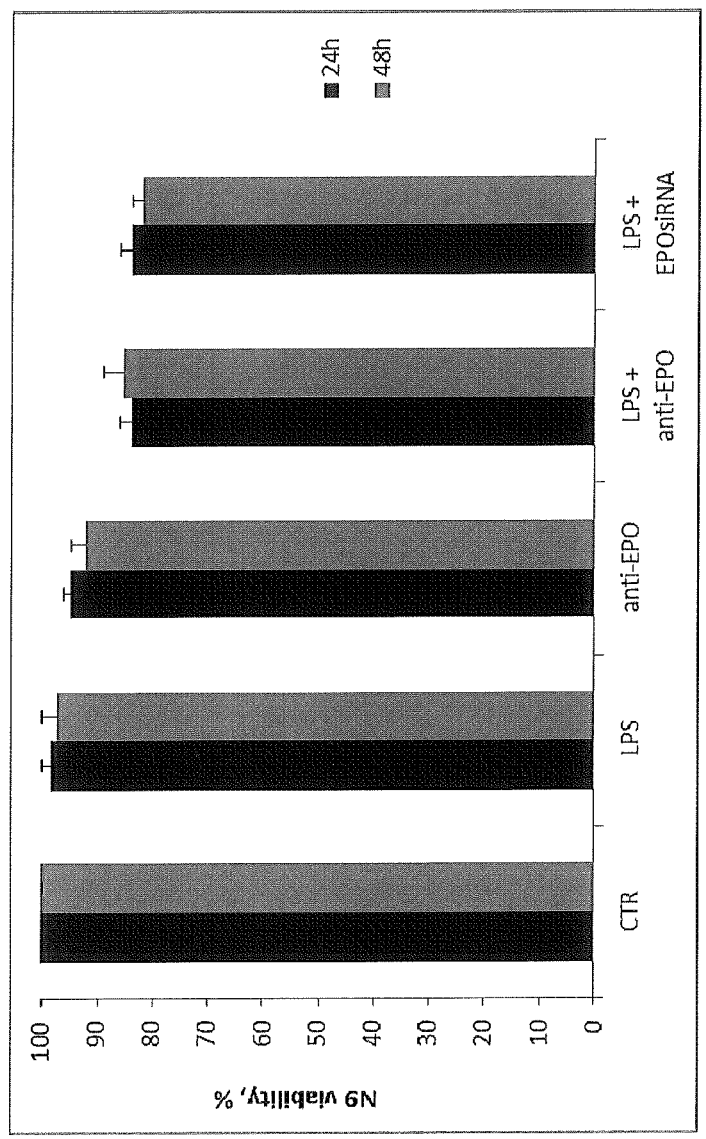
FIG. 28: cell viability count of the cell line of microglia N9

Analysis of the Effect of Treatment with anti-EPO and EPOsiRNA on the Cell Viability of a Commercial Line of Microglia after Inflammatory Stimulus FIG. 28 shows cell viability of commercial line of microglia (line N9).

N9 cells were cultured in Iscove's Modified Dulbecco's MEM, IDMD containing streptomycin/1× penicillin and 2 mM L-glutamine, supplemented with FBS (fetal bovine serum) at 5%.

The cells were plated at a concentration of $1.5 \times 10^{\wedge}4$ cells/cm$^2$ and kept in a thermostatic incubator at 37° C., with 5% $CO_2$, for 24 hours. The next day, the cells were exposed to different treatments for 24 and 48 hours. At the end of the treatments, cell viability was assessed by staining with trypan blue.

The microglia was maintained in a basal culture medium and then activated with lipopolysaccharide (LPS), a molecule present on the membrane of the Gram-negative bacteria.

Furthermore, to study the role of the product "anti-EPO" in the inhibition of neuroinflammation and then in the inhibition of the activation of microglia, the antibody according to the scheme below was administered, in association and not with LPS, to activate microglia. Similarly to the treatment with anti-EPO, a treatment condition of activated microglia with siRNA, using the technique of gene silencing by RNA interference, was combined. This technique allows a reduction of up to 90% of the expression of a protein of interest. The cell in which the silencing of a specific protein is required, is transfected with molecules of double-stranded RNA containing the sequence of about 20bp called small interfering RNA (siRNA).

The cells were exposed to the following treatments:
Control, CTR, (replacement of the culture medium at time 0 with fresh culture medium);
LPS, lipopolysaccharide, at a concentration of 3 µg/ml;
Anti-EPO antibody (H-162) (the culture medium is replaced at time 0 with fresh culture medium containing anti-EPO antibody);
LPS+anti-EPO (at time 0 the cells were plated in culture medium, activated with LPS at a concentration of 3 µg/ml, and treated with anti-EPO antibody (H-162);

LPS+EPOsiRNA (at time 0 the culture medium was replaced with fresh culture medium for transfection with EPOsiRNA). The cells were cultured for 24 hours in a culture medium without antibiotics. The siRNA (Santa Cruz, catalog no. sc-37220) were prepared by diluting to the final concentration directly in the culture medium and incubating at room temperature for 30 minutes. The solution was then added to cells previously washed with 1 ml of medium for the transfection. The cells were incubated for 7 hours and then 1 ml of fresh medium containing a double quantity of FBS and antibiotics was added. The cells were then treated directly in the culture medium with LPS at a concentration of 3 µg/ml and incubated for the next 24 and 48 hours.

It is observed, surprisingly, that treatments with anti-EPO and EPOsiRNA are not toxic for cells of quiescent microglia. The N9, in fact, after 48 hours of culture with different treatments retain a viability higher than 85% and this percentage is higher after 24 hours of treatment.

Example 10

Figure 29:
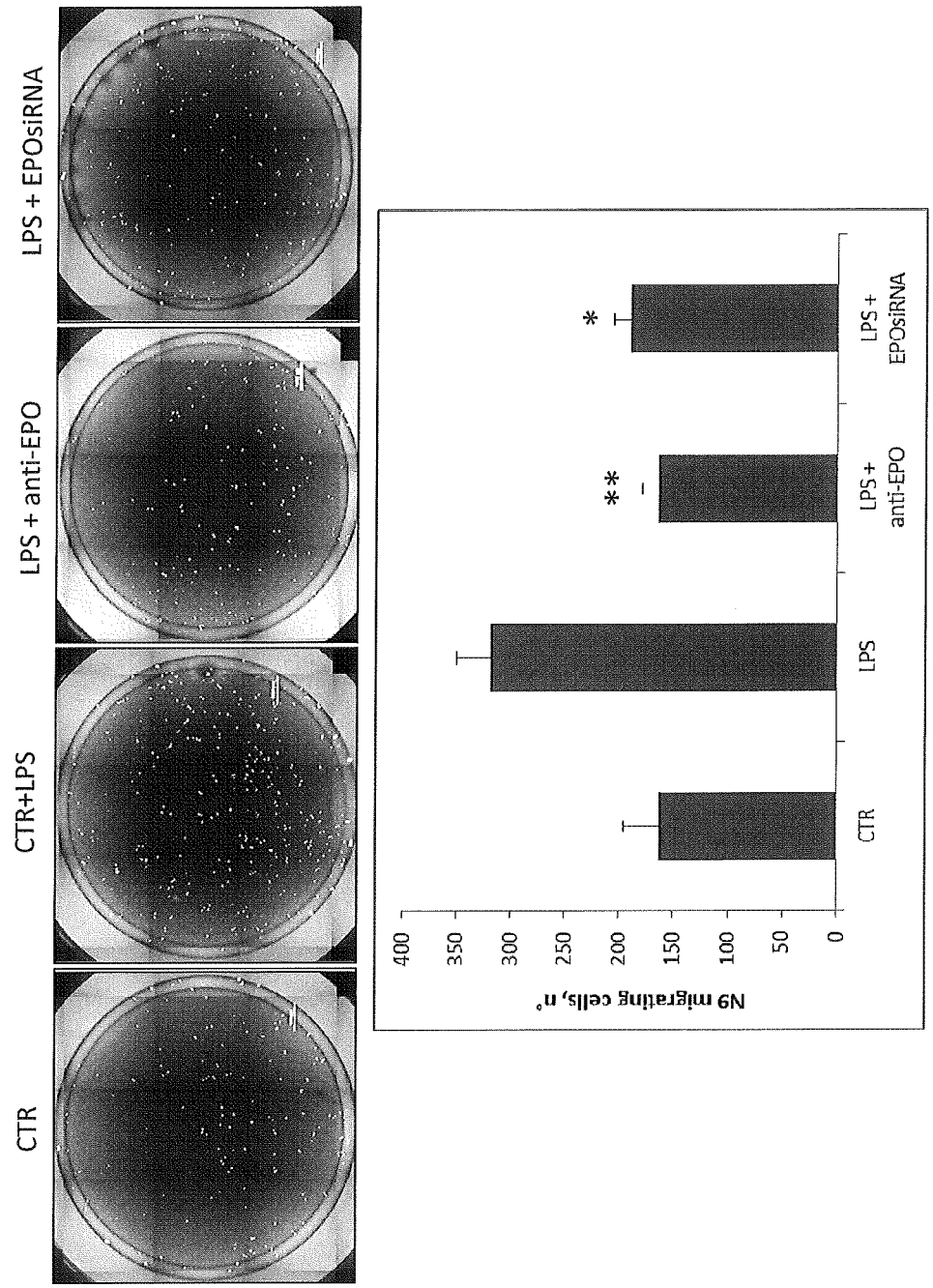
FIG. 29: count of the number of migrating microglial cells

Analysis of the Effect of Treatment with anti-EPO and EPOsiRNA Migration of a Commercial Line of Microglia after Inflammatory Stimulus FIG. 29 shows the ability of treatment with anti-EPO and EPOsiRNA to inhibit the migration of N9. The migration testing or "chemotaxis assay" was carried out to highlight the migratory capacity of N9, a phenomenon that is observed in response to an inflammatory stimulus. For this purpose, transwell multiwell plates (24-well) were used and equipped with inserts with a polycarbonate membrane. The holes in the membrane of a diameter of 8 µM are capable of retaining the cells and the culture medium, but allow the active transmigration of cells through the membrane to reach the lower well.

The normal and N9 and the N9 treated/transfected with EPOsiRNA were seeded in the top insert.

In the lower compartments, LPS at a concentration of 3 µg/ml in IMDM medium, and/or in combination with anti-EPO were added according to the scheme drawn. After 24 hours, the inserts were removed and the cells present in the lower compartment were stained with calceinaAM. The visualization of the cells was made by fluorescence microscopy with a 4× objective and the images were analyzed with ImageJ software. The migration testing shows how N9 cells are chemoattracted by the stimulus with LPS and that this effect is significantly reduced when the medium of the lower compartment is added the anti-EPO antibody and, although to a lesser extent, when the cells are transfected with EPOsiRNA. Therefore, it can be concluded that the "anti-EPO" treatment does not interfere with the quiescent microglia cells, but blocks the activation and migration of the same, as a result of a potent inflammatory stimulus. Treatment with siRNA has positive effects, although greater beneficial effects are observed with antibody "anti-EPO". Therefore, as already seen in the use of the anti-EPOR antibody, where even in that case there were positive but partial effects with respect to those after using anti-EPO polyclonal anti AA. 28-189, it can be assumed that the target of this molecule is not only to seize and reduce levels of EPO preventing receptor binding, but also that in the mixture, are present pharmacologically independently acting molecules or that EPO modulates the functions shown in the experiments, not only through its binding to the receptor.

Example 11

Figure 30:
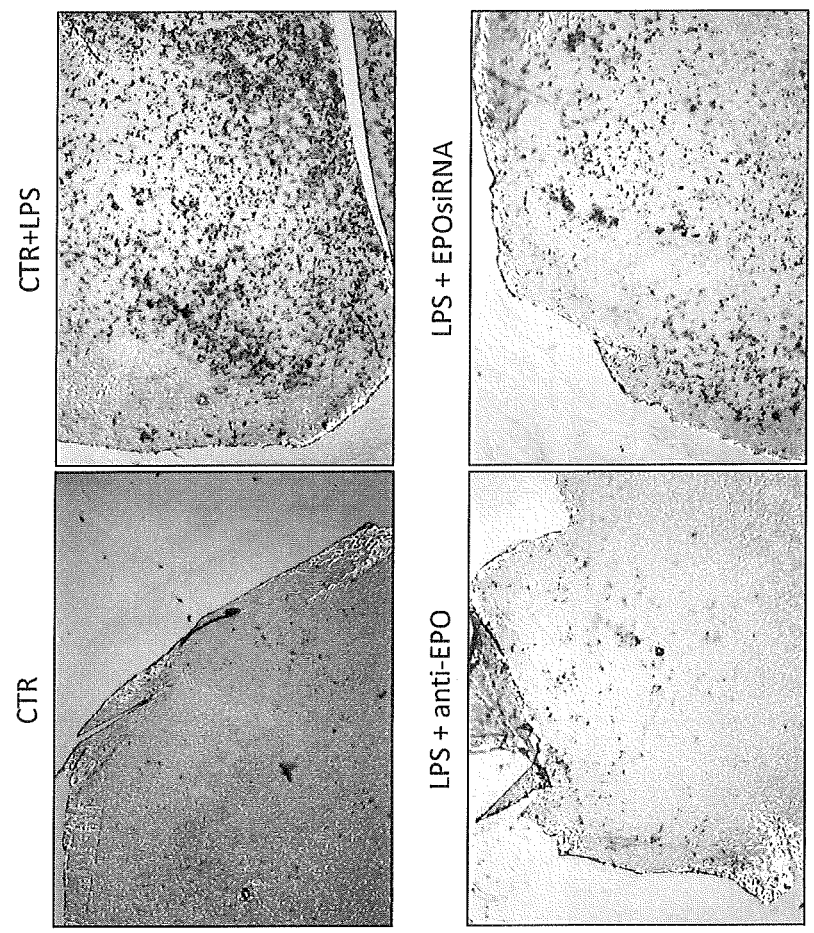
FIG. 30: analysis of the migration of microglial cells infiltrating the insert

Analysis with Hematoxylin and Eosin Staining of the Effect of Treatment with anti-EPO and EPOsiRNA Migration of a Commercial Line of Microglia after Inflammatory Stimulus FIG. 30 shows the analysis of the insert of the transwell plates used for the chemotaxis assay after staining with hematoxylin and eosin. The inserts were removed from the support, turned upside down, laid on a glass holder object and stained with hematoxylin and eosin to highlight the cells which had migrated through the insert. Subsequently, 4 EVOS microscope images with 4x objective were acquired. The analysis of the images showed an increase in the number of cells that had passed through the insert in the presence of LPS in the lower well. Surprisingly, when "anti-EPO" was added to the lower well, the number of migrating cells was significantly reduced to values comparable to the inactivated microglia control. From the qualitative analysis, the inserts processed by the CTR and "anti-EPO" conditions have an almost identical mark.

Example 12

Analysis of the Effect of Treatment with Anti-EPO Individually and in Combination with FTY720 on the Proliferation of a Commercial line of Microglia N9 microglial cells were seeded in multiwell plates at a concentration of $1.5 \times 10^4$ for 24 hours. The following day the cells were administered the following treatments for 24 hours:
LPS;
Anti-EPO antibody administered alone;
Anti-EPO antibody in combination with LPS.

Figure 31:
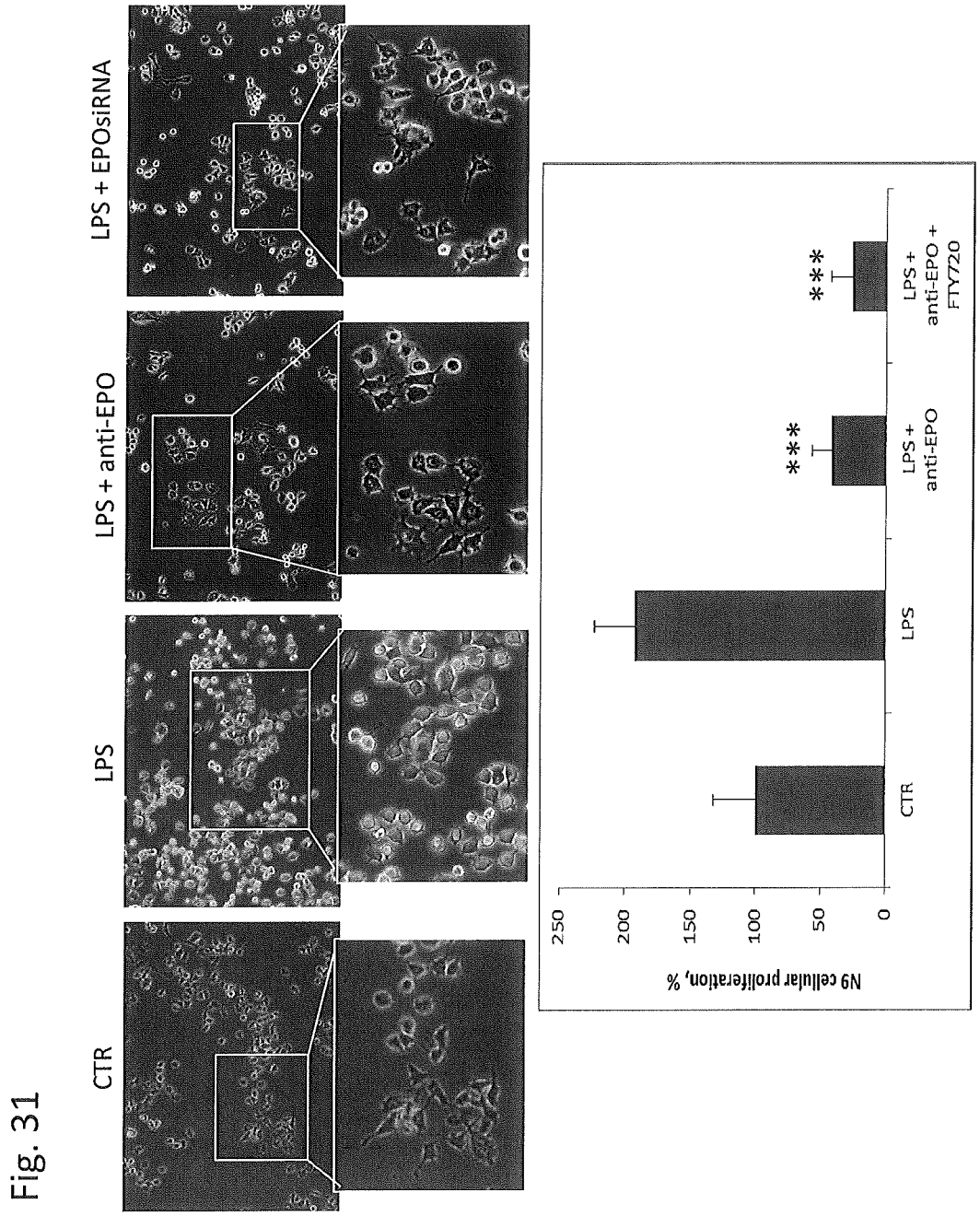
FIG. 31: analysis of cell proliferation of microglial cells

N9 cells were detached with enzyme, and an aliquot of known volume was labeled with trypan blue and observed under the microscope for counting. Considering that the number of cells in the culture control, without any treatment, as being 100, the percentage of proliferation of N9 cultured in presence of LPS, anti-EPO antibody, combination of LPS and anti-EPO antibody was calculated. The data show (FIG. 31) that the stimulus LPS markedly increases cell proliferation in response to inflammatory stimulus and, unlike treatment with anti-EPO, is able to stop the proliferation of microglia following an inflammatory stimulus, maintaining the microglia in a state of quiescence, preventing the inflammatory cascade downstream such as release of inflammatory cytokines, nerve cell death and chronic inflammation. Surprisingly it was seen that even after microglial activation with LPS, the end result is an arrest of proliferation with values comparable to those of quiescent microglia. From a morphological analysis of N9 after stimulation with LPS, a change of the microglia from a branched morphology, typical of a quiescence state, it takes an amoeboid morphology, indicator of a phagocytic activity. Surprisingly, following treatment with "anti-EPO" cells regain or maintain a branched morphology, as well as after having been transfected with EPOsiRNA. This result further emphasizes the effect that the anti-EPO antibody has against neuroinflammation, namely that of stopping the proliferation of the microglia not when it is in a state of resting, quiescence, but more when it is activated.

Example 13

Analysis of the Effect of the Treatment on the Number of Infiltrating Cells of a Commercial Line of Colon Adenocarcinoma, Caco-2

Caco-2 cells, cells of colon adenocarcinoma, are seeded in a Boyden Chamber separated by a silicone septum. Once cell confluence is reached, the septum is removed, and the time it takes for the cells to invade the empty space left after the removal of the septum is measured. Cells occupying this space are counted for the necessary analysis.

The cells were exposed to the following treatments:
Anti-EPO antibody (H-162) (the culture medium is replaced at time 0 with fresh culture medium containing anti-EPO antibody).
Anti-Erythropoietin Receptor antibody (EPOR; the culture medium is replaced at time 0 with fresh culture medium containing anti-EPOR antibody at a concentration of 3 µ/ml).
Control (replacement of the culture medium at time 0 with fresh culture medium).

Figure 32:
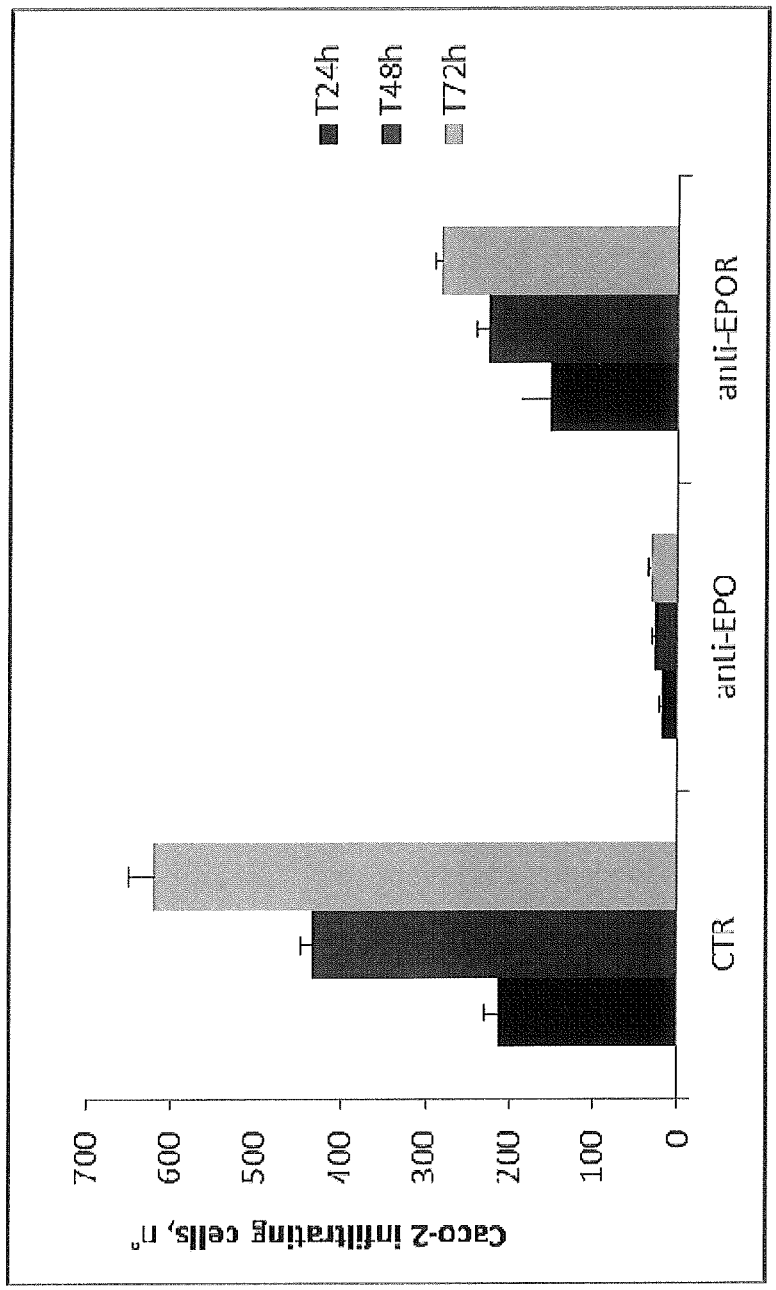
FIG. 32: count of the number of infiltrating Caco-2 cells

It is observed (FIG. 32) that the anti-EPO antibody (H-162) is able to reset the number of infiltrating cells. The anti-EPOR antibody is also capable, albeit less effectively, of decreasing the migration, confirming once again the superior efficacy of the antibody mixture anti-EPO antibody (H-162) relative to the block of EPO, indicating that the therapeutic action also includes different mechanisms in addition to the negative modulation of EPO by blocking its receptor.

Example 14

Analysis of the Effect of Treatment on the Viability of a Commercial Line of Adenocarcinoma of the Colon, Caco-2

Figure 33:
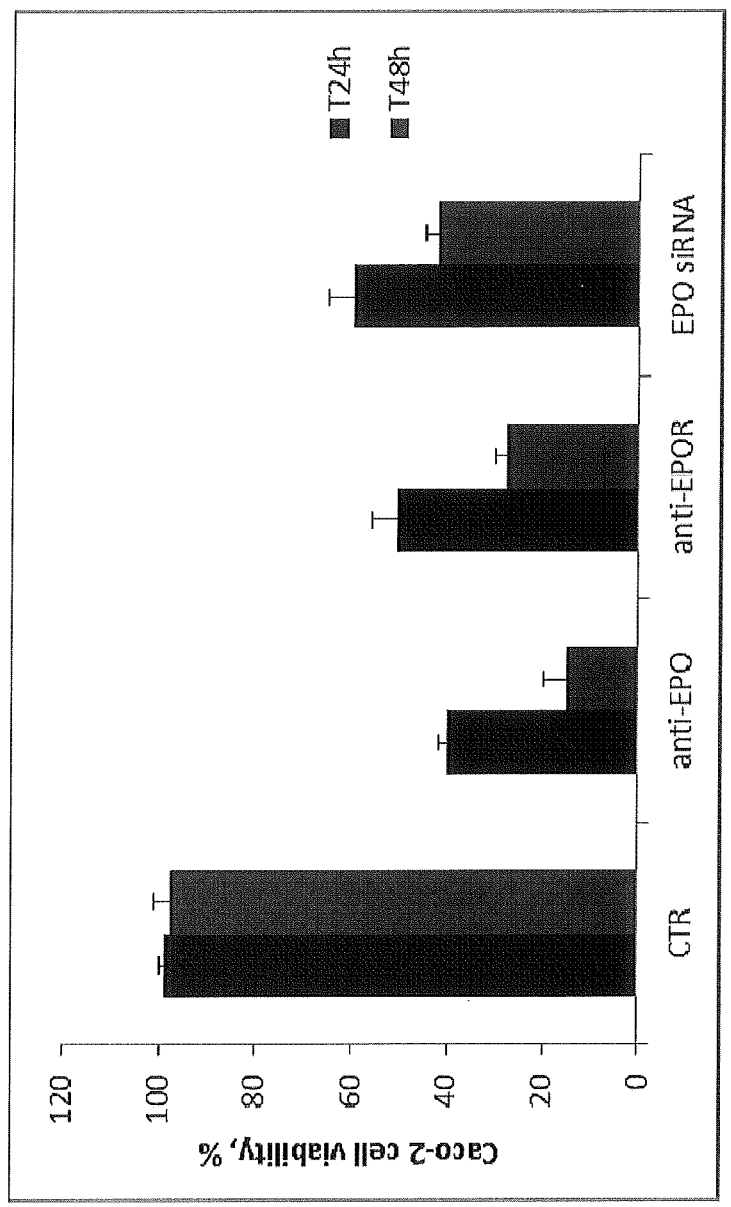
FIG. 33: cell viability count of Caco-2 cells

The analysis of cell viability of Caco-2 shows that at 24 hours after treatment with anti-EPO, only about 40% of the cells initially plated are still alive and this percentage decreases further at 48 hours of treatment (FIG. 33). When the Caco-2 cells are treated with the EPOR antibody, cell proliferation decreases compared to the control even though, in this case also, to a lesser extent compared to treatment with the anti-EPO antibody. Treatment with EPOsiRNA shows that at 24 hours only 60% of the cells are still alive and this percentage decreases at 48 hours. Therefore, positive results with different negative modulators of EPO (anti-EPOR, siRNA) are obtained, but once again, the best effects are achieved by using the polyclonal anti AA 28-189 anti-EPO antibody.

Example 15

Analysis of the Effect of the Treatment on a Number of Infiltrating Cells of a Commercial Line of Non-small Cell Lung Cancer, A549

A549 cells, non-small cell lung cancer cell line, are seeded in a Boyden Chamber separated by a silicone septum. Once the cell confluence is reached, the septum is removed, and the time it takes for the cells to invade the empty space left after the removal of the septum is measured. Cells occupying this space are counted for the necessary analysis.

The cells were exposed to the following treatments:
Control (replacement of the culture medium at time 0 with fresh culture medium);
Anti-EPO antibody (H-162) (the culture medium is replaced at time 0 with fresh culture medium containing anti-EPO antibody);
Anti-Erythropoietin Receptor (EPOR; the culture medium is replaced at time 0 with fresh culture medium containing anti-EPOR antibody).

Figure 34:
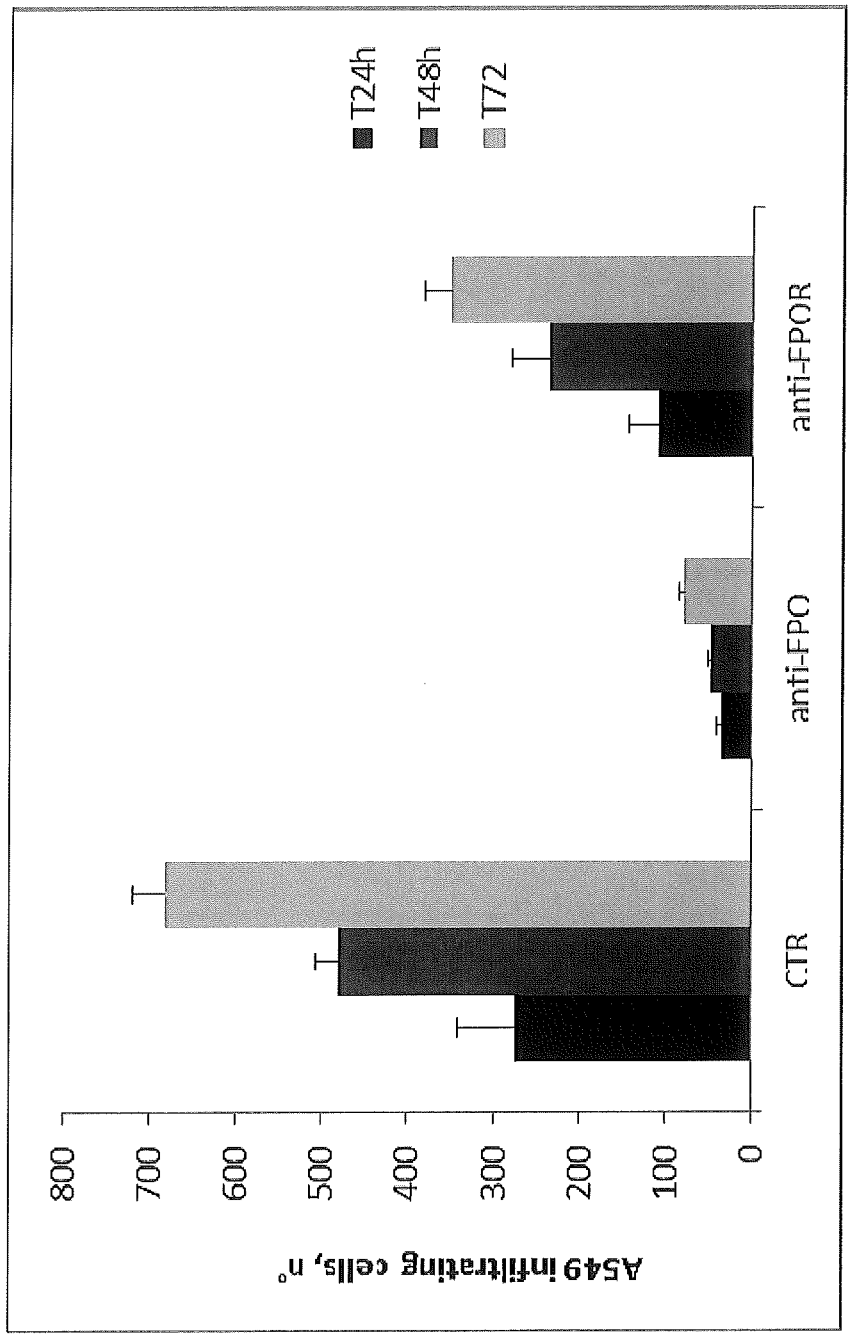
FIG. 34: count of the number of infiltrating A549 cells

It is observed (FIG. 34) that the anti-EPO antibody (H-162) is able to significantly decrease the number of infiltrating cells. The anti-EPOR antibody is also capable, albeit less effectively, to reduce the migration.

Example 16

Analysis of the Effect of the Treatment on the Viability of a Commercial Line of Non-small Cell Lung Cancer, A549

Figure 35:
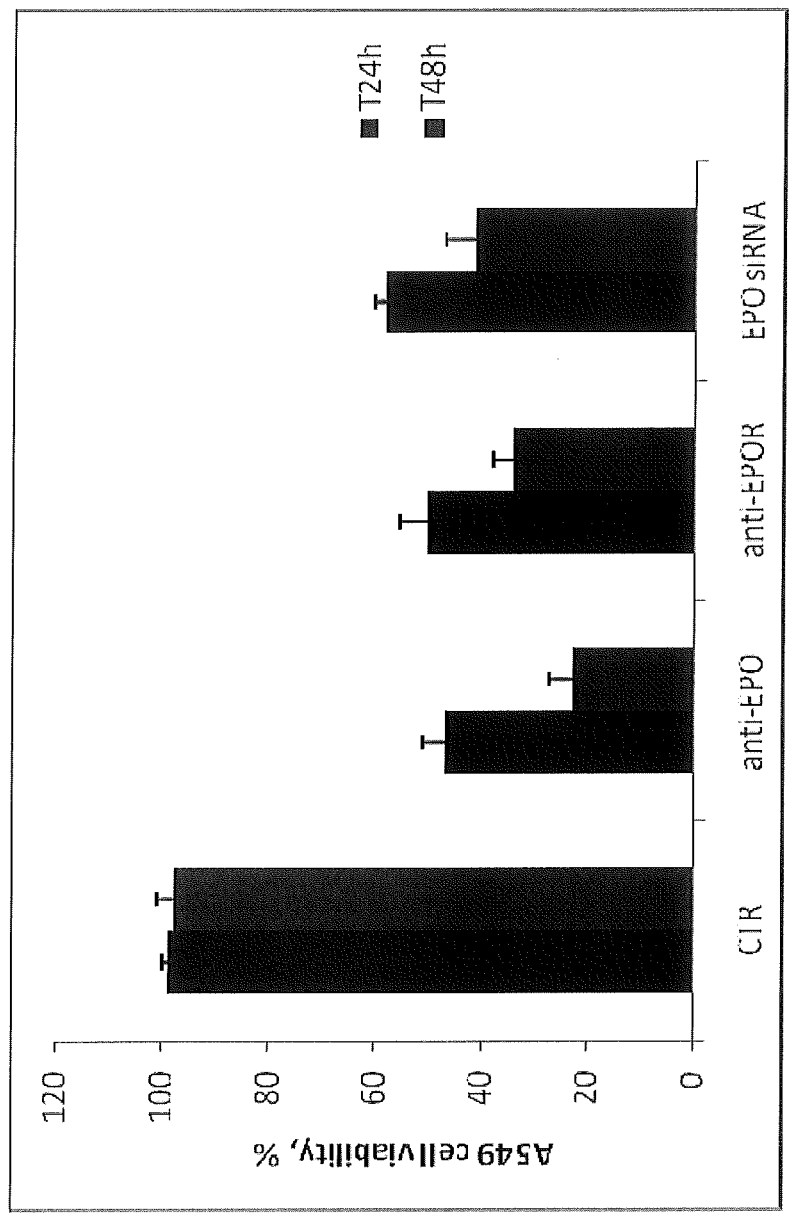
FIG. 35: cell viability count of A549 cells

The analysis of A549 cell viability shows that at 24 hours after treatment with anti-EPO, only about 45% of the cells initially plated are still alive and this percentage decreases further at 48 hours of treatment. When the A549 cells are treated with the anti-EPOR antibody, cell proliferation decreases compared to the control, albeit less when compared to treatment with the anti-EPO antibody. Treatment with EPOsiRNA shows that at 24 hours only 60% of the cells are still alive and this percentage decreases at 48 hours (FIG. 35).

Example 17

Analysis of the Treatments on Cell Viability of Cells of Glioblastoma SC02

Figure 36:
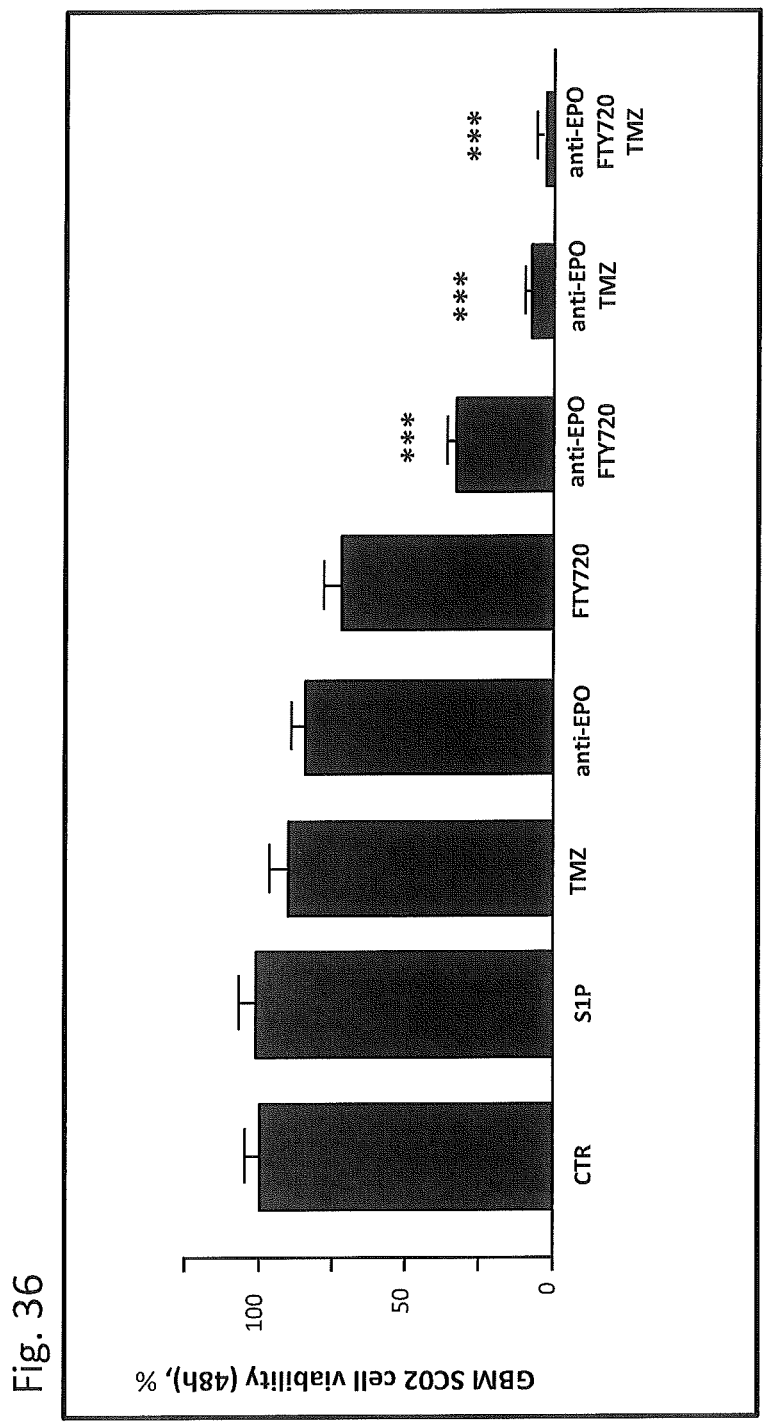
FIG. 36: cell viability count with combined treatment of GBM stem cells at 48 h
Figure 37:
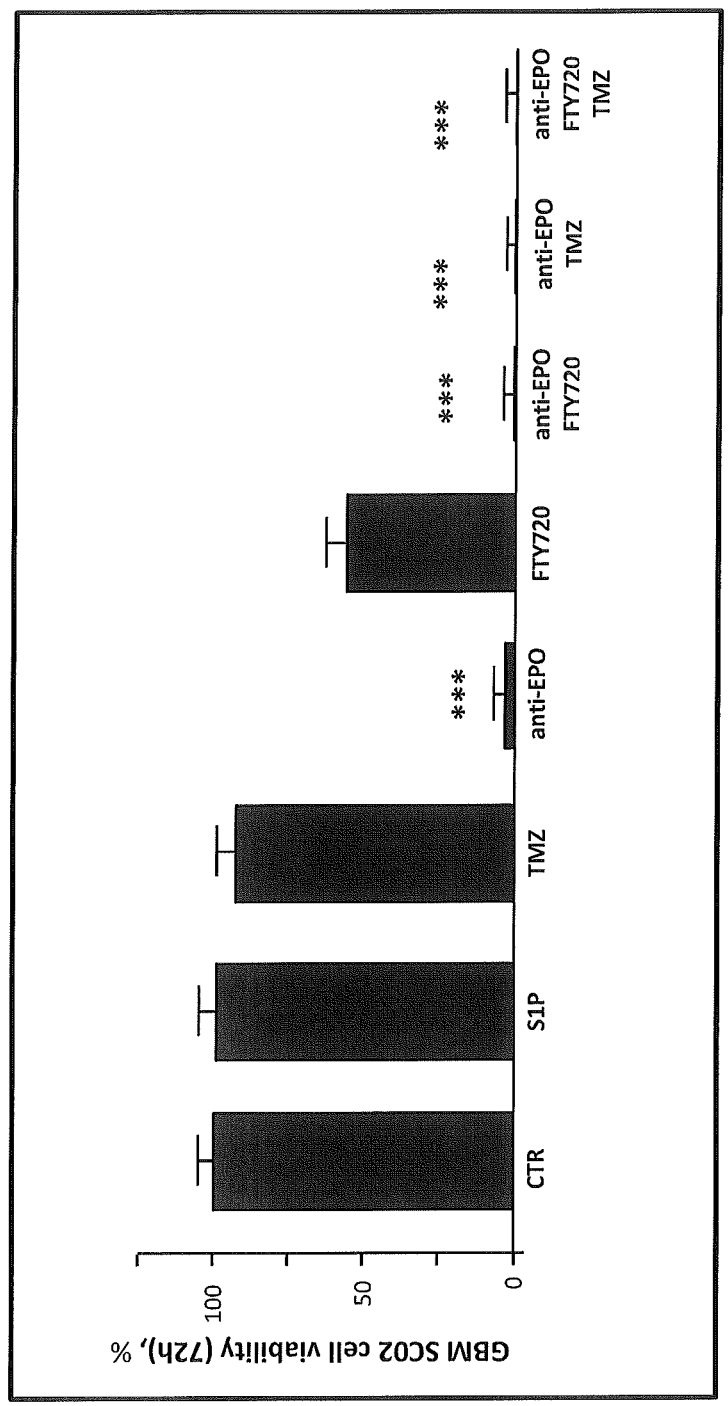
FIG. 37: cell viability count with combined treatment of GBM stem cells at 72 h.

FIGS. 36 and 37 show the analysis of the cell viability of stem cells of glioblastoma subjected to the following treatments respectively for 48 and 72 hours:
Control (replacement of the culture medium at time 0 with fresh culture medium);
Administration of sphingosine-1-phosphate (S1P), 200 nM as a stimulus to the survival and proliferation (positive control);
Administration of Temozolomide (TMZ), the culture medium is replaced at time 0 with fresh culture medium containing TMZ at a concentration 100 µM;
Anti-EPO antibody (H-162) (the culture medium is replaced at time 0 with fresh culture medium containing anti-EPO antibody at a concentration of 3 µg/m1);
Administration of FTY720. The culture medium is replaced at time 0 with fresh culture medium containing FTY720 at a concentration 1 µM;
Combined administration of anti-EPO and FTY720 (the culture medium is replaced at time 0 with fresh culture medium containing anti-EPO antibody and FTY720);
Combined administration of anti-EPO and temozolomide (the culture medium is replaced at time 0 with fresh culture medium containing anti-EPO antibody and TMZ);
Co-administration of anti EPO, FTY720 and TMZ.

Anti-EPO, a peptide that binds EPO and/or a negative functional modulator of the expression levels of EPO prove to be effective molecules for use in the treatment of malignancies. The anti-EPO treatment, in combination with FTY720 is enhanced and synergistic, also the anti-EPO treatment in combination with TMZ (alkylating agent used in the treatment of neurological tumors, to which cancer stem cells are normally resistant) render the neoplastic stem cells sensitive to temozolomide (stem cells from glioblastoma and other cancers are chemotherapy radio resistant, TMZ alkylating agent) again.

Example 18

Figure 38:
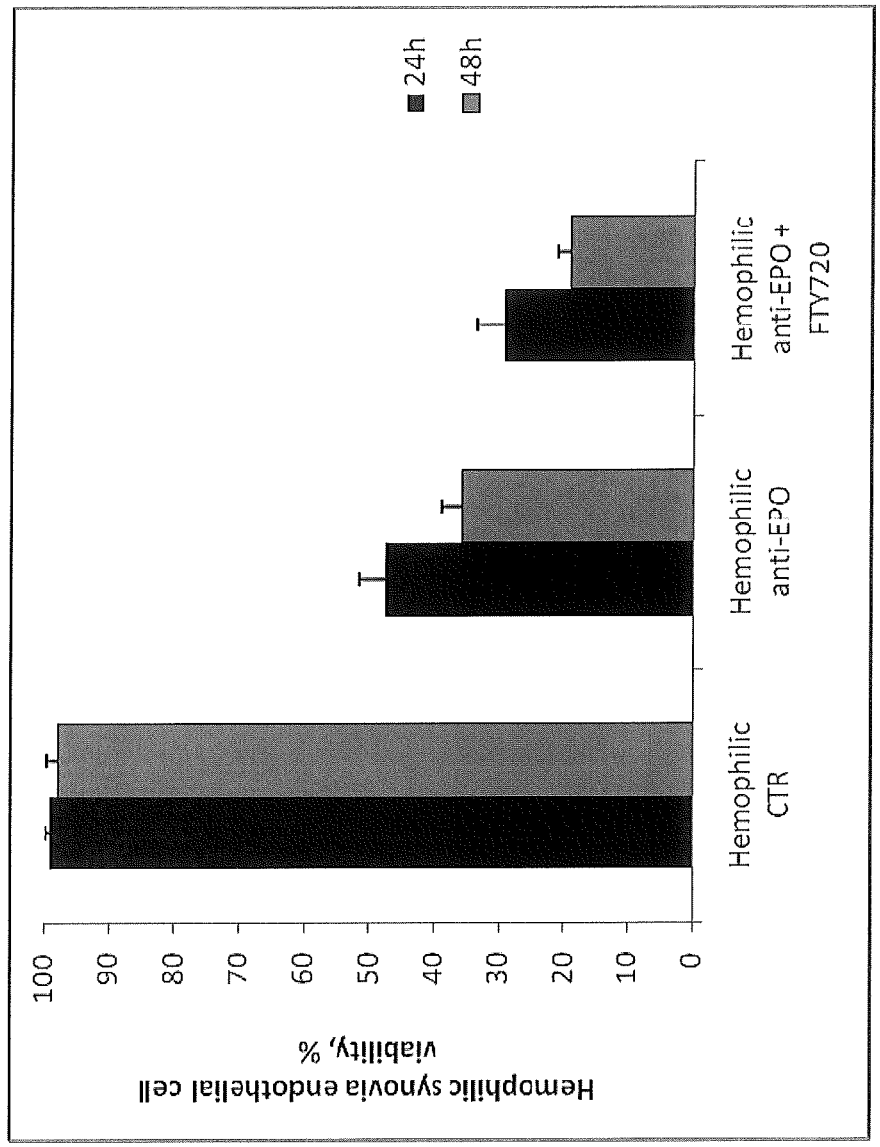
FIG. 38: cell viability count of endothelial cells isolated from the synovium of healthy subjects (CTR) and hemophilic patients

Analysis of the Treatments with Anti-EPO Individually and in Combination with FTY720 on Endothelial Cells Isolated from the Synovium of Hemophilic Patients FIG. 38 shows the analysis of cell viability of endothelial cells isolated from synovium of haemophilia patients with moderate/severe cases of the disease. The endothelial cells were cultured in appropriate culture medium and subjected to the following treatments:
  Control (CTR), replacement of the culture medium at time 0 with fresh culture medium.
  Administration of anti-EPO, replacement of the culture medium at time 0 with fresh culture medium containing anti-EPO at a concentration of 3 µg/ml.
  Administration of anti-EPO in combination with FTY720, replacement of the culture medium at time 0 with fresh culture medium containing anti-EPO at a concentration of 3 µg/ml and FTY720 (1 µM).

When endothelial cells are treated with the anti-EPO antibody, cell proliferation decreases significantly compared to placebo CTR, where the cells are maintained in their culture medium. In addition, the combined treatment with anti-EPO and FTY720 reduces further the survival of synovial endothelial cells of haemophilic patients.

Example 19

Figure 39:
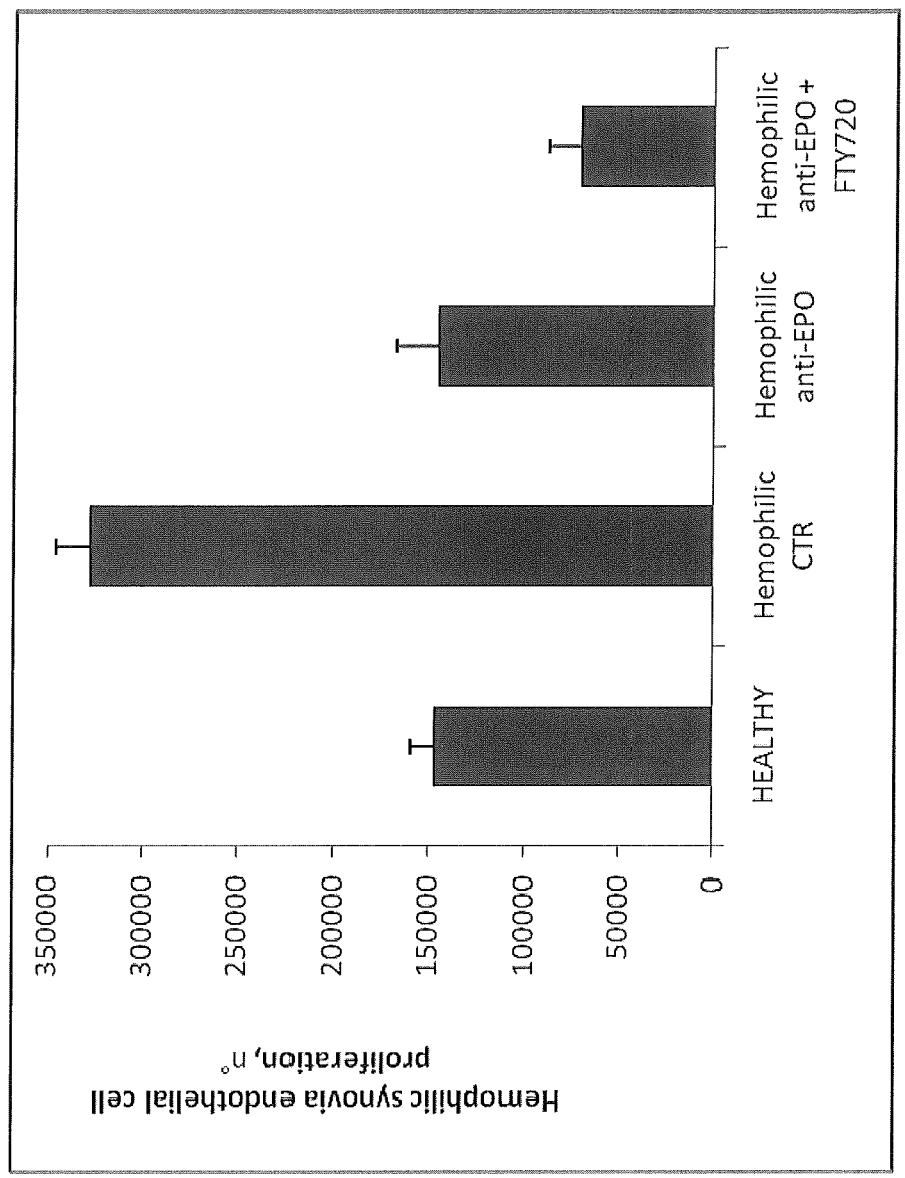
FIG. 39: cell proliferation count of endothelial cells isolated from synovium of healthy subjects (CTR) and hemophilic patients

Analysis of the Treatments with Anti-EPO Individually and in Combination with FTY720 on Endothelial Cells Isolated from Synovium of Healthy Controls and from Haemophilic Patients As shown in FIG. 39, treatment with anti-EPO antibody significantly decreases the proliferation of endothelial cells of the synovium of haemophilic patients as compared to the proliferation of endothelial cells isolated from the synovium of healthy control subjects (HEALTHY).

It is observed that treatment with anti-EPO and the combination of the latter with the inhibitor of S1P, FTY720, are effective in reducing the cell viability of endothelial cells of the pathological synovium.

Example 20

Figure 40:
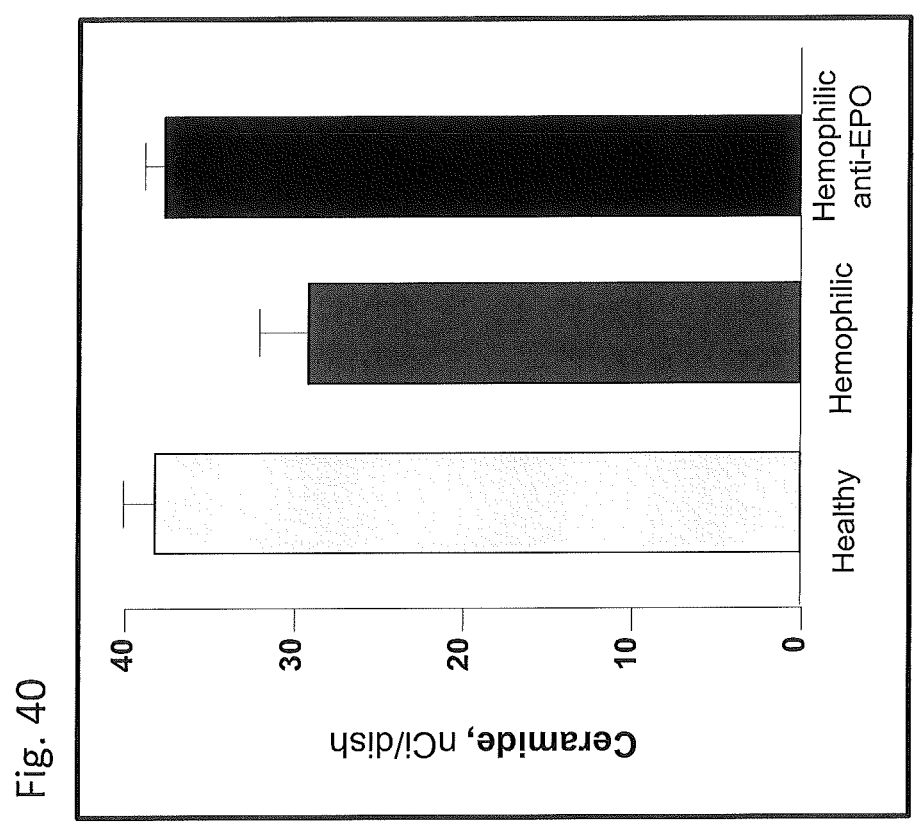
FIG. 40: Levels of ceramide in endothelial cells isolated from synovium of healthy subjects (CTR) and hemophilic patients
Figure 41:
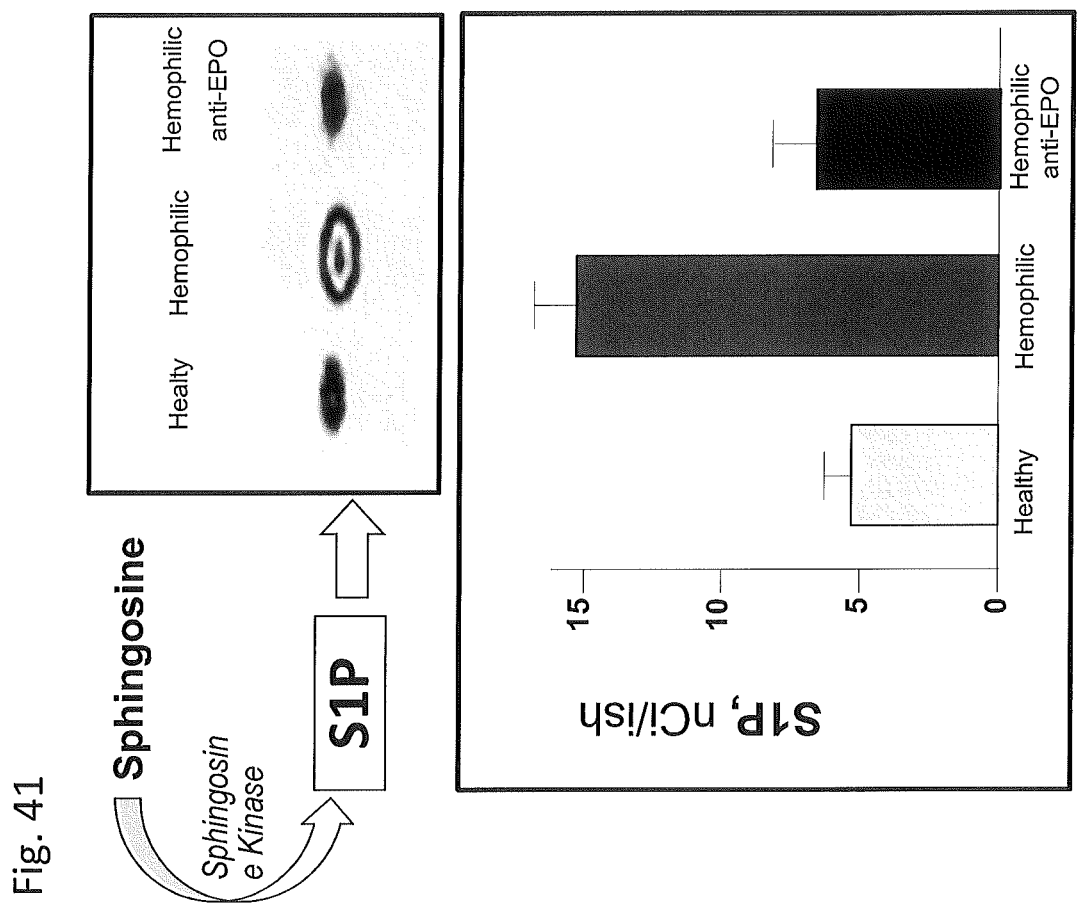
FIG. 41: Levels of sphingosine-1-phosphate intracellular endothelial cells isolated from synovium of healthy subjects and hemophilic patients

Analysis of the Intracellular Levels of Ceramide and Sphingosine-1-Phosphate in the Endothelial Cells of Synovium Taken from Healthy Controls and Pathological Patients Our recent studies of the isolation of endothelial cells from synovium of hemophilic patients for the first time surprisingly demonstrated an increased angiogenesis with reduced stabilization and vessel maturation (tumor-like) at the synovial level especially when compared to their respective controls. The pathological samples also showed a marked increase in the levels of intracellular S1P, capable of promoting pathological angiogenesis and giving rise to an intrinsic inflammatory phenomenon that then involves the entire joint and that is common to both hemophilic arthropathy and Rheumatoid arthritis. For the purpose of the present invention, the endothelial cells from synovial biopsies of 3 healthy subjects and 5 hemophilic patients with moderate/severe pathologies have been isolated and characterized (FIGS. 40-41). The endothelial cells have been used to study the metabolism of sphingolipids, in particular sphingosine-1-phosphate and ceramide, by administering a radiolabelled precursor of S1P and ceramide. It was observed (FIG. 41) that the endothelial cells of synovium taken from pathological patients, had high intracellular levels of S1P (high intracellular levels of S1P contribute to angiogenesis and to triggering an intrinsic inflammatory process) and lower levels of ceramide (for pro-apoptotic action and differentiation towards a more mature cell phenotype) (FIG. 40). Treatment with anti-EPO surprisingly increased levels of ceramide within the endothelial cells of the pathological synovium, which has a pro-apoptotic function. In fact, ceramide levels are increased until arriving at a value similar to that of healthy subjects, and then to a physiological state, showing intracellular levels of S1P of values comparable to those of synovial endothelial cells of healthy subjects. It is possible therefore to hypothesize the use of the anti-EPO antibody, such as in direct intra-articular treatment in the form of gel or suspension, in association or not with "coagulation factors and their derivatives" and also comprising FTY720 and negative modulators of the sphingosine-1-phosphate pathway.

Example 21

Figure 42:
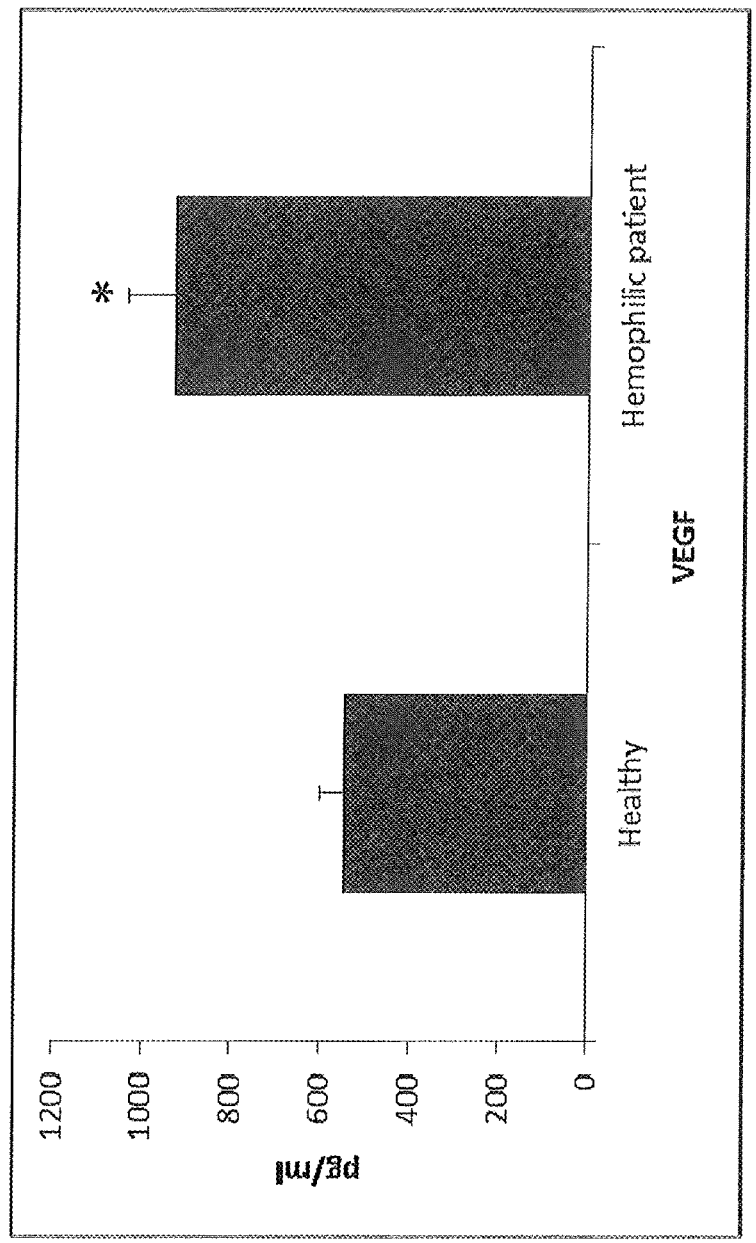
FIG. 42: Measure of the levels of VEGF released in the culture media conditioned by endothelial cells isolated from synovium of control subjects and hemophilic patients.

Analysis with Enzyme-linked ImmunoSorbent Assay (ELISA) of the Levels of VEGF Present in the Conditioned Media from Endothelial Cells Isolated from Synovium of Healthy Controls and Hemophilic Patients FIG. 42 shows the results obtained by enzyme immunoassay Quantikine® ELISA for VEGF (R & D System cod. DVE00) on the supernatants of endothelial cell cultures isolated from synovia of control subjects and haemophiliac patients. The cells were plated at the concentration of $3 \times 10^4$ cells/cm$^2$ for 24 hours at 37° C. and 5% CO$_2$. After incubation, the conditioned supernatants were collected, centrifuged and frozen for analysis. The results, surprisingly, exhibit an increased release in the levels of VEGF by the endothelial cells of hemophilic patients of about double (932±100 pg/ml) with respect to the control subjects (545±115 pg/ml). From this it follows that in hemophilic arthropathy, together with an inflammatory component, the angiogenic process plays a crucial and relevant role in the development of the pathological condition. Therefore, therapies that interfere with angiogenesis and the inherent inflammatory process that ensues, can interrupt the vicious circle of synovitis-bleeding-inflammation.

The invention claimed is:

1. A method of treating with negative functional modulators of erythropoietin (EPO) subjects suffering from glioblastoma multiforme wherein said modulators are molecules that bind EPO selected from the group consisting of
   (i) anti EPO-antibodies, that recognize and bind the AA 28-189 of human EPO (amino acids 1-162 of SEQ ID NO: 2); wherein said negative functional modulator is an anti-EPO polyclonal antibody (H-162), said method comprising administering to said subjects an effective amount of said negative functional modulators of erythropoietin (EPO).

2. The method according to claim 1, comprising administering to said subjects a pharmaceutical composition comprising the modulator according to claim 1 and pharmaceutically acceptable excipients.

3. The method according to claim 2 wherein said pharmaceutical composition further comprises a therapeutically effective amount of one or more natural or synthetic molecules that act on the receptors of S1P, wherein said molecules are selected from the group consisting of FTY720-P, SW-2871, VPC24191, AUY954, SEW2871 (5-[4-phenyl-5-(trifluoromethyl)-2-thienyl]-3-[trifluoromethyl)phenyl]-1,2,4-oxadiazole), VPC23153, DS-GS- 44 and VPC01091.

4. The method according to claim 3, wherein said FTY720 is administered in combination with said anti-EPO polyclonal antibody (H-162).

5. The method according to claim 2, wherein said pharmaceutical composition is formulated as tablets, powder, granules, capsules, liquid agents, injections, suppositories, or slow-release agents.

6. The method according to claim 2, wherein said pharmaceutical composition is administered orally, parenterally, topically, rectally, intravenously, subcutaneously, intramuscularly, intranasally, intravaginally, through the oral mucosa, the lung mucosa or by transocular administration.

* * * * *